US007198937B2

(12) United States Patent
Xue et al.

(10) Patent No.: US 7,198,937 B2
(45) Date of Patent: Apr. 3, 2007

(54) *MORTIERELLA ALPINA* DIACYLGLYCEROL ACYLTRANSFERASE FOR ALTERATION OF POLYUNSATURATED FATTY ACIDS AND OIL CONTENT IN OLEAGINOUS ORGANISMS

(75) Inventors: Zhixiong Xue, Chadds Ford, PA (US); Narendra S. Yadav, Chadds Ford, PA (US); Daniel Joseph Macool, Philadelphia, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 49 days.

(21) Appl. No.: 11/024,545

(22) Filed: Dec. 29, 2004

(65) Prior Publication Data

US 2006/0094087 A1    May 4, 2006

Related U.S. Application Data

(60) Provisional application No. 60/624,812, filed on Nov. 4, 2004.

(51) Int. Cl.
| | |
|---|---|
| *C12N 1/16* | (2006.01) |
| *C12N 1/13* | (2006.01) |
| *C12N 1/19* | (2006.01) |
| *C12N 1/18* | (2006.01) |
| *C12N 9/10* | (2006.01) |
| *C12P 21/06* | (2006.01) |
| *C07H 21/04* | (2006.01) |

(52) U.S. Cl. ............................. 435/254.2; 435/252.3; 435/257.2; 435/254.11; 435/69.1; 435/193; 435/134; 536/23.2

(58) Field of Classification Search ................ 435/22.3, 435/252.3, 193

See application file for complete search history.

(56) References Cited

U.S. PATENT DOCUMENTS

| | | | |
|---|---|---|---|
| 5,244,921 A | 9/1993 | Kyle et al. | |
| 5,407,957 A | 4/1995 | Kyle et al. | |
| 5,492,938 A | 2/1996 | Kyle et al. | |
| 5,658,767 A | 8/1997 | Kyle | |
| 2003/0028923 A1 | 2/2003 | Lardizabal et al. | |
| 2003/0115632 A1 | 6/2003 | Lardizabal et al. | |
| 2003/0124126 A1 | 7/2003 | Cases et al. | |
| 2004/0107459 A1 | 6/2004 | Lardizabal et al. | |

FOREIGN PATENT DOCUMENTS

| | | | |
|---|---|---|---|
| WO | WO 01/34814 A1 | 5/2001 | |
| WO | WO 04/011671 | * 2/2004 | |

OTHER PUBLICATIONS

U.S. Appl. No. 10/840,579, filed May 6, 2004, Picataggio et al.
U.S. Appl. No. 60/624,812, filed Nov. 4, 2004, Zhu et al.
U.S. Appl. No. 10/882,760, filed Jul. 1, 2004, Yadav et al.
Anders Dahlqvist et al., Phospholipid:diacylglycerol acyltransferase: An enzyme that catalyzes the acyl-CoA-independent formation of triacylglycerol in yeast and plants, PNAS, vol. 97(12):6487-6492, 2000.
L. Sandager et al., An acyl-CoA:cholesterol acyltransferase (ACAT)-related gene is involved in the accumulation of triacylglycerols in *Saccharomyces cerevisiae*, Biochemical Society Transactions, vol. 28(6):700-702, 2000.
D. Sorger et al., Triacylglycerol biosynthesis in yeast, Appl. Microbiol. Biotechnol., vol. 61:289-299, 2003.
Line Sandager et al., Storage Lipid Synthesis Is Non-essential in Yeast, The Journal of Biol. Chem., vol. 277(8):6478-6482, 2002.
Kathryn D. Lardizabal et al., DGAT2 Is a New Diacylglycerol Acyltransferase Gene Family, The Journal of Biol. Chem., vol. 276(42):38862-38869, 2001.
National Center for Biotechnology Information General Identifier No. 6324819, Accession No. $NP_{13}$ 014888, Mar. 2, 2005, B. Dujon et al., The nucleotide sequence of *Saccharomyces cerevisiae* chromosome XV.
National Center for Biotechnology Information General Identifier No. 42742309, Accession No. $NC_{13}$ 001147, Mar. 2, 2005, B. Dujon et al., The nucleotide sequence of *Saccharomyces cerevisiae* chromosome XV.
Peter Oelkers et al., The DGA1 Gene Determines a Second Triglyceride Synthetic Pathway in Yeast, The Journal of Biol. Chem., vol. 277(11):8877-8881, 2002.
National Center for Biotechnology Information General Identifier No. 15099960, Accession No. AF391090, Oct. 16, 2001, K. D. Lardizabal et al., DGAT2 is a new diacylglycerol acyltransferase gene family: purification, cloning, and expression in insect cells of two polypeptides from *Mortierella ramanniana* with diacylglycerol acyltransferase activity.
National Center for Biotechnology Information General Identifier No. 38567182, Accession No. CAE76475, Mar. 30, 2003, U. Schulte et al.
Daniel Sorger et al., Synthesis of Triacylglycerols by the Acyl-Coenzyme A:Diacyl-Glycerol Acyltransferase Dga1p in Lipid Particles of the Yeast *Saccharomyces cerevisiae*, Journal of Bacteriology, vol. 184(2):519-524, 2002.
Qian Zhang et al., *Schizosaccharomyces pombe* Cells Deficient in Triacylglycerols Synthesis Undergo Apoptosis upon Entry into the Stationary Phase, The Journal of Biol. Chem., vol. 278(47):47145-47155, 2003.

(Continued)

*Primary Examiner*—Rebecca E. Prouty
*Assistant Examiner*—Iqbal Chowdhury

(57) ABSTRACT

An acyltransferase is provided, suitable for use in the manufacture of microbial oils enriched in omega fatty acids in oleaginous organisms. Specifically, the gene encoding diacylglycerol acyltransferase (DGAT2) has been isolated from *Mortierella alpina*. This gene encodes an enzyme that participates in the terminal step in oil biosynthesis in fungi and yeast and is expected to play a key role in altering the quantity of long-chain polyunsaturated fatty acids produced in oils of oleaginous organisms. Most desirably, the substrate specificity of the instant DGAT2 will be particularly useful to enable accumulation of long-chain PUFAs having chain lengths equal to or greater than $C_{20}$ in oleaginous yeast, such as *Yarrowia lipolytica*.

8 Claims, 5 Drawing Sheets

OTHER PUBLICATIONS

P. Bouvier-Nave et al., Expression in yeast of an acyl-CoA:diacylglycerol acyltransferase cDNA from *Caenorhabditis elegans*, Biochemical Society Transactions, vol. 28(6):692-695, 2000.

Da Silva M. et al., Characterization of Selected Srains of Mucorales Using Fatty Acid Profiles, Rev. Microbiol., vol. 29(4):276-281, Sao Paulo (Oct./Dec. 1998).

* cited by examiner

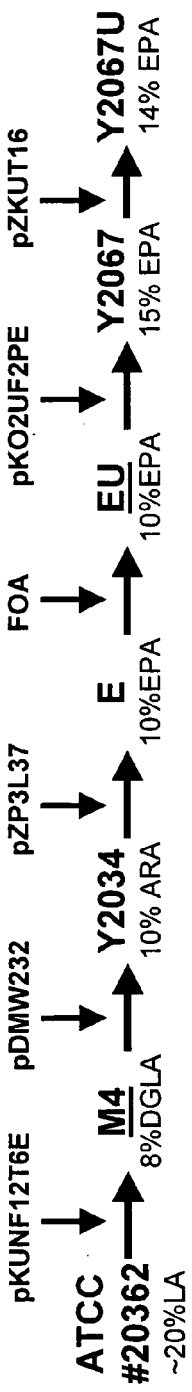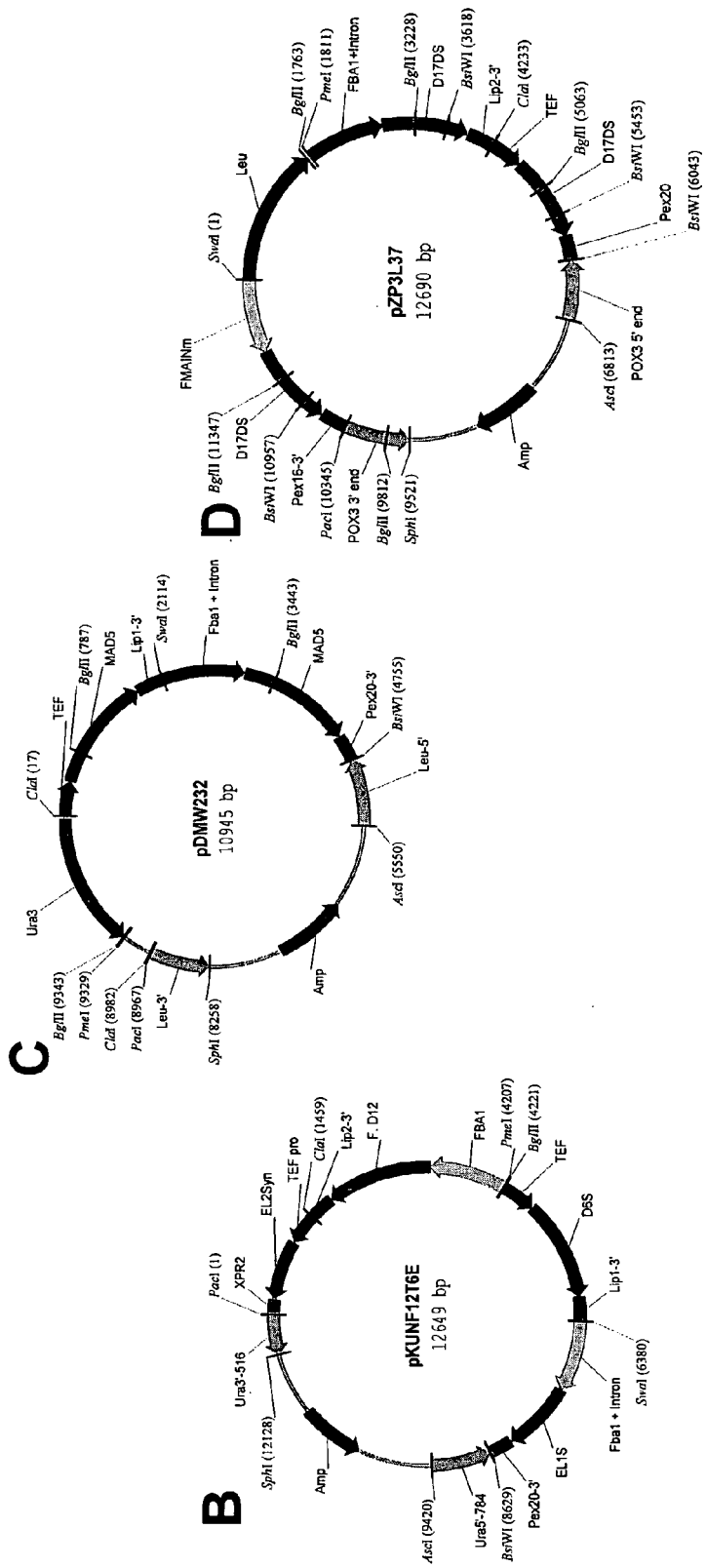
Figure 4

SEQUENCE LISTING

<160> NUMBER OF SEQ ID NOS: 70

<210> SEQ ID NO 1
<211> LENGTH: 996
<212> TYPE: DNA
<213> ORGANISM: M alpina

<400> SEQUENCE: 1

```
atgccgctct ttgcgccttt acggatgccc gtcaagcgtc gtatgcagac aggagctgtc      60
ctatactgga ttgcggggat gatttactgc attggcatct ttgccttcct ctgcacgttc     120
aagatccttc gacccttgat catcatctat gtcctgtggg cctacatgct cgaccgagca     180
ccagagcggg gtgcacgcac agtccaatgg tattgtaact ggatcggatg gaaacacttt     240
gcacagtact ttcctatgac ccttgtcaag gagggagagc tggacccatc caagaactac     300
atctttgggt atcacccaca cggaatcatt tcttgggtg ccctctgcgc ctttgggacc      360
gagggccttc atttctccaa acgcttcccg ggtatcaagc tcatctgct caccattcac     420
gccaactttc agatcccact ctatcgcgat atgatcatgg cccacggctg tgcttccgtg     480
tcgagggcct cttgtgaaca catcctgcgg tctggcgaag gatcctcggt cgtgatcgtt     540
gtcgggggtg cacaagaaag gttgtcgact caacctggca cgttaaatct gacactcaag     600
aaaagactgg gattttgcaa gctggccttt gtcaatggcg caagtctggt acctacgttg     660
gcctttggtg agaacgagct ctatgaggtg taccacacca agcccacaag cctgatatac     720
aagctccagc agttgactaa acgcacgatc ggcttcacaa tgcccgtgtt caacggacga     780
ggaatcttca attrtgagtt tggactgctg ccaaggagga agcctgtcta tatcgttata     840
ggaaacccca ttcatgtaga caaggtcgag aacccaacga ttgaacagat gcagaaactg     900
cagtcaattt acattgatga ggtgctaaac atttgggaaa gatacaagga caagtatgcc     960
gcaggacgaa ctcaggaact gtgcatcatc gaatag                               996
```

<210> SEQ ID NO 2
<211> LENGTH: 331
<212> TYPE: PRT
<213> ORGANISM: M. alpina
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid

<400> SEQUENCE: 2

```
Met Pro Leu Phe Ala Pro Leu Arg Met Pro Val Lys Arg Arg Met Gln
1               5                   10                  15

Thr Gly Ala Val Leu Tyr Trp Ile Ala Gly Met Ile Tyr Cys Ile Gly
            20                  25                  30

Ile Phe Ala Phe Leu Cys Thr Phe Lys Ile Leu Arg Pro Leu Ile Ile
        35                  40                  45

Ile Tyr Val Leu Trp Ala Tyr Met Leu Asp Arg Ala Pro Glu Arg Gly
    50                  55                  60

Ala Arg Thr Val Gln Trp Tyr Cys Asn Trp Ile Gly Trp Lys His Phe
65              70                  75                  80

Ala Gln Tyr Phe Pro Met Thr Leu Val Lys Glu Gly Glu Leu Asp Pro
            85                  90                  95
```

-continued

```
Ser Lys Asn Tyr Ile Phe Gly Tyr His Pro His Gly Ile Ile Xaa Leu
            100                 105                 110

Gly Ala Leu Cys Ala Phe Gly Thr Glu Gly Leu His Phe Ser Lys Arg
        115                 120                 125

Phe Pro Gly Ile Lys Pro His Leu Leu Thr Ile His Ala Asn Phe Gln
    130                 135                 140

Ile Pro Leu Tyr Arg Asp Met Ile Met Ala His Gly Cys Ala Ser Val
145                 150                 155                 160

Ser Arg Ala Ser Cys Glu His Ile Leu Arg Ser Gly Glu Gly Ser Ser
                165                 170                 175

Val Val Ile Val Val Gly Gly Ala Gln Glu Ser Leu Ser Thr Gln Pro
            180                 185                 190

Gly Thr Leu Asn Leu Thr Leu Lys Lys Arg Leu Gly Phe Cys Lys Leu
        195                 200                 205

Ala Phe Val Asn Gly Ala Ser Leu Val Pro Thr Leu Ala Phe Gly Glu
    210                 215                 220

Asn Glu Leu Tyr Glu Val Tyr His Thr Lys Pro Thr Ser Leu Ile Tyr
225                 230                 235                 240

Lys Leu Gln Gln Leu Thr Lys Arg Thr Ile Gly Phe Thr Met Pro Val
                245                 250                 255

Phe Asn Gly Arg Gly Ile Phe Asn Xaa Glu Phe Gly Leu Leu Pro Arg
            260                 265                 270

Arg Lys Pro Val Tyr Ile Val Ile Gly Asn Pro Ile His Val Asp Lys
        275                 280                 285

Val Glu Asn Pro Thr Ile Glu Gln Met Gln Lys Leu Gln Ser Ile Tyr
    290                 295                 300

Ile Asp Glu Val Leu Asn Ile Trp Glu Arg Tyr Lys Asp Lys Tyr Ala
305                 310                 315                 320

Ala Gly Arg Thr Gln Glu Leu Cys Ile Ile Glu
                325                 330

<210> SEQ ID NO 3
<211> LENGTH: 2119
<212> TYPE: DNA
<213> ORGANISM: Yarrowia lipolytica
<220> FEATURE:
<221> NAME/KEY: CDS
<222> LOCATION: (291)..(1835)
<223> OTHER INFORMATION: DGAT2 opening reading frame, comprising 2
      smaller internal opening reading frames
<220> FEATURE:
<221> NAME/KEY: misc_feature
<222> LOCATION: (291)..(293)
<223> OTHER INFORMATION: initiation codon ('ATG')
<220> FEATURE:
<221> NAME/KEY: misc_feature
<222> LOCATION: (456)..(458)
<223> OTHER INFORMATION: initiation codon ('ATG')
<220> FEATURE:
<221> NAME/KEY: misc_feature
<222> LOCATION: (768)..(770)
<223> OTHER INFORMATION: initiation codon ('ATG')

<400> SEQUENCE: 3
aaacgcaccc actgctcgtc ctccttgctc ctcgaaaccg actcctctac acacgtcaaa      60
tccgaggttg aaatcttccc cacatttggc agccaaacca gcacatccca gcaacctcgc     120
acagcgccga atcgacctg tcgacttggc cacaaaaaaa agcaccggct ctgcaacagt      180
tctcacgacc aattacgtac aagtacgaaa tcgttcgtgg accgtgactg ataagctccc     240
```

```
actttttctt ctaacaacag gcaacagaca agtcacacaa aacaaaagct atg act              296
                                                        Met Thr
                                                          1 atc gac tca caa tac tac aag tcg cga gac aaa aac gac acg gca ccc              344
Ile Asp Ser Gln Tyr Tyr Lys Ser Arg Asp Lys Asn Asp Thr Ala Pro
         5                  10                  15 aaa atc gcg gga atc cga tat gcc ccg cta tcg aca cca tta ctc aac              392
Lys Ile Ala Gly Ile Arg Tyr Ala Pro Leu Ser Thr Pro Leu Leu Asn
     20                  25                  30 cga tgt gag acc ttc tct ctg gtc tgg cac att ttc agc att ccc act              440
Arg Cys Glu Thr Phe Ser Leu Val Trp His Ile Phe Ser Ile Pro Thr
 35                  40                  45                  50 ttc ctc aca att ttc atg cta tgc tgc gca att cca ctg ctc tgg cca              488
Phe Leu Thr Ile Phe Met Leu Cys Cys Ala Ile Pro Leu Leu Trp Pro
                     55                  60                  65 ttt gtg att gcg tat gta gtg tac gct gtt aaa gac gac tcc ccg tcc              536
Phe Val Ile Ala Tyr Val Val Tyr Ala Val Lys Asp Asp Ser Pro Ser
                 70                  75                  80 aac gga gga gtg gtc aag cga tac tcg cct att tca aga aac ttc ttc              584
Asn Gly Gly Val Val Lys Arg Tyr Ser Pro Ile Ser Arg Asn Phe Phe
             85                  90                  95 atc tgg aag ctc ttt ggc cgc tac ttc ccc ata act ctg cac aag acg              632
Ile Trp Lys Leu Phe Gly Arg Tyr Phe Pro Ile Thr Leu His Lys Thr
        100                 105                 110 gtg gat ctg gag ccc acg cac aca tac tac cct ctg gac gtc cag gag              680
Val Asp Leu Glu Pro Thr His Thr Tyr Tyr Pro Leu Asp Val Gln Glu
115                 120                 125                 130 tat cac ctg att gct gag aga tac tgg ccg cag aac aag tac ctc cga              728
Tyr His Leu Ile Ala Glu Arg Tyr Trp Pro Gln Asn Lys Tyr Leu Arg
                    135                 140                 145 gca atc atc tcc acc atc gag tac ttt ctg ccc gcc ttc atg aaa cgg              776
Ala Ile Ile Ser Thr Ile Glu Tyr Phe Leu Pro Ala Phe Met Lys Arg
                150                 155                 160 tct ctt tct atc aac gag cag gag cag cct gcc gag cga gat cct ctc              824
Ser Leu Ser Ile Asn Glu Gln Glu Gln Pro Ala Glu Arg Asp Pro Leu
            165                 170                 175 ctg tct ccc gtt tct ccc agc tct ccg ggt tct caa cct gac aag tgg              872
Leu Ser Pro Val Ser Pro Ser Ser Pro Gly Ser Gln Pro Asp Lys Trp
        180                 185                 190 att aac cac gac agc aga tat agc cgt gga gaa tca tct ggc tcc aac              920
Ile Asn His Asp Ser Arg Tyr Ser Arg Gly Glu Ser Ser Gly Ser Asn
195                 200                 205                 210 ggc cac gcc tcg ggc tcc gaa ctt aac ggc aac ggc aac aat ggc acc              968
Gly His Ala Ser Gly Ser Glu Leu Asn Gly Asn Gly Asn Asn Gly Thr
                    215                 220                 225 act aac cga cga cct ttg tcg tcc gcc tct gct ggc tcc act gca tct             1016
Thr Asn Arg Arg Pro Leu Ser Ser Ala Ser Ala Gly Ser Thr Ala Ser
                230                 235                 240 gat tcc acg ctt ctt aac ggg tcc ctc aac tcc tac gcc aac cag atc             1064
Asp Ser Thr Leu Leu Asn Gly Ser Leu Asn Ser Tyr Ala Asn Gln Ile
            245                 250                 255 att ggc gaa aac gac cca cag ctg tcg ccc aca aaa ctc aag ccc act             1112
Ile Gly Glu Asn Asp Pro Gln Leu Ser Pro Thr Lys Leu Lys Pro Thr
        260                 265                 270 ggc aga aaa tac atc ttc ggc tac cac ccc cac ggc att atc ggc atg             1160
Gly Arg Lys Tyr Ile Phe Gly Tyr His Pro His Gly Ile Ile Gly Met
275                 280                 285                 290 gga gcc ttt ggt gga att gcc acc gag gga gct gga tgg tcc aag ctc             1208
Gly Ala Phe Gly Gly Ile Ala Thr Glu Gly Ala Gly Trp Ser Lys Leu
                    295                 300                 305
```

-continued

```
ttt ccg ggc atc cct gtt tct ctt atg act ctc acc aac aac ttc cga      1256
Phe Pro Gly Ile Pro Val Ser Leu Met Thr Leu Thr Asn Asn Phe Arg
            310                 315                 320 gtg cct ctc tac aga gag tac ctc atg agt ctg gga gtc gct tct gtc      1304
Val Pro Leu Tyr Arg Glu Tyr Leu Met Ser Leu Gly Val Ala Ser Val
        325                 330                 335 tcc aag aag tcc tgc aag gcc ctc ctc aag cga aac cag tct atc tgc      1352
Ser Lys Lys Ser Cys Lys Ala Leu Leu Lys Arg Asn Gln Ser Ile Cys
    340                 345                 350 att gtc gtt ggt gga gca cag gaa agt ctt ctg gcc aga ccc ggt gtc      1400
Ile Val Val Gly Gly Ala Gln Glu Ser Leu Leu Ala Arg Pro Gly Val
355                 360                 365                 370 atg gac ctg gtg cta ctc aag cga aag ggt ttt gtt cga ctt ggt atg      1448
Met Asp Leu Val Leu Leu Lys Arg Lys Gly Phe Val Arg Leu Gly Met
                375                 380                 385 gag gtc gga aat gtc gcc ctt gtt ccc atc atg gcc ttt ggt gag aac      1496
Glu Val Gly Asn Val Ala Leu Val Pro Ile Met Ala Phe Gly Glu Asn
            390                 395                 400 gac ctc tat gac cag gtt agc aac gac aag tcg tcc aag ctg tac cga      1544
Asp Leu Tyr Asp Gln Val Ser Asn Asp Lys Ser Ser Lys Leu Tyr Arg
        405                 410                 415 ttc cag cag ttt gtc aag aac ttc ctt gga ttc acc ctt cct ttg atg      1592
Phe Gln Gln Phe Val Lys Asn Phe Leu Gly Phe Thr Leu Pro Leu Met
    420                 425                 430 cat gcc cga ggc gtc ttc aac tac gat gtc ggt ctt gtc ccc tac agg      1640
His Ala Arg Gly Val Phe Asn Tyr Asp Val Gly Leu Val Pro Tyr Arg
435                 440                 445                 450 cga ccc gtc aac att gtg gtt ggt tcc ccc att gac ttg cct tat ctc      1688
Arg Pro Val Asn Ile Val Val Gly Ser Pro Ile Asp Leu Pro Tyr Leu
                455                 460                 465 cca cac ccc acc gac gaa gaa gtg tcc gaa tac cac gac cga tac atc      1736
Pro His Pro Thr Asp Glu Glu Val Ser Glu Tyr His Asp Arg Tyr Ile
            470                 475                 480 gcc gag ctg cag cga atc tac aac gag cac aag gat gaa tat ttc atc      1784
Ala Glu Leu Gln Arg Ile Tyr Asn Glu His Lys Asp Glu Tyr Phe Ile
        485                 490                 495 gat tgg acc gag gag ggc aaa gga gcc cca gag ttc cga atg att gag      1832
Asp Trp Thr Glu Glu Gly Lys Gly Ala Pro Glu Phe Arg Met Ile Glu
    500                 505                 510 taa ggaaaactgc ctgggttagg caaatagcta atgagtattt ttttgatggc           1885
aaccaaatgt agaagaaaa aaaaaaaaaa agaaaaaaaa aagagaatat tatatctatg     1945
taattctatt aaaagctctg ttgagtgagc ggaataaata ctgttgaaga ggggattgtg    2005
tagagatctg tttactcaat ggcaaactca tctgggggag atccttccac tgtgggaagc    2065
tcctggatag cctttgcatc ggggttcaag aagaccattg tgaacagccc ttga          2119
```

<210> SEQ ID NO 4
<211> LENGTH: 514
<212> TYPE: PRT
<213> ORGANISM: Yarrowia lipolytica

<400> SEQUENCE: 4

```
Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45
```

```
Pro Thr Phe Leu Thr Ile Phe Met Leu Cys Cys Ala Ile Pro Leu Leu
 50                  55                  60

Trp Pro Phe Val Ile Ala Tyr Val Val Tyr Ala Val Lys Asp Asp Ser
 65                  70                  75                  80

Pro Ser Asn Gly Gly Val Val Lys Arg Tyr Ser Pro Ile Ser Arg Asn
                 85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
            115                 120                 125

Gln Glu Tyr His Leu Ile Ala Glu Arg Tyr Trp Pro Gln Asn Lys Tyr
            130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Pro Gly Ser Gln Pro Asp
            180                 185                 190

Lys Trp Ile Asn His Asp Ser Arg Tyr Ser Arg Gly Glu Ser Ser Gly
            195                 200                 205

Ser Asn Gly His Ala Ser Gly Ser Glu Leu Asn Gly Asn Gly Asn Asn
210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
            275                 280                 285

Gly Met Gly Ala Phe Gly Gly Ile Ala Thr Glu Gly Ala Gly Trp Ser
290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
            355                 360                 365

Gly Val Met Asp Leu Val Leu Leu Lys Arg Lys Gly Phe Val Arg Leu
            370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
            435                 440                 445

Tyr Arg Arg Pro Val Asn Ile Val Val Gly Ser Pro Ile Asp Leu Pro
450                 455                 460
```

```
Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu

<210> SEQ ID NO 5
<211> LENGTH: 1380
<212> TYPE: DNA
<213> ORGANISM: Yarrowia lipolytica
<220> FEATURE:
<221> NAME/KEY: misc_feature
<223> OTHER INFORMATION: DGAT2

<400> SEQUENCE: 5
atgctatgct gcgcaattcc actgctctgg ccatttgtga ttgcgtatgt agtgtacgct      60
gttaaagacg actccccgtc caacggagga gtggtcaagc gatactcgcc tatttcaaga     120
aacttcttca tctggaagct ctttggccgc tacttcccca taactctgca caagacggtg     180
gatctggagc ccacgcacac atactaccct ctggacgtcc aggagtatca cctgattgct     240
gagagatact ggccgcagaa caagtacctc cgagcaatca tctccaccat cgagtacttt     300
ctgcccgcct tcatgaaacg gtctctttct atcaacgagc aggagcagcc tgccgagcga     360
gatcctctcc tgtctcccgt ttctcccagc tctccgggtt ctcaacctga caagtggatt     420
aaccacgaca gcagatatag ccgtggagaa tcatctggct ccaacggcca cgcctcgggc     480
tccgaactta acggcaacgg caacaatggc accactaacc gacgaccttt gtcgtccgcc     540
tctgctggct ccactgcatc tgattccacg cttcttaacg ggtccctcaa ctcctacgcc     600
aaccagatca ttggcgaaaa cgacccacag ctgtcgccca caaaactcaa gcccactggc     660
agaaaataca tcttcggcta ccaccccac ggcattatcg gcatgggagc ctttggtgga     720
attgccaccg agggagctgg atggtccaag ctctttccgg gcatccctgt ttctcttatg     780
actctcacca caacttccg agtgcctctc tacagagagt acctcatgag tctgggagtc     840
gcttctgtct ccaagaagtc ctgcaaggcc ctcctcaagc gaaaccagtc tatctgcatt     900
gtcgttggtg gagcacagga aagtcttctg gccagacccg tgtcatgga cctggtgcta     960 ctcaagcgaa agggttttgt tcgacttggt atggaggtcg gaaatgtcgc ccttgttccc    1020
atcatggcct ttggtgagaa cgacctctat gaccaggtta gcaacgacaa gtcgtccaag    1080
ctgtaccgat ccagcagtt tgtcaagaac ttccttggat tcaccttcc tttgatgcat    1140 gcccgaggcg tcttcaacta cgatgtcggt cttgtcccct acaggcgacc cgtcaacatt    1200
gtggttggtt cccccattga cttgccttat ctcccacacc ccaccgacga agaagtgtcc    1260
gaataccacg accgatacat cgccgagctg cagcgaatct acaacgagca caaggatgaa    1320
tatttcatcg attggaccga ggagggcaaa ggagccccag agttccgaat gattgagtaa    1380

<210> SEQ ID NO 6
<211> LENGTH: 459
<212> TYPE: PRT
<213> ORGANISM: Yarrowia lipolytica

<400> SEQUENCE: 6

Met Leu Cys Cys Ala Ile Pro Leu Leu Trp Pro Phe Val Ile Ala Tyr
1               5                   10                  15
```

```
Val Val Tyr Ala Val Lys Asp Asp Ser Pro Ser Asn Gly Gly Val Val
             20                  25                  30

Lys Arg Tyr Ser Pro Ile Ser Arg Asn Phe Phe Ile Trp Lys Leu Phe
         35                  40                  45

Gly Arg Tyr Phe Pro Ile Thr Leu His Lys Thr Val Asp Leu Glu Pro
     50                  55                  60

Thr His Thr Tyr Tyr Pro Leu Asp Val Gln Glu Tyr His Leu Ile Ala
 65                  70                  75                  80

Glu Arg Tyr Trp Pro Gln Asn Lys Tyr Leu Arg Ala Ile Ile Ser Thr
                 85                  90                  95

Ile Glu Tyr Phe Leu Pro Ala Phe Met Lys Arg Ser Leu Ser Ile Asn
            100                 105                 110

Glu Gln Glu Gln Pro Ala Glu Arg Asp Pro Leu Leu Ser Pro Val Ser
            115                 120                 125

Pro Ser Ser Pro Gly Ser Gln Pro Asp Lys Trp Ile Asn His Asp Ser
130                 135                 140

Arg Tyr Ser Arg Gly Glu Ser Ser Gly Ser Asn Gly His Ala Ser Gly
145                 150                 155                 160

Ser Glu Leu Asn Gly Asn Gly Asn Gly Thr Thr Asn Arg Arg Pro
                165                 170                 175

Leu Ser Ser Ala Ser Ala Gly Ser Thr Ala Ser Asp Ser Thr Leu Leu
            180                 185                 190

Asn Gly Ser Leu Asn Ser Tyr Ala Asn Gln Ile Ile Gly Glu Asn Asp
        195                 200                 205

Pro Gln Leu Ser Pro Thr Lys Leu Lys Pro Thr Gly Arg Lys Tyr Ile
    210                 215                 220

Phe Gly Tyr His Pro His Gly Ile Ile Gly Met Gly Ala Phe Gly Gly
225                 230                 235                 240

Ile Ala Thr Glu Gly Ala Gly Trp Ser Lys Leu Phe Pro Gly Ile Pro
                245                 250                 255

Val Ser Leu Met Thr Leu Thr Asn Asn Phe Arg Val Pro Leu Tyr Arg
            260                 265                 270

Glu Tyr Leu Met Ser Leu Gly Val Ala Ser Val Ser Lys Lys Ser Cys
        275                 280                 285

Lys Ala Leu Leu Lys Arg Asn Gln Ser Ile Cys Ile Val Val Gly Gly
    290                 295                 300

Ala Gln Glu Ser Leu Leu Ala Arg Pro Gly Val Met Asp Leu Val Leu
305                 310                 315                 320

Leu Lys Arg Lys Gly Phe Val Arg Leu Gly Met Glu Val Gly Asn Val
                325                 330                 335

Ala Leu Val Pro Ile Met Ala Phe Gly Glu Asn Asp Leu Tyr Asp Gln
            340                 345                 350

Val Ser Asn Asp Lys Ser Ser Lys Leu Tyr Arg Phe Gln Gln Phe Val
        355                 360                 365

Lys Asn Phe Leu Gly Phe Thr Leu Pro Leu Met His Ala Arg Gly Val
    370                 375                 380

Phe Asn Tyr Asp Val Gly Leu Val Pro Tyr Arg Arg Pro Val Asn Ile
385                 390                 395                 400

Val Val Gly Ser Pro Ile Asp Leu Pro Tyr Leu Pro His Pro Thr Asp
                405                 410                 415

Glu Glu Val Ser Glu Tyr His Asp Arg Tyr Ile Ala Glu Leu Gln Arg
            420                 425                 430

Ile Tyr Asn Glu His Lys Asp Glu Tyr Phe Ile Asp Trp Thr Glu Glu
```

```
                 435                 440                 445
Gly Lys Gly Ala Pro Glu Phe Arg Met Ile Glu
    450                 455

<210> SEQ ID NO 7
<211> LENGTH: 1068
<212> TYPE: DNA
<213> ORGANISM: Yarrowia lipolytica
<220> FEATURE:
<221> NAME/KEY: misc_feature
<223> OTHER INFORMATION: DGAT2

<400> SEQUENCE: 7
atgaaacggt ctctttctat caacgagcag gagcagcctg ccgagcgaga tcctctcctg      60
tctcccgttt ctcccagctc tccgggttct caacctgaca gtggattaa ccacgacagc     120 agatatagcc gtggagaatc atctggctcc aacggccacg cctcgggctc gaacttaac     180 ggcaacggca acaatggcac cactaaccga cgacctttgt cgtccgcctc tgctggctcc     240
actgcatctg attccacgct tcttaacggg tccctcaact cctacgccaa ccagatcatt     300
ggcgaaaacg acccacagct gtcgcccaca aaactcaagc ccactggcag aaaatacatc     360
ttcggctacc accccacgg cattatcggc atgggagcct tggtggaat tgccaccgag      420 ggagctggat ggtccaagct cttccgggc atccctgttt ctcttatgac tctcaccaac      480
aacttccgag tgcctctcta cagagagtac ctcatgagtc tgggagtcgc ttctgtctcc      540
aagaagtcct gcaaggccct cctcaagcga accagtcta tctgcattgt cgttggtgga      600
gcacaggaaa gtcttctggc cagacccggt gtcatggacc tggtgctact caagcgaaag     660
ggttttgttc gacttggtat ggaggtcgga aatgtcgccc ttgttcccat catggccttt     720
ggtgagaacg acctctatga ccaggttagc aacgacaagt cgtccaagct gtaccgattc     780
cagcagtttg tcaagaactt ccttggattc acccttcctt tgatgcatgc ccgaggcgtc     840
ttcaactacg atgtcggtct tgtcccctac aggcgacccg tcaacattgt ggttggttcc      900
cccattgact gccttatct cccacacccc accgacgaag aagtgtccga ataccacgac      960
cgatacatcg ccgagctgca gcgaatctac aacgagcaca aggatgaata tttcatcgat    1020
tggaccgagg agggcaaagg agccccagag ttccgaatga ttgagtaa                 1068

<210> SEQ ID NO 8
<211> LENGTH: 355
<212> TYPE: PRT
<213> ORGANISM: Yarrowia lipolytica

<400> SEQUENCE: 8

Met Lys Arg Ser Leu Ser Ile Asn Glu Gln Glu Gln Pro Ala Glu Arg
1               5                   10                  15

Asp Pro Leu Leu Ser Pro Val Ser Pro Ser Ser Pro Gly Ser Gln Pro
            20                  25                  30

Asp Lys Trp Ile Asn His Asp Ser Arg Tyr Ser Arg Gly Glu Ser Ser
        35                  40                  45

Gly Ser Asn Gly His Ala Ser Gly Ser Glu Leu Asn Gly Asn Gly Asn
    50                  55                  60

Asn Gly Thr Thr Asn Arg Arg Pro Leu Ser Ser Ala Ser Ala Gly Ser
65                  70                  75                  80

Thr Ala Ser Asp Ser Thr Leu Leu Asn Gly Ser Leu Asn Ser Tyr Ala
                85                  90                  95

Asn Gln Ile Ile Gly Glu Asn Asp Pro Gln Leu Ser Pro Thr Lys Leu
```

```
                    100                 105                 110
Lys Pro Thr Gly Arg Lys Tyr Ile Phe Gly Tyr His Pro His Gly Ile
            115                 120                 125
Ile Gly Met Gly Ala Phe Gly Gly Ile Ala Thr Glu Gly Ala Gly Trp
        130                 135                 140
Ser Lys Leu Phe Pro Gly Ile Pro Val Ser Leu Met Thr Leu Thr Asn
145                 150                 155                 160
Asn Phe Arg Val Pro Leu Tyr Arg Glu Tyr Leu Met Ser Leu Gly Val
                165                 170                 175
Ala Ser Val Ser Lys Ser Cys Lys Ala Leu Leu Lys Arg Asn Gln
            180                 185                 190
Ser Ile Cys Ile Val Val Gly Gly Ala Gln Glu Ser Leu Leu Ala Arg
            195                 200                 205
Pro Gly Val Met Asp Leu Val Leu Leu Lys Arg Lys Gly Phe Val Arg
        210                 215                 220
Leu Gly Met Glu Val Gly Asn Val Ala Leu Val Pro Ile Met Ala Phe
225                 230                 235                 240
Gly Glu Asn Asp Leu Tyr Asp Gln Val Ser Asn Asp Lys Ser Ser Lys
                245                 250                 255
Leu Tyr Arg Phe Gln Gln Phe Val Lys Asn Phe Leu Gly Phe Thr Leu
            260                 265                 270
Pro Leu Met His Ala Arg Gly Val Phe Asn Tyr Asp Val Gly Leu Val
        275                 280                 285
Pro Tyr Arg Arg Pro Val Asn Ile Val Val Gly Ser Pro Ile Asp Leu
        290                 295                 300
Pro Tyr Leu Pro His Pro Thr Asp Glu Glu Val Ser Glu Tyr His Asp
305                 310                 315                 320
Arg Tyr Ile Ala Glu Leu Gln Arg Ile Tyr Asn Glu His Lys Asp Glu
                325                 330                 335
Tyr Phe Ile Asp Trp Thr Glu Glu Gly Lys Gly Ala Pro Glu Phe Arg
            340                 345                 350
Met Ile Glu
        355

<210> SEQ ID NO 9
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 9
aagcagtggt atcaacgcag agtggccatt acggccggg                          39

<210> SEQ ID NO 10
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t
```

<400> SEQUENCE: 10
attctagagg ccgaggcggc cgacatgttt tttttttttt tttttttttt tttttttvn    59

<210> SEQ ID NO 11
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 11
aagcagtggt atcaacgcag agt                                           23

<210> SEQ ID NO 12
<211> LENGTH: 21
<212> TYPE: DNA
<213> ORGANISM: Artificial Sequence
<220> FEATURE:
<223> OTHER INFORMATION: Primer MDGAT-FN1
<220> FEATURE:
<221> NAME/KEY: misc_feature
<222> LOCATION: (16)..(16)
<223> OTHER INFORMATION: n is a, c, g, or t

<400> SEQUENCE: 12
gaactacatc ttyggntayc a                                             21

<210> SEQ ID NO 13
<211> LENGTH: 7
<212> TYPE: PRT
<213> ORGANISM: Artificial Sequence
<220> FEATURE:
<223> OTHER INFORMATION: Primer MDGAT-FN1

<400> SEQUENCE: 13

Asn Tyr Ile Phe Gly Tyr His
1               5

<210> SEQ ID NO 14
<211> LENGTH: 20
<212> TYPE: DNA
<213> ORGANISM: Artificial Sequence
<220> FEATURE:
<223> OTHER INFORMATION: Primer MDGAT-RN1
<220> FEATURE:
<221> NAME/KEY: misc_feature
<222> LOCATION: (15)..(15)
<223> OTHER INFORMATION: n is a, c, g, or t

<400> SEQUENCE: 14
tacagctcrt tytcnccraa                                               20

<210> SEQ ID NO 15
<211> LENGTH: 7
<212> TYPE: PRT
<213> ORGANISM: Artificial Sequence
<220> FEATURE:
<223> OTHER INFORMATION: Primer MDGAT-RN1

<400> SEQUENCE: 15

Phe Gly Glu Asn Glu Leu Tyr
1               5

<210> SEQ ID NO 16
<211> LENGTH: 20
<212> TYPE: DNA

<210> SEQ ID NO 16 (implied continuation)
<213> ORGANISM: Artificial Sequence
<220> FEATURE:
<223> OTHER INFORMATION: Primer MDGAT-RN2
<220> FEATURE:
<221> NAME/KEY: misc_feature
<222> LOCATION: (18)..(18)
<223> OTHER INFORMATION: n is a, c, g, or t

<400> SEQUENCE: 16
ccaaagtcrt arttraanac                                               20

<210> SEQ ID NO 17
<211> LENGTH: 7
<212> TYPE: PRT
<213> ORGANISM: Artificial Sequence
<220> FEATURE:
<223> OTHER INFORMATION: Primer MDGAT-RN2

<400> SEQUENCE: 17

Val Phe Asn Tyr Asp Phe Gly
1               5

<210> SEQ ID NO 18
<211> LENGTH: 370
<212> TYPE: DNA
<213> ORGANISM: M alpina

<400> SEQUENCE: 18
gaactacatc ttcgggtatc acccacacgg aatcatttcc ttgggtgccc tctgcgcctt     60
tgggaccgag ggccttcatt tctccaaacg cttcccgggt atcaagcctc atctgctcac    120
cattcacgcc aactttcaga tcccactcta tcgcgatatg atcatggccc acggctgtgc    180
ttccgtgtcg agggcctctt gtgaacacat cctgcggtct ggcgaaggat cctcggtcgt    240
gatcgttgtc gggggtgcac aagaaagttt gtcgactcaa cctggcacgt taaatctgac    300
actcaagaaa agactgggat tttgcaagct ggcctttgtc aatggcgcaa gtctggtacc    360
tacgttggcc                                                          370

<210> SEQ ID NO 19
<211> LENGTH: 654
<212> TYPE: DNA
<213> ORGANISM: M alpina
<220> FEATURE:
<221> NAME/KEY: misc_feature
<222> LOCATION: (370)..(370)
<223> OTHER INFORMATION: n is a, c, g, or t

<400> SEQUENCE: 19
gaactacatc tttgggtatc acccacacgg aatcatttcc ttgggtgccc tctgcgcctt     60
tgggaccgag ggccttcatt tctccaaacg cttcccgggt atcaagcctc atctgctcac    120
cattcacgcc aactttcaga tcccactcta tcgcgatatg atcatggccc acggctgtgc    180
ttccgtgtcg agggcctctt gtgaacacat cctgcggtct ggcgaaggat cctcggtcgt    240
gatcgttgtc gggggtgcac aagaaagttt gtcgactcaa cctggcacgt taaatctgac    300
actcaagaaa agactgggat tttgcaagct ggcccttgtc aatgggtaag gagacggata    360
tctcctgtgn attattttt tttttttttt tttttttttt tgccggccct tcaaggggc      420 taatgcgtcg ttaaagagga atatcttgcg tctgactctt gctacagata cacgcaaacg    480
aacacggtga actgatactc catggctttc tacgatgctg ttagcgcaag tctggtacct    540
acgttggcct ttggtgagaa cgagctctat gaggtgtacc acaccaagcc cacaagcctg    600
atatacaagc tccagcagtt gactaaacgc acgatcggct tcacaatgcc cgtc        654

<210> SEQ ID NO 20
<211> LENGTH: 179
<212> TYPE: DNA
<213> ORGANISM: M alpina
<220> FEATURE:
<221> NAME/KEY: misc_feature
<222> LOCATION: (25)..(25)
<223> OTHER INFORMATION: n is a, c, g, or t

<400> SEQUENCE: 20
gtaaggagac ggatatctcc tgtgnattat tttttttttt tttttttttt tttttttgccg    60 gcccttcaaa ggggctaatg cgtcgttaaa gaggaatatc ttgcgtctga ctcttgctac    120
agatacacgc aaacgaacac ggtgaactga tactccatgg ctttctacga tgctgttag    179

<210> SEQ ID NO 21
<211> LENGTH: 37
<212> TYPE: DNA
<213> ORGANISM: Artificial Sequence
<220> FEATURE:
<223> OTHER INFORMATION: Adapter primer

<400> SEQUENCE: 21
ggccacgcgt cgactagtac ttttttttttt ttttttt        37

<210> SEQ ID NO 22
<211> LENGTH: 22
<212> TYPE: DNA
<213> ORGANISM: Artificial Sequence
<220> FEATURE:
<223> OTHER INFORMATION: Primer MDGAT-3-1

<400> SEQUENCE: 22
ggcacgttaa atctgacact ca        22

<210> SEQ ID NO 23
<211> LENGTH: 49
<212> TYPE: DNA
<213> ORGANISM: Artificial Sequence
<220> FEATURE:
<223> OTHER INFORMATION: Primer UAP
<220> FEATURE:
<221> NAME/KEY: misc_feature
<222> LOCATION: (2)..(2)
<223> OTHER INFORMATION: N = uracil
<220> FEATURE:
<221> NAME/KEY: misc_feature
<222> LOCATION: (5)..(5)
<223> OTHER INFORMATION: N = uracil
<220> FEATURE:
<221> NAME/KEY: misc_feature
<222> LOCATION: (8)..(8)
<223> OTHER INFORMATION: N = uracil
<220> FEATURE:
<221> NAME/KEY: misc_feature
<222> LOCATION: (11)..(11)
<223> OTHER INFORMATION: N = uracil

<400> SEQUENCE: 23
cnacnacnac naggccacgc gtcgactagt acttttttttt tttttttttt        49

<210> SEQ ID NO 24
<211> LENGTH: 20
<212> TYPE: DNA
<213> ORGANISM: Artificial Sequence
<220> FEATURE:

<223> OTHER INFORMATION: Primer MDGAT-3-2

<400> SEQUENCE: 24
gactgggatt ttgcaagctg                                              20

<210> SEQ ID NO 25
<211> LENGTH: 19
<212> TYPE: DNA
<213> ORGANISM: Artificial Sequence
<220> FEATURE:
<223> OTHER INFORMATION: Primer MDGAT-3-3

<400> SEQUENCE: 25
gcctttgtca atgcgcaag                                               19

<210> SEQ ID NO 26
<211> LENGTH: 455
<212> TYPE: DNA
<213> ORGANISM: M alpina
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t

<400> SEQUENCE: 26
ttgtcaatgg cgcaagtctg gtacctacgt tggcctttgg tgagaacgag ctctatgagg    60
tgtaccacac caagcccaca agcctgatat acaagctcca gcagttgact aaacgcacga   120
tcggcttcac aatgcccgtg ttcaacggac gaggaatctt caattatgag tttggactgc   180
tgccaaggag gaagcctgtc tatatcgtta taggaaaccc cattcatgta gacaaggtcg   240
agaacccaac gattgaacag atgcagaaac tgcagtcaat ttacattgat gaggtgctaa   300
acatttggga aagatacaag gacaagtatg ccgcaggacg aactcaggaa ctgtgcatca   360
tcgaatagga gggcttggcc gatggcaacc caaataataa aaaaaaaaga aagnggtgta   420
gncttgctcc aannaaaaaa aaaaaaaaaa aaaaa                              455

<210> SEQ ID NO 27
<211> LENGTH: 44
<212> TYPE: DNA
<213> ORGANISM: Artificial Sequence
<220> FEATURE:
<223> OTHER INFORMATION: Genome Walker adaptor-1

<400> SEQUENCE: 27
gtaatacgac tatagggcac gcgtggtcga cggcccgggc tggt                    44

<210> SEQ ID NO 28
<211> LENGTH: 8
<212> TYPE: DNA
<213> ORGANISM: Artificial Sequence
<220> FEATURE:
<223> OTHER INFORMATION: Genome Walker adaptor-2
<220> FEATURE:
<221> NAME/KEY: misc_feature
<222> LOCATION: (1)..(1)
<223> OTHER INFORMATION: 5' end is associated with a -PO4 group
<220> FEATURE:
<221> NAME/KEY: misc_feature

```
<222> LOCATION: (8)..(8)
<223> OTHER INFORMATION: 3' end is associated with a -H2N group

<400> SEQUENCE: 28 accagccc                                                                    8

<210> SEQ ID NO 29
<211> LENGTH: 22
<212> TYPE: DNA
<213> ORGANISM: Artificial Sequence
<220> FEATURE:
<223> OTHER INFORMATION: Primer AP1

<400> SEQUENCE: 29
gtaatacgac tcactatagg gc                                                    22

<210> SEQ ID NO 30
<211> LENGTH: 19
<212> TYPE: DNA
<213> ORGANISM: Artificial Sequence
<220> FEATURE:
<223> OTHER INFORMATION: Primer AP2

<400> SEQUENCE: 30
actatagggc acgcgtggt                                                        19

<210> SEQ ID NO 31
<211> LENGTH: 674
<212> TYPE: DNA
<213> ORGANISM: M alpina
<220> FEATURE:
<221> NAME/KEY: misc_feature
<222> LOCATION: (582)..(582)
<223> OTHER INFORMATION: n is a, c, g, or t

<400> SEQUENCE: 31
gactgggatt ttgcaagctg gcccttgtca atgggtaagg agacggatat ctcctgtgta          60
ttattttttt tttttttttt tttttttttt gccgtccctt caaagggcct aatgcgtcgt         120
taaagaggaa tatcttgcgt ctgactcttg ctacagatac acgcaaacga acacggtgaa         180
ctgatactcc atggctttct acgatgctgt tagcgcaagt ctggtaccta cgttggcctt         240
tggtgagaac gagctctatg aggtgtacca ccaagcccc acaagcctga tatacaagct         300
ccagcagttg actaaacgca cgatcggctt cacaatgccc gtgttcaacg gacgaggaat         360
cttcaattgt gagttctctg acttggttcc caaacacact ttctgttggg tttttttttc         420
tcttcaaagt gatcatataa taccacttac taatctccct atttcctttt tttttttttt         480 ttttggtcc ccactgtaaa tgaatttgga ctgctgccaa ggaggaagcc tgtctatatc         540
gttataggaa accccattca tgtagacaag gtcgagaacc cnacgattga acagatgcag         600
aaactgcagt caatttacat tgatgaggtg ctaaacattt gggaaagata caaggacaag         660
tatgccgcag gacg                                                           674

<210> SEQ ID NO 32
<211> LENGTH: 184
<212> TYPE: DNA
<213> ORGANISM: M alpina

<400> SEQUENCE: 32
gtaccgaaac caacatggag gacggagagt cttttgagcg cagattttct ttttcctttt          60
aatcatgttc gcacgtcccc ccccccagct ttcttctcgt ctctaactgt aaccaacttt         120
```

```
ttgtcgaaat gcctgttgca tatttggaaa catactgatt tttttttttt tttcctactc    180
aaag                                                                 184

<210> SEQ ID NO 33
<211> LENGTH: 131
<212> TYPE: DNA
<213> ORGANISM: M alpina

<400> SEQUENCE: 33
gtgagttctc tgacttggtt cccaaacaca ctttctgttg ggttttttttt tctcttcaaa    60 gtgatcatat aataccactt actaatctcc ctatttcctt tttttttttt ttttttttggt  120 ccccactgta a                                                         131

<210> SEQ ID NO 34
<211> LENGTH: 22
<212> TYPE: DNA
<213> ORGANISM: Artificial Sequence
<220> FEATURE:
<223> OTHER INFORMATION: Primer MDGAT-5-1

<400> SEQUENCE: 34
ggaagcgttt ggagaaatga ag                                              22

<210> SEQ ID NO 35
<211> LENGTH: 22
<212> TYPE: DNA
<213> ORGANISM: Artificial Sequence
<220> FEATURE:
<223> OTHER INFORMATION: Primer MDGAT-5-2

<400> SEQUENCE: 35
aatgattccg tgtgggtgat ac                                              22

<210> SEQ ID NO 36
<211> LENGTH: 1261
<212> TYPE: DNA
<213> ORGANISM: M alpina

<400> SEQUENCE: 36
actatagggc acgcgtggtc gacggcccgg gctggtctga agacgtggat gtgtactctc    60
ttacgggcaa acatatgcct gatacaatgg taccggagtc gtcggaaaga cctagcatcg   120
agataagaga attatgcaag atatgacagc acagggatga gtgctttgtt gcgtgcgatg   180
tgcatgagtg tgtctgtgta ggcggcccta tgtgtggtgc tgcactcatg tgtatgatgc   240
gcatgtagga ggaaggatgg gcgcaggtcg cttcttttcc ttgtgtccgc caggcacaca   300
caatgcgcac aggcacccaa ttgggttcat gcgaggcata ccgtgcacct ctctgcgctt   360
ctctctccaa gcgacatgcg tccaaacgca agctcagct ttgggtttaa tcgtcccgta    420
gtgcatcggc gtgccttcgc gctcacacac tcgcacatct cgccctttgt tgccctttt    480 ccttcttctc tcactctgtc ctgtctataa agccctgca acactgtcct ctctcgcctc   540
tccactctcc acagttttca ctcctcgact cattcctttt tcacacctca ccgctctcca   600
ttgactccat tgacacgtcg cattcgtctc ctggtgcacg actcgtttgc ttttcacacc   660
aagctcgctg tgttgacaaa cagcaactcc actctcctct caaccatc attgctcccc    720 tgttcctctg ttcctctctc gctcagaatg ccgctctttg cgcctttacg gatgcccgtc   780
aagcgtcgta tgcagacagg agctgtccta tactggattg cggggatgat ttactgcatt   840
ggcatctttg ccttcctctg cacgttcaag atccttcgac ccttgatcat catctatgtc   900
```

-continued

```
ctgtgggcct acatgctcga ccgagcacca gagcggggtg cacgcacagt ccaatggtat    960
tgtaactgga tcggatggaa acactttgca cagtactttc ctatgaccct tgtcaaggta   1020
ccgaaaccaa catggaggac ggagagtctt tgagcgcag attttctttt tccttttaat   1080
catgttcgca cgtccccccc cccagctttc ttctcgtctc taactgtaac caactttttg   1140
tcgaaatgcc tgttgcatat tggaaacat actgatttt tttttttttt cctactcaaa   1200
ggagggagag ctggacccat ccaagaacta catctttggg tatcacccac acggaatcat   1260
t                                                                   1261
```

<210> SEQ ID NO 37
<211> LENGTH: 2299
<212> TYPE: DNA
<213> ORGANISM: M alpina
<220> FEATURE:
<221> NAME/KEY: misc_feature
<222> LOCATION: (748)..(751)
<223> OTHER INFORMATION: Translation initiation codon 'ATG'
<220> FEATURE:
<221> NAME/KEY: Intron
<222> LOCATION: (1018)..(1201)
<220> FEATURE:
<221> NAME/KEY: Intron
<222> LOCATION: (1570)..(1748)
<220> FEATURE:
<221> NAME/KEY: Intron
<222> LOCATION: (1903)..(2034)
<220> FEATURE:
<221> NAME/KEY: misc_feature
<222> LOCATION: (2117)..(2117)
<223> OTHER INFORMATION: n is a, c, g, or t
<220> FEATURE:
<221> NAME/KEY: misc_feature
<222> LOCATION: (2235)..(2237)
<223> OTHER INFORMATION: Stop codon 'TAG'
<220> FEATURE:
<221> NAME/KEY: misc_feature
<222> LOCATION: (2283)..(2283)
<223> OTHER INFORMATION: n is a, c, g, or t
<220> FEATURE:
<221> NAME/KEY: misc_feature
<222> LOCATION: (2291)..(2291)
<223> OTHER INFORMATION: n is a, c, g, or t

<400> SEQUENCE: 37

```
actatagggc acgcgtggtc gacggcccgg gctggtctga agacgtggat gtgtactctc     60
ttacgggcaa acatatgcct gatacaatgg taccggagtc gtcggaaaga cctagcatcg    120
agataagaga attatgcaag atatgacagc acagggatga gtgctttgtt gcgtgcgatg    180
tgcatgagtg tgtctgtgta ggcggcccta tgtgtggtgc tgcactcatg tgtatgatgc    240
gcatgtagga ggaaggatgg gcgcaggtcg cttcttttcc ttgtgtccgc caggcacaca    300
caatgcgcac aggcacccaa ttgggttcat gcgaggcata ccgtgcacct ctctgcgctt    360
ctctctccaa gcgacatgcg tccaaacgca agctcagct ttgggtttaa tcgtcccgta    420
gtgcatcggc gtgccttcgc gctcacacac tcgcacatct cgccctttgt tgccctttt    480 ccttcttctc tcactctgtc ctgtctataa agccctgca acactgtcct ctctcgcctc    540
tccactctcc acagttttca ctcctcgact cattcctttt tcacacctca ccgctctcca    600
ttgactccat tgcacgtcg cattcgtctc tggtgcacg actcgtttgc ttttcacacc    660
aagctcgctg tgttgacaaa cagcaactcc actctcctct caacaccatc attgctcccc    720
tgttcctctg ttcctctctc gctcagaatg ccgtctttg cgcctttacg gatgcccgtc    780
aagcgtcgta tgcagacagg agctgtccta tactggattg cggggatgat ttactgcatt    840
```

```
ggcatctttg ccttcctctg cacgttcaag atccttcgac ccttgatcat catctatgtc     900
ctgtgggcct acatgctcga ccgagcacca gagcggggtg cacgcacagt ccaatggtat     960
tgtaactgga tcggatggaa acactttgca cagtactttc ctatgaccct tgtcaaggta    1020
ccgaaaccaa catggaggac ggagagtctt ttgagcgcag atttctcttt tcctttaat     1080
catgttcgca cgtcccccccc cccagctttc ttctcgtctc taactgtaac caactttttg    1140
tcgaaatgcc tgttgcatat ttggaaacat actgattttt tttttttttt cctactcaaa    1200
ggagggagag ctggacccat ccaagaacta catctttggg tatcacccac acggaatcat    1260
tttcttgggt gccctctgcg cctttgggac cgagggcctt catttctcca aacgcttccc    1320
gggtatcaag cctcatctgc tcaccattca cgccaacttt cagatcccac tctatcgcga    1380
tatgatcatg gcccacggct gtgcttccgt gtcgagggcc tcttgtgaac acatcctgcg    1440
gtctggcgaa ggatcctcgg tcgtgatcgt tgtcggggt gcacaagaaa gtttgtcgac     1500
tcaacctggc acgttaaatc tgacactcaa gaaaagactg ggattttgca agctggccct    1560
tgtcaatggg taaggagacg gatatctcct gtgtattatt ttttttttt tttttttttt    1620
tttttgccgk cccttcaaag gggctaatgc gtcgttaaag aggaatatct tgcgtctgac    1680
tcttgctaca gatacacgca aacgaacacg gtgaactgat actccatggc tttctacgat    1740
gctgttagcg caagtctggt acctacgttg gcctttggtg agaacgagct ctatgaggtg    1800
taccacacca agcccacaag cctgatatac aagctccagc agttgactaa acgcacgatc    1860
ggcttcacaa tgcccgtstt caacggacga ggaatcttca attgtgagtt ctctgacttg    1920
gttcccaaac acactttctg ttgggttttt ttttctcttc aaagtgatca tataatacca    1980
cttactaatc tccctatttc cttttttttt tttttttttt ggtccccact gtaaatgart    2040
ttggactgct gccaaggagg aagcctgtct atatcgttat aggaaacccc attcatgtag    2100
acaaggtcga gaacccnacg attgaacaga tgcagaaact gcagtcaatt tacattgatg    2160
aggtgctaaa catttgggaa agatacaagg acaagtatgc cgcaggacga actcaggaac    2220
tgtgcatcat cgaataggag ggcttggccg atggcaaccc aaataataaa aaaaaagaa     2280
agnggtgtag ncttgctcc                                                  2299

<210> SEQ ID NO 38
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 38
taaccctcac taagggaac aaaagctgga gctccaccgc ggacacaata tctggtcaaa     60
tttcagtttc gttacataaa tcgttatgtc aaaggagtgt gggaggttaa gagaattatc    120
accggcaaac tatctgttaa ttgctaggta cctctagacg tccacccggg tcgcttggcg    180
gccgaagagg ccggaatctc gggccgcggt ggcggccgct tagttggtct tggacttctt    240
gggcttcttc aggtaggact ggacaaagaa gttgccgaac agagcgagca gggtgatcat    300
```

| | |
|---|---|
| gtacacgccg agcagctgga ccagagcctg agggtagtcg caggggaaga ggtagtcgta | 360 |
| cagggactgc accagcatag ccatgaactg ggtcatctgc agagtggtga tgtagggctt | 420 |
| gatgggcttg acgaagccga agccctgaga ggaaaagaag tagtaggcgt acatgacggt | 480 |
| gtggacgaag gagttgagga tgacggagaa gtaggcgtcg ccaccaggag cgtacttggc | 540 |
| aatagcccac cagatggcga agatggtggc atggtggtac acgtgcagga aggagacctg | 600 |
| gttgaacttc ttgcacagga tcatgatagc ggtgtccagg aactcgtagg ccttggagac | 660 |
| gtagaacacg tagacgattc gggacatgcc ctgagcgtgg gactcgttgc ccttctccat | 720 |
| gtcgttgccg aagaccttgt agccacccag gatagcctgt cggatggtct cgacgcacat | 780 |
| gtagagggac agtccgaaga ggaacaggtt gtggagcagc ttgatggtct tcagctcgaa | 840 |
| gggcttctcc atctgcttca tgatgggaat gccgaagagc agcatggcca tgtagccgac | 900 |
| ctcgaaggcg agcatggtgg agacgtccat catgggcaga ccgtcggtca gagcgtaggg | 960 |
| cttagctccg tccatccact ggtcgacacc ggtctcgact cgtccgacca cgtcgtccca | 1020 |
| gacagaggag ttggccatgg tgaatgattc ttatactcag aaggaaatgc ttaacgattt | 1080 |
| cgggtgtgag ttgacaagga gagagagaaa agaagaggaa aggtaattcg gggacggtgg | 1140 |
| tcttttatac ccttggctaa agtcccaacc acaaagcaaa aaaattttca gtagtctatt | 1200 |
| ttgcgtccgg catgggttac ccggatggcc agacaaagaa actagtacaa agtctgaaca | 1260 |
| agcgtagatt ccagactgca gtaccctacg cccttaacgg caagtgtggg aaccggggga | 1320 |
| ggtttgatat gtggggtgaa gggggctctc gccggggttg ggcccgctac tgggtcaatt | 1380 |
| tggggtcaat tggggcaatt ggggctgttt tttgggacac aaatacgccg ccaacccggt | 1440 |
| ctctcctgaa ttctgcatcg atcgaggaag aggacaagcg gctgcttctt aagtttgtga | 1500 |
| catcagtatc caaggcacca ttgcaaggat tcaaggcttt gaacccgtca tttgccattc | 1560 |
| gtaacgctgg tagacaggtt gatcggttcc ctacggcctc cacctgtgtc aatcttctca | 1620 |
| agctgcctga ctatcaggac attgatcaac ttcggaagaa acttttgtat gccattcgat | 1680 |
| cacatgctgg tttcgatttg tcttagagga acgcatatac agtaatcata gagaataaac | 1740 |
| gatattcatt tattaaagta gatagttgag gtagaagttg taaagagtga taaatagcgg | 1800 |
| ccgcgcctac ttaagcaacg ggcttgataa cagcgggggg ggtgcccacg ttgttgcggt | 1860 |
| tgcggaagaa cagaacaccc ttaccagcac cctcggcacc agcgctgggc tcaacccact | 1920 |
| ggcacatacg cgcactgcgg tacatggcgc ggatgaagcc acgaggacca tcctggacat | 1980 |
| cagcccggta gtgcttgccc atgatgggct taatggcctc ggtggcctcg tccgcgttgt | 2040 |
| agaaggggat gctgctgacg tagtggtgga ggacatgagt ctcgatgatg ccgtggagaa | 2100 |
| ggtggcggcc gatgaagccc atctcacggt caatggtagc agcggcacca cggacgaagt | 2160 |
| tccactcgtc gttggtgtag tggggaaggg tagggtcggt gtgctggagg aaggtgatgg | 2220 |
| caacgagcca gtggttaacc cagaggtagg gaacaaagta ccagatggcc atgttgtaga | 2280 |
| aaccgaactt ctgaacgagg aagtacagag cagtggccat cagaccgata ccaatatcgc | 2340 |
| tgaggacgat gagcttagcg tcactgttct cgtacagagg gctgcgggga tcgaagtggt | 2400 |
| taacaccacc gccgaggccg ttatgcttgc ccttgccgcg accctcacgc tggcgctcgt | 2460 |
| ggtagttgtg gccggtaaca ttggtgatga ggtagttggg ccagccnacg annnnctcag | 2520 |
| taagatgagc gagctcgtgg gtcatctttc cgagacgagt agcctgctgc tcgcgggttc | 2580 |
| ggggaacgaa gaccatgtca cgctccatgt tgccagtggc cttgtggtgc tttcggtggg | 2640 |
| agatttgcca gctgaagtag gggacaagga gggaagagtg aagaacccag ccagtaatgt | 2700 |

```
cgttgatgat gcgagaatcg gagaaagcac cgtgaccgca ctcatgggca ataacccaga   2760
gaccagtacc gaaaagaccc tgaagaacgg tgtacacggc ccacagacca gcgcgggcgg   2820
gggtggaggg gatatattcg ggggtcacaa agttgtacca gatgctgaaa gtggtagtca   2880
ggaggacaat gtcgcggagg atataaccgt atcccttgag agcggagcgc ttgaagcagt   2940
gcttagggat ggcattgtag atgtccttga tggtaaagtc gggaacctcg aactggttgc   3000
cgtaggtgtc gagcatgaca ccatactcgg acttgggctt ggcgatatca acctcggaca   3060
tggacgagag cgatgtggaa gaggccgagt ggcggggaga gtctgaagga gagacggcgg   3120
cagactcaga atccgtcaca gtagttgagg tgacggtgcg tctaagcgca gggttctgct   3180
tgggcagagc cgaagtggac gccatggaga gctgggttag tttgtgtaga gagtgtgtgt   3240
tgctagcgac tttcggattg tgtcattaca caaaacgcgt cgtctcgaca ctgatcttgt   3300
cgtggatact cacggctcgg acatcgtcgc cgacgatgac accggactt cgcttaagga    3360 cgtcagtaac aggcattgtg tgatgtgtag tttagatttc gaatctgtgg ggaaagaaag   3420 gaaaaagag actggcaacc gattgggaga gccactgttt atatataccc tagacaagcc    3480
ccccgcttgt aagatgttgg tcaatgtaaa ccagtattaa ggttggcaag tgcaggagaa   3540
gcaaggtgtg ggtaccgagc aatggaaatg tgcggaaggc aaaaaaatga ggccacggcc   3600
tattgtcggg gctatatcca gggggcgatt gaagtacact aacatgacat gtgtccacag   3660
accctcaatc tggcctgatg agccaaatcc atacgcgctt tcgcagctct aaaggctata   3720
acaagtcaca ccaccctgct cgacctcagc gccctcactt tttgttaaga caaactgtac   3780
acgctgttcc agcgttttct gcctgcacct ggtgggacat ttggtgcaac ctaaagtgct   3840
cggaacctct gtggtgtcca gatcagcgca gcagttccga ggtagttttg aggcccttag   3900
atgatgcaat ggtgtcagtc gctggatcac gagtcttaat ggcagtattc gttcttattt   3960
gtgccattga gccccgttat cctcgtatct tctacccccc atcccatccc tttgttggtg   4020
caaccctacc catttattgt tgggtgcagc ccaaccgacg tggagagctt ggcttggcca   4080
tataaaaagg ccccccccta gtggcaatgg cagaaagtca gctgtgagtt gttgaatttg   4140
tcatctaggc ggcctggccg tcttctccgg ggcaattgtt cctctatagt actgcgtaca   4200
ctgtttaaac agtgtacgca gatctgcgac gacggaattc ctgcagccca tctgcagaat   4260
tcaggagaga ccgggttggc ggcgtatttg tgtcccaaaa aacagcccca attgccccaa   4320
ttgaccccaa attgacccag tagcgggccc aaccccggcg agagcccct tcaccccaca    4380 tatcaaacct ccccggttc ccacacttgc cgttaagggc gtagggtact gcagtctgga    4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac cttcatccc gaggctgctt gggagactct cgccaacttc    4920
tacgttggag acattgacga gtccgaccga gacatcaaga acgatgactt tgccgctgag   4980
gtccgaaagc tgcgaaccct gttccagtct ctcggctact acgactcctc taaggcctac   5040
```

```
tacgccttca aggtctcctt caacctctgc atctggggac tgtccaccgt cattgtggcc    5100
aagtggggtc agacctccac cctcgccaac gtgctctctg ctgccctgct cggcctgttc    5160
tggcagcagt gcggatggct ggctcacgac tttctgcacc accaggtctt ccaggaccga    5220
ttctggggtg atctcttcgg agccttcctg ggaggtgtct gccagggctt ctcctcttcc    5280
tggtggaagg acaagcacaa cactcaccat gccgctccca acgtgcatgg cgaggatcct    5340
gacattgaca cccaccctct cctgacctgg tccgagcacg ctctggagat gttctccgac    5400
gtccccgatg aggagctgac ccgaatgtgg tctcgattca tggtcctgaa ccagacctgg    5460
ttctacttcc ccattctctc cttcgctcga ctgtcttggt gcctccagtc cattctcttt    5520
gtgctgccca acgtcaggc tcacaagccc tccggagctc gagtgcccat ctccctggtc    5580
gagcagctgt ccctcgccat gcactggacc tggtacctcg ctaccatgtt cctgttcatc    5640
aaggatcctg tcaacatgct cgtgtacttc ctggtgtctc aggctgtgtg cggaaacctg    5700
ctcgccatcg tgttctccct caaccacaac ggtatgcctg tgatctccaa ggaggaggct    5760
gtcgacatgg atttctttac caagcagatc atcactggtc gagatgtcca tcctggactg    5820
ttcgccaact ggttcaccgg tggcctgaac taccagatcg agcatcacct gttcccttcc    5880
atgcctcgac acaacttctc caagatccag cctgccgtcg agaccctgtg caagaagtac    5940
aacgtccgat accacaccac tggtatgatc gagggaactg ccgaggtctt ctcccgactg    6000
aacgaggtct ccaaggccac ctccaagatg ggcaaggctc agtaagcggc cgcatgagaa    6060
gataaatata taaatacatt gagatattaa atgcgctaga ttagagagcc tcatactgct    6120
cggagagaag ccaagacgag tactcaaagg ggattacacc atccatatcc acagacacaa    6180
gctggggaaa ggttctatat acactttccg gaataccgta gtttccgatg ttatcaatgg    6240
gggcagccag gatttcaggc acttcggtgt ctcggggtga atggcgttc ttggcctcca    6300 tcaagtcgta ccatgtcttc atttgcctgt caaagtaaaa cagaagcaga tgaagaatga    6360
acttgaagtg aaggaattta aattgccccg gagaagacgg ccaggccgcc tagatgacaa    6420
attcaacaac tcacagctga ctttctgcca ttgccactag gggggggcct ttttatatgg    6480
ccaagccaag ctctccacgt cggttgggct gcacccaaca ataaatgggt agggttgcac    6540
caacaaaggg atgggatggg gggtagaaga tacgaggata acgggggctca atggcacaaa    6600 taagaacgaa tactgccatt aagactcgtg atccagcgac tgacaccatt gcatcatcta    6660
agggcctcaa aactacctcg gaactgctgc gctgatctgg acaccacaga ggttccgagc    6720
actttaggtt gcaccaaatg tcccaccagg tgcaggcaga aaacgctgga acagcgtgta    6780
cagtttgtct taacaaaaag tgagggcgct gaggtcgagc agggtggtgt gacttgttat    6840 agccctttaga gctgcgaaag cgcgtatgga tttggctcat caggccagat tgagggtctg    6900
tggacacatg tcatgttagt gtacttcaat cgccccctgg atatagcccc gacaataggc    6960
cgtggcctca ttttttttgcc ttccgcacat ttccattgct cggtacccac accttgcttc    7020
tcctgcactt gccaacctta atactggttt acattgacca acatcttaca agcgggggc    7080 ttgtctaggg tatatataaa cagtggctct cccaatcggt tgccagtctc ttttttcctt    7140 tctttccccca cagattcgaa atctaaacta cacatcacac aatgcctgtt actgacgtcc    7200
ttaagcgaaa gtccggtgtc atcgtcggcg acgatgtccg agccgtgagt atccacgaca    7260
agatcagtgt cgagacgacg cgttttgtgt aatgacacaa tccgaaagtc gctagcaaca    7320
cacactctct acacaaacta acccagctct ccatggagtc cattgctccc ttcctgcct    7380 ccaagatgcc tcaggacctg ttcatggacc tcgccagcgc tatcggtgtc cgagctgctc    7440
```

-continued

```
cctacgtcga tccccaggag gctgccctgg ttgcccaggc cgagaagtac attcccacca    7500
ttgtccatca cactcgaggc ttcctggttg ccgtggagtc tccccaggct cgagagctgc    7560
ctctgatgaa cccccttccac gtgctcctga tcgtgctcgc ctacctggtc accgtgtttg    7620
tgggtatgca gatcatgaag aactttgaac gattcgaggt caagaccttc tccctcctgc    7680
acaacttctg tctggtctcc atctccgcct acatgtgcgg tggcatcctg tacgaggctt    7740
atcaggccaa ctatggactg tttgagaacg ctgccgatca caccttcaag ggtctcccta    7800
tggctaagat gatctggctc ttctacttct ccaagatcat ggagtttgtc gacaccatga    7860
tcatggtcct caagaagaac aaccgacaga tttcctttct gcacgtgtac caccactctt    7920
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga agaacgcca agctcgccaa gcaggccaag gctgacgctg    8280
ccaaggagaa ggccagaaag ctccagtaag cggccgcaag tgtggatggg gaagtgagtg    8340
cccggttctg tgtgcacaat tggcaatcca agatggatgg attcaacaca gggatatagc    8400
gagctacgtg gtggtgcgag gatatagcaa cggatattta tgtttgacac ttgagaatgt    8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatgggtt ttgatcatgc acacataagg tccgaccttta tcggcaagct    8700
caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
aggagggcat tttggtggtg aagaggagac tgaaataaat ttagtctgca gaactttta    8880
tcggaacctt atctggggca gtgaagtata tgttatggta atagttacga gttagttgaa    8940
cttatagata gactggacta tacgctatc ggtccaaatt agaaagaacg tcaatggctc    9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgacctttc cttgggaacc accaccgtca    9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660
gtttttccat aggctccgcc cccctgacga gcatcacaaa aatcgacgct caagtcagag    9720
gtggcgaaac ccgacaggac tataaagata ccaggcgttt ccccctggaa gctccctcgt    9780
```

-continued

```
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac   10020
tggtaacagg attagcagag cgaggtatgt aggcggtgct acagagttct gaagtggtg    10080 gcctaactac ggctacacta gaagaacagt atttggtatc tgcgctctgc tgaagccagt   10140
taccttcgga aaaagagttg gtagctcttg atccggcaaa caaaccaccg ctggtagcgg   10200
tggttttttt gtttgcaagc agcagattac gcgcagaaaa aaaggatctc aagaagatcc   10260
tttgatcttt tctacggggt ctgacgctca gtggaacgaa aactcacgtt aagggatttt   10320
ggtcatgaga ttatcaaaaa ggatcttcac ctagatcctt taaattaaa aatgaagttt    10380 taaatcaatc taaagtatat atgagtaaac ttggtctgac agttaccaat gcttaatcag   10440
tgaggcacct atctcagcga tctgtctatt tcgttcatcc atagttgcct gactccccgt   10500
cgtgtagata actacgatac gggagggctt accatctggc cccagtgctg caatgatacc   10560
gcgagaccca cgctcaccgg ctccagattt atcagcaata aaccagccag ccggaagggc   10620
cgagcgcaga agtggtcctg caactttatc cgcctccatc cagtctatta attgttgccg   10680
ggaagctaga gtaagtagtt cgccagttaa tagtttgcgc aacgttgttg ccattgctac   10740
aggcatcgtg gtgtcacgct cgtcgtttgg tatggcttca ttcagctccg gttcccaacg   10800
atcaaggcga gttacatgat cccccatgtt gtgcaaaaaa gcggttagct ccttcggtcc   10860
tccgatcgtt gtcagaagta agttggccgc agtgttatca ctcatggtta tggcagcact   10920
gcataattct cttactgtca tgccatccgt aagatgcttt tctgtgactg gtgagtactc   10980
aaccaagtca ttctgagaat agtgtatgcg gcgaccgagt tgctcttgcc cggcgtcaat   11040 acggataat accgcgccac atagcagaac tttaaaagtg ctcatcattg gaaaacgttc    11100
ttcggggcga aaactctcaa ggatcttacc gctgttgaga tccagttcga tgtaacccac   11160
tcgtgcaccc aactgatctt cagcatcttt tactttcacc agcgtttctg ggtgagcaaa   11220
aacaggaagg caaaatgccg caaaaaaggg aataagggcg acacggaaat gttgaatact   11280
catactcttc ctttttcaat attattgaag catttatcag ggttattgtc tcatgagcgg   11340
atacatattt gaatgtattt agaaaaataa acaaataggg gttccgcgca catttccccg   11400
aaaagtgcca cctgatgcgg tgtgaaatac cgcacagatg cgtaaggaga aaataccgca   11460
tcaggaaatt gtaagcgtta atattttgtt aaaattcgcg ttaaattttt gttaaatcag   11520 ctcattttt aaccaatagg ccgaaatcgg caaaatccct tataaatcaa agaatagac    11580 cgagataggg ttgagtgttg ttccagtttg gaacaagagt ccactattaa agaacgtgga   11640
ctccaacgtc aaagggcgaa aaaccgtcta tcagggcgat ggcccactac gtgaaccatc   11700
accctaatca agttttttgg ggtcgaggtg ccgtaaagca ctaaatcgga acctaaagg    11760 gagcccccga tttagagctt gacggggaaa gccggcgaac gtggcgagaa aggaagggaa   11820
gaaagcgaaa ggagcgggcg ctagggcgct ggcaagtgta gcggtcacgc tgcgcgtaac   11880
caccacaccc gccgcgctta atgcgccgct acagggcgcg tccattcgcc attcaggctg   11940
cgcaactgtt gggaagggcg atcggtgcgg gcctcttcgc tattacgcca gctggcgaaa   12000
gggggatgtg ctgcaaggcg attaagttgg gtaacgccag ggttttccca gtcacgacgt   12060
tgtaaaacga cggccagtga attgtaatac gactcactat agggcgaatt gggcccgacg   12120
tcgcatgcag tggtggtatt gtgactgggg atgtagttga gaataagtca tacacaagtc   12180
```

-continued

```
agctttcttc gagcctcata taagtataag tagttcaacg tattagcact gtacccagca    12240
tctccgtatc gagaaacaca acaacatgcc ccattggaca gatcatgcgg atacacaggt    12300
tgtgcagtat catacatact cgatcagaca ggtcgtctga ccatcataca agctgaacaa    12360
gcgctccata cttgcacgct ctctatatac acagttaaat tacatatcca tagtctaacc    12420
tctaacagtt aatcttctgg taagcctccc agccagcctt ctggtatcgc ttggcctcct    12480
caataggatc tcggttctgg ccgtacagac ctcggccgac aattatgata tccgttccgg    12540
tagacatgac atcctcaaca gttcggtact gctgtccgag agcgtctccc ttgtcgtcaa    12600
gacccacccc gggggtcaga ataagccagt cctcagagtc gcccttaat               12649
```

<210> SEQ ID NO 39
<211> LENGTH: 973
<212> TYPE: DNA
<213> ORGANISM: Yarrowia lipolytica
<220> FEATURE:
<221> NAME/KEY: misc_feature
<223> OTHER INFORMATION: Promoter FBAIN

<400> SEQUENCE: 39

```
aaattgcccc ggagaagacg gccaggccgc ctagatgaca aattcaacaa ctcacagctg      60
actttctgcc attgccacta gggggggggcc ttttatatg gccaagccaa gctctccacg     120
tcggttgggc tgcacccaac aataaatggg tagggttgca ccaacaaagg gatgggatgg     180
ggggtagaag atacgaggat aacgggggctc aatggcacaa ataagaacga atactgccat     240
taagactcgt gatccagcga ctgacaccat tgcatcatct aagggcctca aaactacctc     300
ggaactgctg cgctgatctg gacaccacag aggttccgag cactttaggt tgcaccaaat     360
gtcccaccag gtgcaggcag aaaacgctgg aacagcgtgt acagtttgtc ttaacaaaaa    420
gtgagggcgc tgaggtcgag cagggtggtg tgacttgtta tagcctttag agctgcgaaa     480
gcgcgtatgg atttggctca tcaggccaga ttgagggtct gtggacacat gtcatgttag    540
tgtacttcaa tcgccccctg gatatagccc cgacaatagg ccgtggcctc atttttttgc    600
cttccgcaca tttccattgc tcggtaccca caccttgctt ctcctgcact tgccaacctt    660
aatactggtt tacattgacc aacatcttac aagcgggggg cttgtctagg gtatatataa    720
acagtggctc tcccaatcgg ttgccagtct ctttttttcct ttctttcccc acagattcga   780
aatctaaact acacatcaca caatgcctgt tactgacgtc cttaagcgaa agtccggtgt    840
catcgtcggc gacgatgtcc gagccgtgag tatccacgac aagatcagtg tcgagacgac    900 gcgtttttgtg taatgacaca atccgaaagt cgctagcaac acacactctc tacacaaact   960
aacccagctc tcc                                                      973
```

<210> SEQ ID NO 40
<211> LENGTH: 957
<212> TYPE: DNA
<213> ORGANISM: Mortierella alpina
<220> FEATURE:
<221> NAME/KEY: misc_feature
<223> OTHER INFORMATION: synthetic elongase 1 (codon-optimized)

<400> SEQUENCE: 40

```
atggagtcca ttgctcccctt cctgccctcc aagatgcctc aggacctgtt catggacctc     60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
```

-continued

```
gtggagtctc ccctggctcg agagctgcct ctgatgaacc ccttccacgt gctcctgatc    240
gtgctcgcct acctggtcac cgtgtttgtg ggtatgcaga tcatgaagaa ctttgaacga    300
ttcgaggtca agaccttctc cctcctgcac aacttctgtc tggtctccat ctccgcctac    360
atgtgcggtg gcatcctgta cgaggcttat caggccaact atggactgtt tgagaacgct    420
gccgatcaca ccttcaaggg tctccctatg gctaagatga tctggctctt ctacttctcc    480
aagatcatgg agtttgtcga caccatgatc atggtcctca agaagaacaa ccgacagatt    540
tcctttctgc acgtgtacca ccactcttcc atcttcacca tctggtggct ggtcaccttc    600
gttgctccca acggtgaagc ctacttctct gctgccctga actccttcat ccacgtcatc    660
atgtacggct actactttct gtctgccctg ggcttcaagc aggtgtcgtt catcaagttc    720
tacatcactc gatcccagat gacccagttc tgcatgatgt ctgtccagtc ttcctgggac    780
atgtacgcca tgaaggtcct tggccgacct ggatacccct tcttcatcac cgctctgctc    840
tggttctaca tgtggaccat gctcggtctc ttctacaact tttaccgaaa gaacgccaag    900
ctcgccaagc aggccaaggc tgacgctgcc aaggagaagg ccagaaagct ccagtaa       957
```

<210> SEQ ID NO 41
<211> LENGTH: 318
<212> TYPE: PRT
<213> ORGANISM: Mortierella alpina AX464731

<400> SEQUENCE: 41

```
Met Glu Ser Ile Ala Pro Phe Leu Pro Ser Lys Met Pro Gln Asp Leu
 1               5                  10                  15

Phe Met Asp Leu Ala Thr Ala Ile Gly Val Arg Ala Ala Pro Tyr Val
                20                  25                  30

Asp Pro Leu Glu Ala Ala Leu Val Ala Gln Ala Glu Lys Tyr Ile Pro
             35                  40                  45

Thr Ile Val His His Thr Arg Gly Phe Leu Val Ala Val Glu Ser Pro
         50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240
```

```
Tyr Ile Thr Arg Ser Gln Met Thr Gln Phe Cys Met Met Ser Val Gln
            245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
            275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 42
<211> LENGTH: 1374
<212> TYPE: DNA
<213> ORGANISM: Mortierella alpina
<220> FEATURE:
<221> NAME/KEY: misc_feature
<223> OTHER INFORMATION: synthetic delta-6 desaturase (codon-optimized)

<400> SEQUENCE: 42
atggctgccg ctccctctgt gcgaaccttt acccgagccg aggttctgaa cgctgaggct      60
ctgaacgagg gcaagaagga cgctgaggct cccttcctga tgatcatcga caacaaggtg     120
tacgacgtcc gagagttcgt ccctgaccat cctggaggct ccgtgattct cacccacgtt     180
ggcaaggacg caccgacgt cttttgacacc tttcatcccg aggctgcttg ggagactctc     240
gccaacttct acgttggaga cattgacgag tccgaccgag acatcaagaa cgatgacttt     300
gccgctgagg tccgaaagct gcgaaccctg ttccagtctc tcggctacta cgactcctct     360
aaggcctact acgccttcaa ggtctccttc aacctctgca tctggggact gtccaccgtc     420
attgtggcca gtggggtca gacctccacc ctcgccaacg tgctctctgc tgccctgctc     480
ggcctgttct ggcagcagtg cggatggctg gctcacgact tctgcacca ccaggtcttc     540
caggaccgat tctggggtga tctcttcgga gccttcctgg aggtgtctg ccagggcttc     600
tcctcttcct ggtggaagga caagcacaac actcaccatg ccgctcccaa cgtgcatggc     660
gaggatcctg acattgacac ccaccctctc ctgacctggt ccgagcacgc tctggagatg     720
ttctccgacg tccccgatga ggagctgacc gaatgtggt ctcgattcat ggtcctgaac     780
cagacctggt tctacttccc cattctctcc ttcgctcgac tgtcttggtg cctccagtcc     840
attctctttg tgctgcccaa cggtcaggct cacaagccct ccggagctcg agtgcccatc     900
tccctggtcg agcagctgtc cctcgccatg cactggacct ggtacctcgc taccatgttc     960
ctgttcatca aggatcctgt caacatgctc gtgtacttcc tggtgtctca ggctgtgtgc    1020
ggaaacctgc tcgccatcgt gttctccctc aaccacaacg gtatgcctgt gatctccaag    1080
gaggaggctg tcgacatgga tttctttacc aagcagatca tcactggtcg agatgtccat    1140
cctggactgt tcgccaactg gttcaccggt ggcctgaact accagatcga gcatcacctg    1200
ttcccttcca tgcctcgaca caacttctcc aagatccagc tgccgtcga ccctgtgc       1260
aagaagtaca acgtccgata ccacaccact ggtatgatcg agggaactgc cgaggtcttc    1320
tcccgactga cgaggtctc caaggccacc tccaagatgg gcaaggctca gtaa           1374

<210> SEQ ID NO 43
<211> LENGTH: 457
<212> TYPE: PRT
<213> ORGANISM: Mortierella alpina AF465281

<400> SEQUENCE: 43
```

-continued

```
Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
                20                  25                  30

Leu Met Ile Ile Asp Asn Lys Val Tyr Asp Val Arg Glu Phe Val Pro
            35                  40                  45

Asp His Pro Gly Gly Ser Val Ile Leu Thr His Val Gly Lys Asp Gly
        50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
                100                 105                 110

Ser Leu Gly Tyr Tyr Asp Ser Ser Lys Ala Tyr Tyr Ala Phe Lys Val
            115                 120                 125

Ser Phe Asn Leu Cys Ile Trp Gly Leu Ser Thr Val Ile Val Ala Lys
130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
            195                 200                 205

His Asn Thr His His Ala Ala Pro Asn Val His Gly Glu Asp Pro Asp
            210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
            275                 280                 285

Gln Ala His Lys Pro Ser Gly Ala Arg Val Pro Ile Ser Leu Val Glu
            290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
                340                 345                 350

Asn Gly Met Pro Val Ile Ser Lys Glu Glu Ala Val Asp Met Asp Phe
            355                 360                 365

Phe Thr Lys Gln Ile Ile Thr Gly Arg Asp Val His Pro Gly Leu Phe
            370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415
```

```
Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Thr Ser Lys Met Gly Lys Ala Gln
    450                 455
```

<210> SEQ ID NO 44
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 44

| | | | | | |
|---|---|---|---|---|---|
| taaacagtgt | acgcagtact | atagaggaac | aattgccccg | gagaagacgg | ccaggccgcc | 60 |
| tagatgacaa | attcaacaac | tcacagctga | ctttctgcca | ttgccactag | gggggggcctt | 120 |
| tttatatggc | caagccaagc | tctccacgtc | ggttgggctg | cacccaacaa | taaatgggta | 180 |
| gggttgcacc | aacaaaggga | tgggatgggg | ggtagaagat | acgaggataa | cggggctcaa | 240 |
| tggcacaaat | aagaacgaat | actgccatta | agactcgtga | tccagcgact | gacaccattg | 300 |
| catcatctaa | gggcctcaaa | actacctcgg | aactgctgcg | ctgatctgga | caccacagag | 360 |
| gttccgagca | ctttaggttg | caccaaatgt | cccaccaggt | gcaggcagaa | aacgctggaa | 420 |
| cagcgtgtac | agtttgtctt | aacaaaaagt | gagggcgctg | aggtcgagca | gggtggtgtg | 480 |
| acttgttata | gcctttagag | ctgcgaaagc | gcgtatggat | ttggctcatc | aggccagatt | 540 |
| gagggtctgt | ggacacatgt | catgttagtg | tacttcaatc | gccccctgga | tatagccccg | 600 |
| acaataggcc | gtggcctcat | ttttttgcct | tccgcacatt | tccattgctc | ggtacccaca | 660 |
| ccttgcttct | cctgcacttg | ccaaccttaa | tactggttta | cattgaccaa | catcttacaa | 720 |
| gcgggggggct | tgtctagggt | atatataaac | agtggctctc | ccaatcggtt | gccagtctct | 780 |
| tttttccttt | ctttcccccac | agattcgaaa | tctaaactac | acatcacaca | atgcctgtta | 840 |
| ctgacgtcct | taagcgaaag | tccggtgtca | tcgtcggcga | cgatgtccga | gccgtgagta | 900 |
| tccacgacaa | gatcagtgtc | gagacgacgc | gttttgtgta | atgacacaat | ccgaaagtcg | 960 |
| ctagcaacac | acactctcta | cacaaactaa | cccagctctc | c | | 1001 |

<210> SEQ ID NO 45
<211> LENGTH: 1434
<212> TYPE: DNA
<213> ORGANISM: Fusarium monoliforme
<220> FEATURE:
<221> NAME/KEY: misc_feature
<223> OTHER INFORMATION: delta-12 desaturase

<400> SEQUENCE: 45

| | | | | | |
|---|---|---|---|---|---|
| atggcgtcca | cttcggctct | gcccaagcag | aaccctgcgc | ttagacgcac | cgtcacctca | 60 |
| actactgtga | cggattctga | gtctgccgcc | gtctctcctt | cagactctcc | ccgccactcg | 120 |
| gcctcttcca | catcgctctc | gtccatgtcc | gaggttgata | tcgccaagcc | caagtccgag | 180 |
| tatggtgtca | tgctcgacac | ctacggcaac | cagttcgagg | ttcccgactt | taccatcaag | 240 |
| gacatctaca | atgccatccc | taagcactgc | ttcaagcgct | ccgctctcaa | gggatacggt | 300 |
| tatatcctcc | gcgacattgt | cctcctgact | accactttca | gcatctggta | caactttgtg | 360 |
| acccccgaat | atatcccctc | caccccgcc | cgcgctggtc | tgtgggccgt | gtacaccgtt | 420 |

-continued

```
cttcagggtc ttttcggtac tggtctctgg gttattgccc atgagtgcgg tcacggtgct    480
ttctccgatt ctcgcatcat caacgacatt actggctggg ttcttcactc ttccctcctt    540
gtcccctact tcagctggca aatctcccac cgaaagcacc acaaggccac tggcaacatg    600
gagcgtgaca tggtcttcgt tccccgaacc cgcgagcagc aggctactcg tctcggaaag    660
atgacccacg agctcgctca tcttactgag gagaccccg ctttcactct tctcatgctc    720
gtccttcagc agctcgttgg ctggcccaac tacctcatca ccaatgttac cggccacaac    780
taccacgagc gccagcgtga gggtcgcggc aagggcaagc ataacggcct cggcggtggt    840
gttaaccact tcgatccccg cagccctctg tacgagaaca gtgacgctaa gctcatcgtc    900
ctcagcgata ttggtatcgg tctgatggcc actgctctgt acttcctcgt tcagaagttc    960
ggtttctaca acatggccat ctggtacttt gttccctacc tctgggttaa ccactggctc   1020
gttgccatca ccttcctcca gcacaccgac cctacccttc cccactacac caacgacgag   1080
tggaacttcg tccgtggtgc cgctgctacc attgaccgtg agatgggctt catcggccgc   1140
caccttctcc acggcatcat cgagactcat gtcctccacc actacgtcag cagcatcccc   1200
ttctacaacg cggacgaggc caccgaggcc attaagccca tcatgggcaa gcactaccgg   1260
gctgatgtcc aggatggtcc tcgtggcttc atccgcgcca tgtaccgcag tgcgcgtatg   1320
tgccagtggg ttgagcccag cgctggtgcc gagggtgctg gtaagggtgt tctgttcttc   1380
cgcaaccgca acaacgtggg caccccccccc gctgttatca agcccgttgc ttaa         1434
```

<210> SEQ ID NO 46
<211> LENGTH: 477
<212> TYPE: PRT
<213> ORGANISM: Fusarium monoliforme

<400> SEQUENCE: 46

```
Met Ala Ser Thr Ser Ala Leu Pro Lys Gln Asn Pro Ala Leu Arg Arg
1               5                   10                  15

Thr Val Thr Ser Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
```

```
                195                 200                 205
Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
                260                 265                 270

Lys His Asn Gly Leu Gly Gly Val Asn His Phe Asp Pro Arg Ser
    275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
                340                 345                 350

Leu Pro His Tyr Thr Asn Asp Glu Trp Asn Phe Val Arg Gly Ala Ala
                355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
                420                 425                 430

Ala Met Tyr Arg Ser Ala Arg Met Cys Gln Trp Val Glu Pro Ser Ala
                435                 440                 445

Gly Ala Glu Gly Ala Gly Lys Gly Val Leu Phe Phe Arg Asn Arg Asn
450                 455                 460

Asn Val Gly Thr Pro Pro Ala Val Ile Lys Pro Val Ala
465                 470                 475

<210> SEQ ID NO 47
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)

<400> SEQUENCE: 47
atggccaact cctctgtctg ggacgacgtg gtcggacgag tcgagaccgg tgtcgaccag      60
tggatggacg gagctaagcc ctacgctctg accgacggtc tgcccatgat ggacgtctcc     120
accatgctcg ccttcgaggt cggctacatg gccatgctgc tcttcggcat tcccatcatg     180
aagcagatgg agaagccctt cgagctgaag accatcaagc tgctccacaa cctgttcctc     240
ttcggactgt ccctctacat gtgcgtcgag accatccgac aggctatcct gggtggctac     300
aaggtcttcg gcaacgacat ggagaagggc aacgagtccc acgctcaggg catgtcccga     360
atcgtctacg tgttctacgt ctccaaggcc tacgagttcc tggacaccgc tatcatgatc     420
ctgtgcaaga gttcaaccaa ggtctccttc ctgcacgtgt accaccatgc caccatcttc     480
```

```
gccatctggt gggctattgc caagtacgct cctggtggcg acgcctactt ctccgtcatc    540
ctcaactcct tcgtccacac cgtcatgtac gcctactact tcttttcctc tcagggcttc    600
ggcttcgtca gcccatcaa gccctacatc accactctgc agatgaccca gttcatggct     660
atgctggtgc agtccctgta cgactacctc ttccctgcg actaccctca ggctctggtc     720
cagctgctcg gcgtgtacat gatcaccctg ctcgctctgt tcggcaactt ctttgtccag    780
tcctacctga agaagcccaa gaagtccaag accaactaa                           819
```

```
<210> SEQ ID NO 48
<211> LENGTH: 272
<212> TYPE: PRT
<213> ORGANISM: Thraustochytrium aureum

<400> SEQUENCE: 48
```

Met Ala Asn Ser Ser Val Trp Asp Asp Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270

```
<210> SEQ ID NO 49
<211> LENGTH: 10945
<212> TYPE: DNA
<213> ORGANISM: Artificial Sequence
<220> FEATURE:
<223> OTHER INFORMATION: Plasmid pDMW232
```

-continued

<400> SEQUENCE: 49

```
aattcctgca gcccatcgat caggagagac cgggttggcg gcgtatttgt gtcccaaaaa      60
acagccccaa ttgccccaat tgaccccaaa ttgacccagt agcgggccca accccggcga     120
gagccccctt caccccacat atcaaacctc ccccggttcc cacacttgcc gttaagggcg     180
tagggtactg cagtctggaa tctacgcttg ttcagacttt gtactagttt ctttgtctgg     240
ccatccgggt aacccatgcc ggacgcaaaa tagactactg aaaattttt tgctttgtgg      300
ttgggacttt agccaagggt ataaaagacc accgtcccg aattacctt cctcttcttt       360
tctctctctc cttgtcaact cacacccgaa atcgttaagc atttccttct gagtataaga     420
atcattcacc atgggaacgg accaaggaaa accttcacc tgggaagagc tggcggccca      480
taacaccaag gacgacctac tcttggccat ccgcggcagg gtgtacgatg tcacaaagtt     540
cttgagccgc catcctggtg gagtggacac tctcctgctc ggagctggcc gagatgttac     600
tccggtcttt gagatgtatc acgcgtttgg ggctgcagat gccattatga agaagtacta     660
tgtcggtaca ctggtctcga atgagctgcc catcttcccg gagccaacgg tgttccacaa     720
aaccatcaag acgagagtcg agggctactt tacggatcgg aacattgatc ccaagaatag     780
accagagatc tggggacgat acgctcttat ctttggatcc ttgatcgctt cctactacgc     840
gcagctcttt gtgcctttcg ttgtcgaacg cacatggctt caggtggtgt ttgcaatcat     900
catgggattt gcgtgcgcac aagtcggact caaccctctt catgatgcgt ctcacttttc     960
agtgacccac aaccccactg tctggaagat tctgggagcc acgcacgact ttttcaacgg    1020
agcatcgtac ctggtgtgga tgtaccaaca tatgctcggc catcacccct acaccaacat    1080
tgctggagca gatcccgacg tgtcgacgtc tgagcccgat gttcgtcgta tcaagcccaa    1140
ccaaaagtgg tttgtcaacc acatcaacca gcacatgttt gttcctttcc tgtacggact    1200
gctggcgttc aaggtgcgca ttcaggacat caacattttg tactttgtca agaccaatga    1260
cgctattcgt gtcaatccca tctcgacatg gcacactgtg atgttctggg gcggcaaggc    1320
tttcttttgtc tggtatcgcc tgattgttcc cctgcagtat ctgcccctgg gcaaggtgct    1380
gctcttgttc acggtcgcgg acatggtgtc gtcttactgg ctggcgctga ccttccaggc    1440
gaaccacgtt gttgaggaag ttcagtggcc gttgcctgac gagaacggga tcatccaaaa    1500
ggactgggca gctatgcagg tcgagactac gcaggattac gcacacgatt cgcacctctg    1560
gaccagcatc actggcagct tgaactacca ggctgtgcac catctgttcc caacgtgtc     1620
gcagcaccat tatcccgata ttctggccat catcaagaac acctgcagcg agtacaaggt    1680
tccataccct gtcaaggata cgttttggca agcatttgct tcacatttgg agcacttgcg    1740
tgttcttgga ctccgtccca aggaagagta ggcagctaag cggccgcatg agaagataaa    1800
tatataaata cattgagata ttaaatgcgc tagattagag agcctcatac tgctcggaga    1860
gaagccaaga cgagtactca aagggagtta caccatccat atccacagac acaagctggg    1920
gaaaggttct atatacactt tccggaatac cgtagtttcc gatgttatca atgggggcag    1980
ccaggatttc aggcacttcg tgtgtctcggg gtgaaatggc gttcttggcc tccatcaagt    2040
cgtaccatgt cttcatttgc ctgtcaaagt aaaacagaag cagatgaaga atgaacttga    2100
agtgaaggaa tttaaattgc cccggagaag acggccaggc cgcctagatg acaaattcaa    2160
caactcacag ctgactttct gccattgcca ctaggggggg gccttttat atggccaagc     2220
caagctctcc acgtcggttg ggctgcaccc aacaataaat gggtagggtt gcaccaacaa    2280
```

-continued

```
agggatggga tgggggtag aagatacgag gataacgggg ctcaatggca caaataagaa    2340
cgaatactgc cattaagact cgtgatccag cgactgacac cattgcatca tctaagggcc    2400
tcaaaactac ctcggaactg ctgcgctgat ctggacacca cagaggttcc gagcacttta    2460
ggttgcacca aatgtcccac caggtgcagg cagaaaacgc tggaacagcg tgtacagttt    2520
gtcttaacaa aaagtgaggg cgctgaggtc gagcagggtg gtgtgacttg ttatagcctt    2580
tagagctgcg aaagcgcgta tggatttggc tcatcaggcc agattgaggg tctgtggaca    2640
catgtcatgt tagtgtactt caatcgcccc ctggatatag ccccgacaat aggccgtggc    2700 ctcattttt tgccttccgc acatttccat tgctcggtac ccacaccttg cttctcctgc    2760
acttgccaac cttaatactg gtttacattg accaacatct tacaagcggg gggcttgtct    2820
agggtatata taaacagtgg ctctcccaat cggttgccag tctcttttt cctttcttc    2880 cccacagatt cgaaatctaa actacacatc acacaatgcc tgttactgac gtccttaagc    2940
gaaagtccgg tgtcatcgtc ggcgacgatg tccgagccgt gagtatccac gacaagatca    3000
gtgtcgagac gacgcgtttt gtgtaatgac acaatccgaa agtcgctagc aacacacact    3060
ctctacacaa actaacccag ctctccatgg gaacggacca aggaaaaacc ttcacctggg    3120
aagagctggc ggcccataac accaaggacg acctactctt ggccatccgc ggcagggtgt    3180
acgatgtcac aaagttcttg agccgccatc ctggtggagt ggacactctc ctgctcggag    3240
ctggccgaga tgttactccg gtctttgaga tgtatcacgc gtttggggct gcagatgcca    3300
ttatgaagaa gtactatgtc ggtacactgg tctcgaatga gctgcccatc ttcccggagc    3360
caacggtgtt ccacaaaacc atcaagacga gagtcgaggg ctactttacg gatcggaaca    3420
ttgatcccaa gaatagacca gagatctggg gacgatacgc tcttatcttt ggatccttga    3480
tcgcttccta ctacgcgcag ctctttgtgc ctttcgttgt cgaacgcaca tggcttcagg    3540
tggtgtttgc aatcatcatg ggatttgcgt gcgcacaagt cggactcaac cctcttcatg    3600
atgcgtctca cttttcagtg acccacaacc ccactgtctg gaagattctg ggagccacgc    3660 acgactttt caacggagca tcgtacctgg tgtggatgta ccaacatatg ctcggccatc    3720
acccctacac caacattgct ggagcagatc ccgacgtgtc gacgtctgag cccgatgttc    3780
gtcgtatcaa gcccaaccaa aagtggtttg tcaaccacat caaccagcac atgtttgttc    3840
ctttcctgta cggactgctg gcgttcaagg tgcgcattca ggacatcaac atttttgtact    3900 ttgtcaagac caatgacgct attcgtgtca atcccatctc gacatggcac actgtgatgt    3960 tctgggcgg caaggctttc tttgtctggt atcgcctgat tgttcccctg cagtatctgc    4020
ccctgggcaa ggtgctgctc ttgttcacgg tcgcggacat ggtgtcgtct tactggctgg    4080
cgctgacctt ccaggcgaac cacgttgttg aggaagttca gtggccgttg cctgacgaga    4140
acgggatcat ccaaaaggac tgggcagcta tgcaggtcga gactacgcag gattacgcac    4200
acgattcgca cctctggacc agcatcactg gcagcttgaa ctaccaggct gtgcaccatc    4260 tgttcccccaa cgtgtcgcag caccattatc ccgatattct ggccatcatc aagaacacct    4320
gcagcgagta caaggttcca taccttgtca aggatacgtt ttggcaagca tttgcttcac    4380
atttggagca cttgcgtgtt cttggactcc gtcccaagga agagtaggca gctaagcggc    4440
cgcaagtgtg gatgggaag tgagtgcccg gttctgtgtg cacaattggc aatccaagat    4500
ggatggattc aacacaggga tatagcgagc tacgtggtgg tgcgaggata tagcaacgga    4560
tatttatgtt tgacacttga gaatgtacga tacaagcact gtccaagtac aatactaaac    4620
atactgtaca tactcatact cgtacccggg caacggtttc acttgagtgc agtggctagt    4680
```

-continued

```
gctcttactc gtacagtgtg caatactgcg tatcatagtc tttgatgtat atcgtattca    4740
ttcatgttag ttgcgtacgc caccattctg tctgccgcca tgatgctcaa gttctctctt    4800
aacatgaagc ccgccggtga cgctgttgag gctgccgtca aggagtccgt cgaggctggt    4860
atcactaccg ccgatatcgg aggctcttcc tccacctccg aggtcggaga cttgttgcca    4920
acaaggtcaa ggagctgctc aagaaggagt aagtcgtttc tacgacgcat tgatggaagg    4980
agcaaactga cgcgcctgcg ggttggtcta ccggcagggt ccgctagtgt ataagactct    5040
ataaaaaggg ccctgccctg ctaatgaaat gatgatttat aatttaccgg tgtagcaacc    5100
ttgactagaa gaagcagatt gggtgtgttt gtagtggagg acagtggtac gttttggaaa    5160
cagtcttctt gaaagtgtct tgtctacagt atattcactc ataacctcaa tagccaaggg    5220
tgtagtcggt ttattaaagg aagggagttg tggctgatgt ggatagatat ctttaagctg    5280
gcgactgcac ccaacgagtg tggtggtagc ttgttactgt atattcggta agatatattt    5340
tgtggggttt tagtggtgtt tggtaggtta gtgcttggta tatgagttgt aggcatgaca    5400
atttggaaag gggtggactt tgggaatatt gtgggatttc ataaccttag tttgtacagg    5460
gtaattgtta caaatgatac aaagaactgt atttcttttc atttgtttta attggttgta    5520
tatcaagtcc gttagacgag ctcagtgggc gcgccagctg cattaatgaa tcggccaacg    5580
cgcggggaga ggcggtttgc gtattgggcg ctcttccgct tcctcgctca ctgactcgct    5640
gcgctcggtc gttcggctgc ggcgagcgg atcagctcac tcaaaggcgg taatacggtt    5700
atccacagaa tcagggata acgcaggaaa gaacatgtga gcaaaaggcc agcaaaaggc    5760
caggaaccgt aaaaaggccg cgttgctggc gttttccat aggctccgcc ccctgacga    5820 gcatcacaaa aatcgacgct caagtcagag gtggcgaaac ccgacaggac tataaagata    5880
ccaggcgttt ccccctggaa gctccctcgt gcgctctcct gttccgaccc tgccgcttac    5940
cggatacctg tccgccttc tcccttcggg aagcgtggcg ctttctcata gctcacgctg    6000
taggtatctc agttcggtgt aggtcgttcg ctccaagctg ggctgtgtgc acgaaccccc    6060
cgttcagccc gaccgctgcg ccttatccgg taactatcgt cttgagtcca acccggtaag    6120
acacgactta tcgccactgg cagcagccac tggtaacagg attagcagag cgaggtatgt    6180
aggcggtgct acagagttct tgaagtggtg gcctaactac ggctacacta agaacagt    6240 atttggtatc tgcgctctgc tgaagccagt taccttcgga aaaagagttg gtagctcttg    6300
atccggcaaa caaccaccg ctggtagcgg tggtttttttt gtttgcaagc agcagattac    6360
gcgcagaaaa aaggatctca agaagatcc tttgatcttt tctacggggt ctgacgctca    6420
gtggaacgaa aactcacgtt aagggatttt ggtcatgaga ttatcaaaaa ggatcttcac    6480
ctagatcctt ttaaattaaa aatgaagttt taaatcaatc taaagtatat atgagtaaac    6540
ttggtctgac agttaccaat gcttaatcag tgaggcacct atctcagcga tctgtctatt    6600
tcgttcatcc atagttgcct gactccccgt cgtgtagata actacgatac gggagggctt    6660
accatctggc cccagtgctg caatgatacc gcgagaccca cgctcaccgg ctccagattt    6720
atcagcaata aaccagccag ccggaagggc cgagcgcaga agtggtcctg caactttatc    6780
cgcctccatc cagtctatta attgttgccg ggaagctaga gtaagtagtt cgccagttaa    6840
tagtttgcgc aacgttgttg ccattgctac aggcatcgtg gtgtcacgct cgtcgtttgg    6900
tatggcttca ttcagctccg gttcccaacg atcaaggcga gttacatgat cccccatgtt    6960
gtgcaaaaaa gcggttagct ccttcggtcc tccgatcgtt gtcagaagta agttggccgc    7020
```

```
agtgttatca ctcatggtta tggcagcact gcataattct cttactgtca tgccatccgt    7080
aagatgcttt tctgtgactg gtgagtactc aaccaagtca ttctgagaat agtgtatgcg    7140
gcgaccgagt tgctcttgcc cggcgtcaat acgggataat accgcgccac atagcagaac    7200
tttaaaagtg ctcatcattg gaaaacgttc ttcggggcga aaactctcaa ggatcttacc    7260
gctgttgaga tccagttcga tgtaacccac tcgtgcaccc aactgatctt cagcatcttt    7320
tactttcacc agcgtttctg ggtgagcaaa aacaggaagg caaaatgccg caaaaaaggg    7380
aataagggcg acacggaaat gttgaatact catactcttc ctttttcaat attattgaag    7440
catttatcag ggttattgtc tcatgagcgg atacatattt gaatgtattt agaaaaataa    7500
acaaataggg gttccgcgca catttccccg aaaagtgcca cctgatgcgg tgtgaaatac    7560
cgcacagatg cgtaaggaga aaataccgca tcaggaaatt gtaagcgtta atattttgtt    7620
aaaattcgcg ttaaattttt gttaaatcag ctcattttt  aaccaatagg ccgaaatcgg    7680
caaaatccct tataaatcaa agaatagac  cgagataggg ttgagtgttg ttccagtttg    7740
gaacaagagt ccactattaa agaacgtgga ctccaacgtc aaagggcgaa aaaccgtcta    7800
tcagggcgat ggcccactac gtgaaccatc accctaatca agttttttgg ggtcgaggtg    7860
ccgtaaagca ctaaatcgga accctaaagg gagcccccga tttagagctt gacggggaaa    7920
gccggcgaac gtggcgagaa aggaagggaa gaaagcgaaa ggagcgggcg ctagggcgct    7980
ggcaagtgta gcggtcacgc tgcgcgtaac caccacaccc gccgcgctta atgcgccgct    8040
acagggcgcg tccattcgcc attcaggctg cgcaactgtt gggaagggcg atcggtgcgg    8100
gcctcttcgc tattacgcca gctggcgaaa gggggatgtg ctgcaaggcg attaagttgg    8160
gtaacgccag ggtttttccca gtcacgacgt tgtaaaacga cggccagtga attgtaatac    8220
gactcactat agggcgaatt gggcccgacg tcgcatgcta tcggcatcga caaggtttgg    8280
gtccctagcc gataccgcac tacctgagtc acaatcttcg gaggtttagt cttccacata    8340
gcacgggcaa aagtgcgtat atatacaaga gcgtttgcca gccacagatt ttcactccac    8400
acaccacatc acacatacaa ccacacacat ccacaatgga acccgaaact aagaagacca    8460
agactgactc caagaagatt gttcttctcg gcggcgactt ctgtggcccc gaggtgattg    8520
ccgaggccgt caaggtgctc aagtctgttg ctgaggcctc cggcaccgag tttgtgtttg    8580
aggaccgact cattggagga gctgccattg agaaggaggg cgagcccatc accgacgcta    8640
ctctcgacat ctgccgaaag gctgactcta ttatgctcgg tgctgtcgga ggcgctgcca    8700
acaccgtatg gaccactccc gacggacgaa ccgacgtgcg acccgagcag ggtctcctca    8760
agctgcgaaa ggacctgaac ctgtacgcca acctgcgacc ctgccagctg ctgtcgccca    8820
agctcgccga tctctccccc atccgaaacg ttgagggcac cgacttcatc attgtccgag    8880
agctcgtcgg aggtatctac tttggagagc gaaaggagga tgacggatct ggcgtcgctt    8940
ccgacaccga gacctactcc gttaattaat ttgaatcgaa tcgatgagcc taaaatgaac    9000
ccgagtatat ctcataaaat tctcggtgag aggtctgtga ctgtcagtac aaggtgcctt    9060
cattatgccc tcaaccttac catacctcac tgaatgtagt gtacctctaa aaatgaaata    9120
cagtgccaaa agccaaggca ctgagctcgt ctaacggact tgatatacaa ccaattaaaa    9180
caaatgaaaa gaaatacagt tctttgtatc atttgtaaca attaccctgt acaaactaag    9240
gtattgaaat cccacaatat tcccaaagtc caccccttc  caaattgtca tgcctacaac    9300
tcatatacca agcactaacc taccgtttaa acagtgtacg cagatctggt gtagtggtag    9360
tgcagtggtg gtattgtgac tggggatgta gttgagaata agtcatacac aagtcagctt    9420
```

-continued

```
tcttcgagcc tcatataagt ataagtagtt caacgtatta gcactgtacc cagcatctcc   9480
gtatcgagaa acacaacaac atgccccatt ggacagatca tgcggataca caggttgtgc   9540
agtatcatac atactcgatc agacaggtcg tctgaccatc atacaagctg aacaagcgct   9600
ccatacttgc acgctctcta tatacacagt taaattacat atccatagtc taacctctaa   9660
cagttaatct tctggtaagc ctcccagcca gccttctggt atcgcttggc ctcctcaata   9720
ggatctcggt tctggccgta cagacctcgg ccgacaatta tgatatccgt tccggtagac   9780
atgacatcct caacagttcg gtactgctgt ccgagagcgc tcccttgtc gtcaagaccc    9840 accccggggg tcagaataag ccagtcctca gagtcgccct taggtcggtt ctgggcaatg   9900
aagccaacca caaactcggg gtcggatcgg gcaagctcaa tggtctgctt ggagtactcg   9960
ccagtggcca gagagccctt gcaagacagc tcggccagca tgagcagacc tctggccagc   10020
ttctcgttgg gagaggggac taggaactcc ttgtactggg agttctcgta gtcagagacg   10080
tcctccttct tctgttcaga gacagtttcc tcggcaccag ctcgcaggcc agcaatgatt   10140
ccggttccgg gtacaccgtg ggcgttggtg atatcggacc actcggcgat tcggtgacac   10200
cggtactggt gcttgacagt gttgccaata tctgcgaact ttctgtcctc gaacaggaag   10260
aaaccgtgct taagagcaag ttccttgagg gggagcacag tgccggcgta ggtgaagtcg   10320
tcaatgatgt cgatatgggt tttgatcatg cacacataag gtccgacctt atcggcaagc   10380
tcaatgagct ccttggtggt ggtaacatcc agagaagcac acaggttggt tttcttggct   10440
gccacgagct tgagcactcg agcggcaaag gcggacttgt ggacgttagc tcgagcttcg   10500
taggagggca ttttggtggt gaagaggaga ctgaaataaa tttagtctgc agaactttt    10560 atcggaacct tatctggggc agtgaagtat atgttatggt aatagttacg agttagttga   10620
acttatagat agactggact atacggctat cggtccaaat tagaaagaac gtcaatggct   10680
ctctgggcgt cgccttttgcc gacaaaaatg tgatcatgat gaaagccagc aatgacgttg   10740
cagctgatat tgttgtcggc caaccgcgcc gaaaacgcag ctgtcagacc cacagcctcc   10800
aacgaagaat gtatcgtcaa agtgatccaa gcacactcat agttggagtc gtactccaaa   10860
ggcggcaatg acgagtcaga cagatactcg tcgaccttt ccttgggaac caccaccgtc    10920
agcccttctg actcacgtat tgtag                                         10945
```

<210> SEQ ID NO 50
<211> LENGTH: 1341
<212> TYPE: DNA
<213> ORGANISM: Mortierella alpina AF067654
<220> FEATURE:
<221> NAME/KEY: misc_feature
<223> OTHER INFORMATION: delta-5 desaturase

<400> SEQUENCE: 50

```
atgggaacgg accaaggaaa aaccttcacc tgggaagagc tggcggccca taacaccaag     60
gacgacctac tcttggccat ccgcggcagg gtgtacgatg tcacaaagtt cttgagccgc    120
catcctggtg gagtggacac tctcctgctc ggagctggcc gagatgttac tccggtcttt    180
gagatgtatc acgcgtttgg ggctgcagat gccattatga agaagtacta tgtcggtaca    240
ctggtctcga atgagctgcc catcttcccg gagccaacgg tgttccacaa aaccatcaag    300
acgagagtcg agggctactt tacggatcgg aacattgatc ccaagaatag accagagatc    360
tggggacgat acgctcttat ctttggatcc ttgatcgctt cctactacgc gcagctcttt    420
gtgcctttcg ttgtcgaacg cacatggctt caggtggtgt ttgcaatcat catgggattt    480
```

```
gcgtgcgcac aagtcggact caaccctctt catgatgcgt ctcactttc agtgacccac      540 aaccccactg tctggaagat tctgggagcc acgcacgact ttttcaacgg agcatcgtac      600
ctggtgtgga tgtaccaaca tatgctcggc catcacccct acaccaacat tgctggagca      660
gatcccgacg tgtcgacgtc tgagcccgat gttcgtcgta tcaagcccaa ccaaaagtgg      720
tttgtcaacc acatcaacca gcacatgttt gttccttttcc tgtacggact gctggcgttc      780
aaggtgcgca ttcaggacat caacattttg tactttgtca agaccaatga cgctattcgt      840
gtcaatccca tctcgacatg gcacactgtg atgttctggg gcggcaaggc tttctttgtc      900
tggtatcgcc tgattgttcc cctgcagtat ctgcccctgg gcaaggtgct gctcttgttc      960
acggtcgcgg acatggtgtc gtcttactgg ctggcgctga ccttccaggc gaaccacgtt     1020
gttgaggaag ttcagtggcc gttgcctgac gagaacggga tcatccaaaa ggactgggca     1080
gctatgcagg tcgagactac gcaggattac gcacacgatt cgcacctctg gaccagcatc     1140
actggcagct tgaactacca ggctgtgcac catctgttcc ccaacgtgtc gcagcaccat     1200
tatcccgata ttctggccat catcaagaac acctgcagcg agtacaaggt tccatacctt     1260
gtcaaggata cgttttggca gcatttgctt cacatttgg agcacttgcg tgttcttgga     1320
ctccgtccca aggaagagta g                                              1341

<210> SEQ ID NO 51
<211> LENGTH: 446
<212> TYPE: PRT
<213> ORGANISM: Mortierella alpina AF067654

<400> SEQUENCE: 51

Met Gly Thr Asp Gln Gly Lys Thr Phe Thr Trp Glu Glu Leu Ala Ala
1               5                  10                  15

His Asn Thr Lys Asp Asp Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
```

-continued

```
                210                 215                 220
Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
                260                 265                 270

Val Lys Thr Asn Asp Ala Ile Arg Val Asn Pro Ile Ser Thr Trp His
                275                 280                 285

Thr Val Met Phe Trp Gly Gly Lys Ala Phe Phe Val Trp Tyr Arg Leu
290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
                340                 345                 350

Gly Ile Ile Gln Lys Asp Trp Ala Ala Met Gln Val Glu Thr Thr Gln
                355                 360                 365

Asp Tyr Ala His Asp Ser His Leu Trp Thr Ser Ile Thr Gly Ser Leu
                370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
                420                 425                 430

Leu Glu His Leu Arg Val Leu Gly Leu Arg Pro Lys Glu Glu
                435                 440                 445
```

```
<210> SEQ ID NO 52
<211> LENGTH: 12690
<212> TYPE: DNA
<213> ORGANISM: Artificial Sequence
<220> FEATURE:
<223> OTHER INFORMATION: Plasmid pZP3L37

<400> SEQUENCE: 52
aaataccagt tggccacaaa cccttgacga tctcgtatgt cccctccgac atactcccgg      60
ccggctgggg tacgttcgat agcgctatcg gcatcgacaa ggtttgggtc cctagccgat     120
accgcactac ctgagtcaca atcttcggag gtttagtctt ccacatagca cgggcaaaag    180
tgcgtatata tacaagagcg tttgccagcc acagattttc actccacaca ccacatcaca    240
catacaacca cacacatcca caatggaacc cgaaactaag aagaccaaga ctgactccaa    300
gaagattgtt cttctcggcg gcgacttctg tggccccgag gtgattgccg aggccgtcaa    360
ggtgctcaag tctgttgctg aggcctccgg caccgagttt gtgtttgagg accgactcat    420
tggaggagct gccattgaga aggagggcga gcccatcacc gacgctactc tcgacatctg    480
ccgaaaggct gactctatta tgctcggtgc tgtcggaggc gctgccaaca ccgtatggac    540
cactcccgac ggacgaaccg acgtgcgacc cgagcagggt ctcctcaagc tgcgaaagga    600
cctgaacctg tacgccaacc tgcgaccctg ccagctgctg tcgcccaagc tcgccgatct    660
ctcccccatc cgaaacgttg agggcaccga cttcatcatt gtccgagagc tcgtcggagg    720
tatctacttt ggagagcgaa aggaggatga cggatctggc gtcgcttccg acaccgagac    780
```

```
ctactccgtt cctgaggttg agcgaattgc ccgaatggcc gccttcctgg cccttcagca     840
caacccccct cttcccgtgt ggtctcttga caaggccaac gtgctggcct cctctcgact     900
ttggcgaaag actgtcactc gagtcctcaa ggacgaattc ccccagctcg agctcaacca     960
ccagctgatc gactcggccg ccatgatcct catcaagcag ccctccaaga tgaatggtat    1020
catcatcacc accaacatgt tggcgatat catctccgac gaggcctccg tcatccccgg     1080
ttctctgggt ctgctgccct ccgcctctct ggcttctctg cccgacacca acgaggcgtt    1140
cggtctgtac gagccctgtc acggatctgc ccccgatctc ggcaagcaga aggtcaaccc    1200
cattgccacc attctgtctg ccgccatgat gctcaagttc tctcttaaca tgaagcccgc    1260
cggtgacgct gttgaggctg ccgtcaagga gtccgtcgag gctggtatca ctaccgccga    1320
tatcggaggc tcttcctcca cctccgaggt cggagacttg ttgccaacaa ggtcaaggag    1380
ctgctcaaga aggagtaagt cgtttctacg acgcattgat ggaaggagca aactgacgcg    1440
cctgcgggtt ggtctaccgg cagggtccgc tagtgtataa gactctataa aaagggccct    1500
gccctgctaa tgaaatgatg atttataatt taccggtgta gcaaccttga ctagaagaag    1560
cagattgggt gtgtttgtag tggaggacag tggtacgttt tggaaacagt cttcttgaaa    1620
gtgtcttgtc tacagtatat tcactcataa cctcaatagc caaggtgta gtcggtttat     1680 taaaggaagg gagttgtggc tgatgtggat agatatcttt aagctggcga ctgcacccaa    1740
cgagtgtggt ggtagcttgt tagatctgta tattcggtaa gatatatttt gtggggtttt    1800
agtggtgttt aaacagtgta cgcagtacta tagaggaaca attgccccgg agaagacggc    1860
caggccgcct agatgacaaa ttcaacaact cacagctgac tttctgccat gccactagg     1920 ggggggcctt tttatatggc caagccagc tctccacgtc ggttgggctg cacccaacaa    1980
taaatgggta gggttgcacc aacaaaggga tgggatgggg ggtagaagat acgaggataa    2040
cggggctcaa tggcacaaat aagaacgaat actgccatta agactcgtga tccagcgact    2100
gacaccattg catcatctaa gggcctcaaa actacctcgg aactgctgcg ctgatctgga    2160
caccacagag gttccgagca ctttaggttg caccaaatgt cccaccaggt gcaggcagaa    2220
aacgctggaa cagcgtgtac agtttgtctt aacaaaaagt gagggcgctg aggtcgagca    2280
gggtggtgtg acttgttata gcctttagag ctgcgaaagc gcgtatggat ttggctcatc    2340
aggccagatt gagggtctgt ggacacatgt catgttagtg tacttcaatc gcccctgga    2400 tatagccccg acaataggcc gtggcctcat tttttttgcct tccgcacatt tccattgctc    2460
ggtacccaca ccttgcttct cctgcacttg ccaaccttaa tactggttta cattgaccaa    2520
catcttacaa gcgggggct tgtctagggt atatataaac agtggctctc ccaatcggtt    2580
gccagtctct ttttcctttt cttccccac agattcgaaa tctaaactac acatcacaca    2640
atgcctgtta ctgacgtcct taagcgaaag tccggtgtca tcgtcggcga cgatgtccga    2700
gccgtgagta tccacgacaa gatcagtgtc gagacgacgc gttttgtgta atgacacaat    2760
ccgaaagtcg ctagcaacac acactctcta cacaaactaa cccagctctc catggctgag    2820
gataagacca aggtcgagtt ccctaccctg actgagctga agcactctat ccctaacgct    2880
tgctttgagt ccaacctcgg actctcgctc tactacactg cccgagcgat cttcaacgca    2940
tctgcctctg ctgctctgct ctacgctgcc cgatctactc ccttcattgc cgataacgtt    3000
ctgctccacg ctctggtttg cgccacctac atctacgtgc agggtgtcat cttctggggt    3060
ttctttaccg tcggtcacga ctgtggtcac tctgccttct cccgatacca ctccgtcaac    3120
```

```
ttcatcattg gctgcatcat gcactctgcc attctgactc ccttcgagtc ctggcgagtg    3180
acccaccgac accatcacaa gaacactggc aacattgata aggacgagat cttctaccct    3240
catcggtccg tcaaggacct ccaggacgtg cgacaatggg tctacaccct cggaggtgct    3300
tggtttgtct acctgaaggt cggatatgct cctcgaacca tgtcccactt tgaccoctgg    3360
gaccctctcc tgcttcgacg agcctccgct gtcatcgtgt ccctcggagt ctgggctgcc    3420
ttcttcgctg cctacgccta cctcacatac tcgctcggct tgccgtcat gggcctctac     3480
tactatgctc ctctctttgt ctttgcttcg ttcctcgtca ttactacctt cttgcatcac    3540
aacgacgaag ctactccctg gtacggtgac tcggagtgga cctacgtcaa gggcaacctg    3600
agctccgtcg accgatcgta cggagctttc gtggacaacc tgtctcacca cattggcacc    3660
caccaggtcc atcacttgtt ccctatcatt cccactaca agctcaacga agccaccaag    3720
cactttgctg ccgcttaccc tcacctcgtg agacgtaacg acgagcccat cattactgcc    3780
ttcttcaaga ccgctcacct ctttgtcaac tacgagctg tgcccgagac tgctcagatt     3840
ttcaccctca agagtctgc cgctgcagcc aaggccaaga gcgactaagc ggccgctatt     3900
tatcactctt tacaacttct acctcaacta tctacttta taaatgaata tcgtttattc     3960
tctatgatta ctgtatatgc gttcctctaa gacaaatcga aaccagcatg tgatcgaatg    4020
gcatacaaaa gtttcttccg aagttgatca atgtcctgat agtcaggcag cttgagaaga    4080
ttgacacagg tggaggccgt agggaaccga tcaacctgtc taccagcgtt acgaatggca    4140
aatgacgggt tcaaagcctt gaatccttgc aatggtgcct tggatactga tgtcacaaac    4200
ttaagaagca gccgcttgtc ctcttcctcg atcgatcagg agagaccggg ttggcggcgt    4260
atttgtgtcc caaaaaacag cccaattgc cccaattgac cccaaattga cccagtagcg     4320
ggcccaaccc cggcgagagc ccccttcacc ccacatatca aacctccccc ggttcccaca    4380
cttgccgtta agggcgtagg gtactgcagt ctggaatcta cgcttgttca gactttgtac    4440
tagtttcttt gtctggccat ccgggtaacc catgccggac gcaaaataga ctactgaaaa    4500
ttttttttgct ttgtggttgg gactttagcc aagggtataa aagaccaccg tccccgaatt    4560
accttttcctc ttcttttctc tctctccttg tcaactcaca cccgaaatcg ttaagcattt    4620
ccttctgagt ataagaatca ttcaccatgg ctgaggataa gaccaaggtc gagttcccta    4680
ccctgactga gctgaagcac tctatcccta acgcttgctt tgagtccaac ctcggactct    4740
cgctctacta cactgcccga gcgatcttca acgcatctgc ctctgctgct ctgctctacg    4800
ctgcccgatc tactcccttc attgccgata acgttctgct ccacgctctg gtttgcgcca    4860
cctacatcta cgtgcagggt gtcatcttct ggggtttctt taccgtcggt cacgactgtg    4920
gtcactctgc cttctcccga taccactccg tcaacttcat cattggctgc atcatgcact    4980
ctgccattct gactcccttc gagtcctggc gagtgaccca ccgacaccat cacaagaaca    5040
ctggcaacat tgataaggac gagatcttct accctcatcg gtccgtcaag gacctccagg    5100
acgtgcgaca atgggtctac accctcggag gtgcttggtt tgtctacctg aaggtcggat    5160
atgctcctcg aaccatgtcc cactttgacc cctgggaccc tctcctgctt cgacgagcct    5220
ccgctgtcat cgtgtccctc ggagtctggg ctgccttctt cgctgcctac gcctacctca    5280
catactcgct cggctttgcc gtcatgggcc tctactacta tgctcctctc tttgtctttg    5340
cttcgttcct cgtcattact accttcttgc atcacaacga cgaagctact ccctggtacg    5400
gtgactcgga gtggacctac gtcaagggca acctgagctc cgtcgaccga tcgtacgag    5460
ctttcgtgga caacctgtct caccacattg cacccacca ggtccatcac ttgttcccta    5520
```

```
tcattcccca ctacaagctc aacgaagcca ccaagcactt tgctgccgct taccctcacc    5580
tcgtgagacg taacgacgag cccatcatta ctgccttctt caagaccgct cacctctttg    5640
tcaactacgg agctgtgccc gagactgctc agattttcac cctcaaagag tctgccgctg    5700
cagccaaggc caagagcgac taagcggccg caagtgtgga tggggaagtg agtgcccggt    5760
tctgtgtgca caattggcaa tccaagatgg atggattcaa cacagggata tagcgagcta    5820
cgtggtggtg cgaggatata gcaacggata tttatgtttg acacttgaga atgtacgata    5880
caagcactgt ccaagtacaa tactaaacat actgtacata ctcatactcg tacccgggca    5940
acggtttcac ttgagtgcag tggctagtgc tcttactcgt acagtgtgca atactgcgta    6000
tcatagtctt tgatgtatat cgtattcatt catgttagtt gcgtacggtg tgtatcgtag    6060
aggtagtgac gtgttgtcca cagggcgact gtgtccgtgt atatatatat tcctcggccc    6120
gagcttattt tgtgtggggtt gaggaaatca aaccaaatcg gtagtcagag aaataaaaca    6180
aaaagaaata aaagaaata gaggacgcac aacgccatca ccgtcggaga gacaggagaa    6240
gggaaaatgg gcaaaaatgc ccttatcaca cccgcccgct tgtgctctc attcggctcc    6300 cacaagagcc tcttgtcctg gttccccccc cccacatttt aacaccccac acgacgttgc    6360
tgcacgtgga attttcggcc gaaaacctgt ggggtactta cttttggcac tggagagaag    6420
catctgggat tttgggaacc taggcagaag atgaggaaaa aaataagagg aaccgttgtg    6480
agcttgctta tcagtgtcat atactcccccc ctccttgcgt ttttgcgtct tttcccccta    6540
tttttcaaat tttgcgattt tttttctctt tttttccgct tttttccgct tttttttttgg    6600 ccggctttta tccatttctc caagccgagg atcacatcta tgcagcccag tccgttggag    6660
catatctgcg gtagagtttc ggaacggcgt taagcactgt gtccgggtcg gtctggaacg    6720
agattgagcg ggaaattcgg gggaataaga ccaccgttgg actccccgca atgaggagat    6780
caagatgtgc ttttcagaat tctgattggt ggcgcgccag ctgcattaat gaatcggcca    6840
acgcgcgggg agaggcggtt tgcgtattgg gcgctcttcc gcttcctcgc tcactgactc    6900
gctgcgctcg gtcgttcggc tgcggcgagc ggtatcagct cactcaaagg cggtaatacg    6960
gttatccaca gaatcagggg ataacgcagg aaagaacatg tgagcaaaag gccagcaaaa    7020
ggccaggaac cgtaaaaagg ccgcgttgct ggcgtttttc cataggctcc gcccccctga    7080
cgagcatcac aaaaatcgac gctcaagtca gaggtggcga aacccgacag gactataaag    7140
ataccaggcg tttccccctg gaagctccct cgtgcgctct cctgttccga ccctgccgct    7200
taccggatac ctgtccgcct ttctcccttc gggaagcgtg gcgctttctc atagctcacg    7260
ctgtaggtat ctcagttcgg tgtaggtcgt tcgctccaag ctgggctgtg tgcacgaacc    7320
ccccgttcag cccgaccgct gcgccttatc cggtaactat cgtcttgagt ccaacccggt    7380
aagacacgac ttatcgccac tggcagcagc cactggtaac aggattagca gagcgaggta    7440
tgtaggcggt gctacagagt tcttgaagtg gtggcctaac tacggctaca ctagaagaac    7500
agtatttggt atctgcgctc tgctgaagcc agttaccttc ggaaaaagag ttggtagctc    7560
ttgatccggc aaacaaacca ccgctggtag cggtggtttt tttgtttgca agcagcagat    7620
tacgcgcaga aaaaaggat ctcaagaaga tcctttgatc ttttctacgg ggtctgacgc    7680
tcagtggaac gaaaactcac gttaagggat tttggtcatg agattatcaa aaaggatctt    7740
cacctagatc cttttaaatt aaaaatgaag ttttaaatca atctaaagta tatatgagta    7800
aacttggtct gacagttacc aatgcttaat cagtgaggca cctatctcag cgatctgtct    7860
```

```
atttcgttca tccatagttg cctgactccc cgtcgtgtag ataactacga tacgggaggg    7920
cttaccatct ggccccagtg ctgcaatgat accgcgagac ccacgctcac cggctccaga    7980
tttatcagca ataaccagc cagccggaag ggccgagcgc agaagtggtc ctgcaacttt     8040
atccgcctcc atccagtcta ttaattgttg ccgggaagct agagtaagta gttcgccagt    8100
taatagtttg cgcaacgttg ttgccattgc tacaggcatc gtggtgtcac gctcgtcgtt    8160
tggtatggct tcattcagct ccggttccca acgatcaagg cgagttacat gatcccccat    8220
gttgtgcaaa aaagcggtta gctccttcgg tcctccgatc gttgtcagaa gtaagttggc    8280
cgcagtgtta tcactcatgg ttatggcagc actgcataat tctcttactg tcatgccatc    8340
cgtaagatgc ttttctgtga ctggtgagta ctcaaccaag tcattctgag aatagtgtat    8400
gcggcgaccg agttgctctt gcccggcgtc aatacgggaa ataccgcgc cacatagcag     8460
aactttaaaa gtgctcatca ttggaaaacg ttcttcgggg cgaaaactct caaggatctt    8520
accgctgttg agatccagtt cgatgtaacc cactcgtgca cccaactgat cttcagcatc    8580
ttttactttc accagcgttt ctgggtgagc aaaaacagga aggcaaaatg ccgcaaaaaa    8640
gggaataagg cgacacgga aatgttgaat actcatactc ttccttttc aatattattg      8700
aagcatttat cagggttatt gtctcatgag cggatacata tttgaatgta tttagaaaaa    8760
taaacaaata ggggttccgc gcacatttcc ccgaaaagtg ccacctgatg cggtgtgaaa    8820
taccgcacag atgcgtaagg agaaaatacc gcatcaggaa attgtaagcg ttaatatttt    8880
gttaaaattc gcgttaaatt tttgttaaat cagctcattt tttaaccaat aggccgaaat    8940
cggcaaaatc ccttataaat caaaagaata gaccgagata gggttgagtg ttgttccagt    9000
ttggaacaag agtccactat taagaacgt ggactccaac gtcaaagggc gaaaaaccgt     9060
ctatcagggc gatggcccac tacgtgaacc atcaccctaa tcaagttttt tggggtcgag    9120
gtgccgtaaa gcactaaatc ggaaccctaa agggagcccc cgatttagag cttgacgggg    9180
aaagccggcg aacgtggcga gaaggaagg gaagaaagcg aaaggagcgg gcgctagggc     9240
gctggcaagt gtagcggtca cgctgcgcgt aaccaccaca cccgccgcgc ttaatgcgcc    9300
gctacagggc gcgtccattc gccattcagg ctgcgcaact gttgggaagg gcgatcggtg    9360
cgggcctctt cgctattacg ccagctggcg aaagggggat gtgctgcaag gcgattaagt    9420
tgggtaacgc caggggtttc ccagtcacga cgttgtaaaa cgacggccag tgaattgtaa    9480
tacgactcac tatagggcga attgggcccg acgtcgcatg cgtcgagata tcgacattgt    9540
tccatctcca gtttaacccc aacttatcga gagtatttgt gagacacgca ataaatgaat    9600
ttataccaat caaatccata ttctacgctc tctacatata gatacttttt gtcatctctt    9660
gccctactat ttcgtcgata tatgaaggat acgccaaccg aacccatact ccacgctaca    9720
cacgcgcctt ttcacgcatt tctggggaaa atagacaccc ttggtgtcac ctgaagaata    9780
tgaaagaaga tattcattgt attgagctgt agatctgtgt atttcttgac ctcatcaatg    9840
acttctgggc tctttacctc gaatcatggt ggtactgtac cacatctcaa caccttgtag    9900
cacacctatg ggaaaattga gactatgaat ggattcccgt gcccgtatta ctctactaat    9960
ttgatcttgg aacgcgaaaa tacgtttcta ggactccaaa gaatctcaac tcttgtcctt   10020
actaaatata ctacccatag ttgatggttt acttgaacag agaggacatg ttcacttgac   10080
ccaaagtttc tcgcatctct tggatatttg aacaacggcg tccactgacc gtcagttatc   10140
cagtcacaaa accccacat tcatacattc ccatgtacgt ttacaaagtt ctcaattcca    10200
tcgtgcaaat caaaatcaca tctattcatt catcatatat aaacccatca tgtctactaa   10260
```

```
cactcacaac tccatagaaa acatcgactc agaacacacg ctccatctat tcctcgtcca    10320
gctcgcaaat gtcgtcatct taattaaaag gcgttgaaac agaatgagcc agacagcaag    10380
gacaaggtgg ccaacagcaa ggagtccaaa aagccctcta ttgacgagat ccacgatgtt    10440
attgctcatg aggtttccga gctcgatgct gggaagaaga agtgatttgt atataagaaa    10500
taaatgagat atagtaaagg agtgcaagag aatggcaagg tggtcaaatt ctatattact    10560
tgcagtcact ggttcctcgt tgacatgaat gaagttaccg ttggcatagc tgatttaata    10620
tataactgtc caactaactc tcacctagat ataacccatg tgtgtgtttc aatcatcaa     10680
tgcggccgct tagtcgctct tggccttggc tgcagcggca gactctttga gggtgaaaat    10740
ctgagcagtc tcgggcacag ctccgtagtt gacaaagagg tgagcggtct tgaagaaggc    10800
agtaatgatg ggctcgtcgt tacgtctcac gaggtgaggg taagcggcag caaagtgctt    10860
ggtggcttcg ttgagcttgt agtggggaat gatagggaac aagtgatgga cctggtgggt    10920
gccaatgtgg tgagacaggt tgtccacgaa agctccgtac gatcggtcga cggagctcag    10980
gttgcccttg acgtaggtcc actccgagtc accgtaccag ggagtagctt cgtcgttgtg    11040
atgcaagaag gtagtaatga cgaggaacga agcaaagaca aagagaggag catagtagta    11100
gaggcccatg acggcaaagc cgagcgagta tgtgaggtag gcgtaggcag cgaagaaggc    11160
agcccagact ccgagggaca cgatgacagc ggaggctcgt cgaagcagga gagggtccca    11220
ggggtcaaag tgggacatgg ttcgaggagc atatccgacc ttcaggtaga caaaccaagc    11280
acctccgagg gtgtagaccc attgtcgcac gtcctggagg tccttgacgg accgatgagg    11340
gtagaagatc tcgtccttat caatgttgcc agtgttcttg tgatggtgtc ggtgggtcac    11400
tcgccaggac tcgaagggag tcagaatggc agagtgcatg atgcagccaa tgatgaagtt    11460
gacggagtgg tatcgggaga aggcagagtg accacagtcg tgaccgacgg taaagaaacc    11520
ccagaagatg acaccctgca cgtagatgta ggtggcgcaa accagagcgt ggagcagaac    11580
gttatcggca atgaagggag tagatcgggc agcgtagagc agagcagcag aggcagatgc    11640
gttgaagatc gctcgggcag tgtagtagag cgagagtccg aggttggact caaagcaagc    11700
gttagggata gagtgcttca gctcagtcag ggtagggaac tcgaccttgg tcttatcctc    11760
agccatggta ccagagctgg gttagtttgt gtagagagtg tgtgttgcta gcgacttttcg   11820
gattgtgtca ttacacaaaa cgcgtcgtct cgacactgat cttgtcgtgg atactcacgg    11880
ctcggaattc tgtgatgtgt agtttagatt tcgaatctgt ggggaaagaa aggaaaaaag    11940
agactggcaa ccgattggga gagccactgt ttatatatac cctagacaag cccccccgctt   12000
gtaagatgtt ggtcaatgta aaccagtatt aaggttggca agtgcaggag aagcaaggtg    12060
tgggtaccga gcaatggaaa tgtgcggaag gcaaaaaaat gaggccacgg cctattgtcg    12120
gggctatatc caggggggcga ttgaagtaca ctaacatgac atgtgtccac agaccctcaa   12180
tctggcctga tgagccaaat ccatacgcgc tttcgcagct ctaaaggcta taacaagtca    12240
caccaccctg ctcgacctca cgcgccctcac ttttttgttaa gacaaactgt acacgctgtt  12300
ccagcgtttt ctgcctgcac ctggtgggac atttggtgca acctaaagtg ctcggaacct    12360
ctgtggtgtc cagatcagcg cagcagttcc gaggtagttt tgaggcccctt agatgatgca   12420
atggtgtcag tcgctggatc acgagtctta atggcagtat tcgttcttat ttgtgccatt    12480
gagccccgtt atcctcgtat cttctacccc ccatcccatc cctttgttgg tgcaacccta    12540
cccatttatt gttgggtgca gcccaaccga cgtggagagc ttggcttggc catataaaaa    12600
```

-continued

```
ggccccccc  tagtggcaat  ggcagaaagt  cagctgtgag  ttgttgaatt  tgtcatctag    12660
gcggcctggc  cgtcttctcc  ggggcaattt                                       12690
```

<210> SEQ ID NO 53
<211> LENGTH: 1077
<212> TYPE: DNA
<213> ORGANISM: Saprolegnia diclina
<220> FEATURE:
<221> NAME/KEY: misc_feature
<223> OTHER INFORMATION: synthetic delta-17 desaturase (codon-optimized)

<400> SEQUENCE: 53

```
atggctgagg  ataagaccaa  ggtcgagttc  cctaccctga  ctgagctgaa  gcactctatc     60
cctaacgctt  gctttgagtc  caacctcgga  ctctcgctct  actacactgc  ccgagcgatc    120
ttcaacgcat  ctgcctctgc  tgctctgctc  tacgctgccc  gatctactcc  cttcattgcc    180
gataacgttc  tgctccacgc  tctggtttgc  gccacctaca  tctacgtgca  gggtgtcatc    240
ttctggggtt  tctttaccgt  cggtcacgac  tgtggtcact  ctgccttctc  ccgataccac    300
tccgtcaact  tcatcattgg  ctgcatcatg  cactctgcca  ttctgactcc  cttcgagtcc    360
tggcgagtga  cccaccgaca  ccatcacaag  aacactggca  acattgataa  ggacgagatc    420
ttctaccctc  atcggtccgt  caaggacctc  caggacgtgc  gacaatgggt  ctacaccctc    480
ggaggtgctt  ggtttgtcta  cctgaaggtc  ggatatgctc  ctcgaaccat  gtcccacttt    540
gacccctggg  accctctcct  gcttcgacga  gcctccgctg  tcatcgtgtc  cctcggagtc    600
tgggctgcct  tcttcgctgc  ctacgcctac  ctcacatact  cgctcggctt  tgccgtcatg    660
ggcctctact  actatgctcc  tctctttgtc  tttgcttcgt  tcctcgtcat  tactaccttc    720
ttgcatcaca  cgacgaagc  tactcccctgg  tacggtgact  cggagtggac  ctacgtcaag    780
ggcaacctga  gctccgtcga  ccgatcgtac  ggagctttcg  tggacaacct  gtctcaccac    840
attggcaccc  accaggtcca  tcacttgttc  cctatcattc  cccactacaa  gctcaacgaa    900
gccaccaagc  actttgctgc  cgcttaccct  cacctcgtga  gacgtaacga  cgagcccatc    960
attactgcct  tcttcaagac  cgctcacctc  tttgtcaact  acggagctgt  gcccgagact   1020
gctcagattt  tcaccctcaa  agagtctgcc  gctgcagcca  aggccaagag  cgactaa     1077
```

<210> SEQ ID NO 54
<211> LENGTH: 358
<212> TYPE: PRT
<213> ORGANISM: Saprolegnia diclina (ATCC #56851)

<400> SEQUENCE: 54

```
Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110
```

```
Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                    165                 170                 175

Met Ser His Phe Asp Pro Trp Asp Pro Leu Leu Leu Arg Arg Ala Ser
                180                 185                 190

Ala Val Ile Val Ser Leu Gly Val Trp Ala Ala Phe Phe Ala Ala Tyr
            195                 200                 205

Ala Tyr Leu Thr Tyr Ser Leu Gly Phe Ala Val Met Gly Leu Tyr Tyr
        210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
                260                 265                 270

Phe Val Asp Asn Leu Ser His His Ile Gly Thr His Gln Val His His
            275                 280                 285

Leu Phe Pro Ile Ile Pro His Tyr Lys Leu Asn Glu Ala Thr Lys His
        290                 295                 300

Phe Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
                340                 345                 350

Ala Lys Ala Lys Ser Asp
        355

<210> SEQ ID NO 55
<211> LENGTH: 924
<212> TYPE: DNA
<213> ORGANISM: Yarrowia lipolytica
<220> FEATURE:
<221> NAME/KEY: misc_feature
<223> OTHER INFORMATION: Promoter FBAINm

<400> SEQUENCE: 55
aaattgcccc ggagaagacg gccaggccgc ctagatgaca aattcaacaa ctcacagctg      60
actttctgcc attgccacta gggggggggcc ttttttatatg gccaagccaa gctctccacg     120
tcggttgggc tgcacccaac aataaatggg tagggttgca ccaacaaagg gatgggatgg     180
ggggtagaag atacgaggat aacggggctc aatggcacaa ataagaacga atactgccat     240
taagactcgt gatccagcga ctgacaccat tgcatcatct aagggcctca aaactacctc     300
ggaactgctg cgctgatctg gacaccacag aggttccgag cactttaggt tgcaccaaat     360
gtcccaccag gtgcaggcag aaaacgctgg aacagcgtgt acagtttgtc ttaacaaaaa     420
gtgagggcgc tgaggtcgag cagggtggtg tgacttgtta tagcctttag agctgcgaaa     480
gcgcgtatgg atttggctca tcaggccaga ttgagggtct gtggacacat gtcatgttag     540
tgtacttcaa tcgccccctg gatatagccc cgacaatagg ccgtggcctc attttttttgc     600
```

| | |
|---|---|
| cttccgcaca tttccattgc tcggtaccca caccttgctt ctcctgcact tgccaacctt | 660 |
| aatactggtt tacattgacc aacatcttac aagcgggggg cttgtctagg gtatatataa | 720 |
| acagtggctc tcccaatcgg ttgccagtct cttttttcct ttctttcccc acagattcga | 780 |
| aatctaaact acacatcaca gaattccgag ccgtgagtat ccacgacaag atcagtgtcg | 840 |
| agacgacgcg ttttgtgtaa tgacacaatc cgaaagtcgc tagcaacaca cactctctac | 900 |
| acaaactaac ccagctctgg tacc | 924 |

<210> SEQ ID NO 56
<211> LENGTH: 8194
<212> TYPE: DNA
<213> ORGANISM: Artificial Sequence
<220> FEATURE:
<223> OTHER INFORMATION: Plasmid pY37/F15

<400> SEQUENCE: 56

| | |
|---|---|
| ggccgcacaa tggcgactcg acagcgaact gccaccactg ttgtggtcga ggaccttccc | 60 |
| aaggtcactc ttgaggccaa gtctgaacct gtgttcccg atatcaagac catcaaggat | 120 |
| gccattcccg cgcactgctt ccagccctcg ctcgtcacct cattctacta cgtcttccgc | 180 |
| gattttgcca tggtctctgc cctcgtctgg gctgctctca cctacatccc cagcatcccc | 240 |
| gaccagaccc tccgcgtcgc agcttggatg gtctacggct tcgtccaggg tctgttctgc | 300 |
| accggtgtct ggattctcgg ccatgagtgc ggccacggtg cttctctct ccacggaaag | 360 |
| gtcaacaatg tgaccggctg gttcctccac tcgttcctcc tcgtccccta cttcagctgg | 420 |
| aagtactctc accaccgcca ccaccgcttc accggccaca tggatctcga catggctttc | 480 |
| gtccccaaga ctgagcccaa gccctccaag tcgctcatga ttgctggcat tgacgtcgcc | 540 |
| gagcttgttg aggacacccc cgctgctcag atggtcaagc tcatcttcca ccagcttttc | 600 |
| ggatggcagg cgtacctctt cttcaacgct agctctggca agggcagcaa gcagtgggag | 660 |
| cccaagactg gcctctccaa gtggttccga gtcagtcact tcgagcctac cagcgctgtc | 720 |
| ttccgcccca acgaggccat cttcatcctc atctccgata tcggtcttgc tctaatggga | 780 |
| actgctctgt actttgcttc caagcaagtt ggtgtttcga ccattctctt cctctacctt | 840 |
| gttccctacc tgtgggttca ccactggctc gttgccatta cctacctcca ccaccaccac | 900 |
| accgagctcc ctcactacac cgctgagggc tggacctacg tcaagggagc tctcgccact | 960 |
| gtcgaccgtg agtttggctt catcggaaag cacctcttcc acggtatcat tgagaagcac | 1020 |
| gttgttcacc atctcttccc taagatcccc ttctacaagg ctgacgaggc caccgaggcc | 1080 |
| atcaagcccg tcattggcga ccactactgc acgacgacc gaagcttcct gggccagctg | 1140 |
| tggaccatct tcggcacgct caagtacgtc gagcacgacc ctgcccgacc cggtgccatg | 1200 |
| cgatggaaca aggactaggc taggcggccc ccaccgcggc ccgaattccg gcctcttcgg | 1260 |
| ccgccaagcg acccgggtgg acgtctagag gtacctagca attaacagat agtttgccgg | 1320 |
| tgataattct cttaacctcc cacactcctt tgacataacg atttatgtaa cgaaactgaa | 1380 |
| atttgaccag atattgtgtc cgcggtggag ctccagcttt tgttcccttt agtgagggtt | 1440 |
| aatttcgagc ttggcgtaat catggtcata gctgtttcct gtgtgaaatt gttatccgct | 1500 |
| cacaattcca cacaacgtac gagccggaag cataaagtgt aaagcctggg gtgcctaatg | 1560 |
| agtgagctaa ctcacattaa ttgcgttgcg ctcactgccc gctttccagt cgggaaacct | 1620 |
| gtcgtgccag ctgcattaat gaatcggcca acgcgcgggg agaggcggtt tgcgtattgg | 1680 |

```
gcgctcttcc gcttcctcgc tcactgactc gctgcgctcg gtcgttcggc tgcggcgagc    1740
ggtatcagct cactcaaagg cggtaatacg gttatccaca gaatcagggg ataacgcagg    1800
aaagaacatg tgagcaaaag gccagcaaaa ggccaggaac cgtaaaaagg ccgcgttgct    1860
ggcgtttttc cataggctcc gcccccctga cgagcatcac aaaaatcgac gctcaagtca    1920
gaggtggcga aacccgacag gactataaag ataccaggcg tttccccctg gaagctccct    1980
cgtgcgctct cctgttccga ccctgccgct taccggatac ctgtccgcct ttctcccttc    2040
gggaagcgtg gcgctttctc atagctcacg ctgtaggtat ctcagttcgg tgtaggtcgt    2100
tcgctccaag ctgggctgtg tgcacgaacc ccccgttcag cccgaccgct gcgccttatc    2160
cggtaactat cgtcttgagt ccaacccggt aagacacgac ttatcgccac tggcagcagc    2220
cactggtaac aggattagca gagcgaggta tgtaggcggt gctacagagt tcttgaagtg    2280
gtggcctaac tacggctaca ctagaaggac agtatttggt atctgcgctc tgctgaagcc    2340
agttaccttc ggaaaaagag ttggtagctc ttgatccggc aaacaaacca ccgctggtag    2400
cggtggtttt tttgtttgca agcagcagat tacgcgcaga aaaaaggat ctcaagaaga    2460
tcctttgatc ttttctacgg ggtctgacgc tcagtggaac gaaaactcac gttaagggat    2520
tttggtcatg agattatcaa aaaggatctt cacctagatc cttttaaatt aaaaatgaag    2580
ttttaaatca atctaaagta tatatgagta aacttggtct gacagttacc aatgcttaat    2640
cagtgaggca cctatctcag cgatctgtct atttcgttca tccatagttg cctgactccc    2700
cgtcgtgtag ataactacga tacgggaggg cttaccatct ggccccagtg ctgcaatgat    2760
accgcgagac ccacgctcac cggctccaga tttatcagca ataaaccagc cagccggaag    2820
ggccgagcgc agaagtggtc ctgcaacttt atccgcctcc atccagtcta ttaattgttg    2880
ccgggaagct agagtaagta gttcgccagt taatagtttg cgcaacgttg ttgccattgc    2940
tacaggcatc gtggtgtcac gctcgtcgtt tggtatggct tcattcagct ccggttccca    3000
acgatcaagg cgagttacat gatcccccat gttgtgcaaa aaagcggtta gctccttcgg    3060
tcctccgatc gttgtcagaa gtaagttggc cgcagtgtta tcactcatgg ttatggcagc    3120
actgcataat tctcttactg tcatgccatc cgtaagatgc ttttctgtga ctggtgagta    3180
ctcaaccaag tcattctgag aatagtgtat gcggcgaccg agttgctctt gcccggcgtc    3240
aatacgggat aataccgcgc cacatagcag aactttaaaa gtgctcatca ttggaaaacg    3300
ttcttcgggg cgaaaactct caaggatctt accgctgttg agatccagtt cgatgtaacc    3360
cactcgtgca cccaactgat cttcagcatc ttttactttc accagcgttt ctgggtgagc    3420
aaaaacagga aggcaaaatg ccgcaaaaaa gggaataagg gcgacacgga aatgttgaat    3480
actcatactc ttcctttttc aatattattg aagcatttat cagggttatt gtctcatgag    3540
cggatacata tttgaatgta tttagaaaaa taaacaaata ggggttccgc gcacatttcc    3600
ccgaaaagtg ccacctgacg cgccctgtag cggcgcatta agcgcggcgg gtgtggtggt    3660
tacgcgcagc gtgaccgcta cacttgccag cgccctagcg cccgctcctt tcgctttctt    3720
cccttccttt ctcgccacgt tcgccggctt tccccgtcaa gctctaaatc ggggctccc    3780
tttagggttc cgatttagtg ctttacggca cctcgacccc aaaaaacttg attagggtga    3840
tggttcacgt agtgggccat cgccctgata cggttttt cgccctttga cgttggagtc    3900
cacgttcttt aatagtggac tcttgttcca aactggaaca acactcaacc ctatctcggt    3960
ctattctttt gatttataag ggattttgcc gatttcggcc tattggttaa aaatgagct    4020
gatttaacaa aaatttaacg cgaattttaa caaaatatta acgcttacaa ttccattcg    4080
```

-continued

```
ccattcaggc tgcgcaactg ttgggaaggg cgatcggtgc gggcctcttc gctattacgc     4140
cagctggcga aaggggatg tgctgcaagg cgattaagtt gggtaacgcc agggttttcc      4200
cagtcacgac gttgtaaaac gacggccagt gaattgtaat acgactcact ataggcgaa      4260 ttgggtaccg ggccccccct cgaggtcgat ggtgtcgata agcttgatat cgaattcatg     4320
tcacacaaac cgatcttcgc ctcaaggaaa cctaattcta catccgagag actgccgaga     4380
tccagtctac actgattaat tttcgggcca ataatttaaa aaaatcgtgt tatataatat     4440
tatatgtatt atatatatac atcatgatga tactgacagt catgtcccat tgctaaatag     4500
acagactcca tctgccgcct ccaactgatg ttctcaatat ttaagggtc atctcgcatt      4560 gtttaataat aaacagactc catctaccgc ctccaaatga tgttctcaaa atatattgta     4620
tgaacttatt tttattactt agtattatta gacaacttac ttgctttatg aaaaacactt     4680
cctatttagg aaacaattta taatggcagt tcgttcattt aacaatttat gtagaataaa     4740
tgttataaat gcgtatggga atcttaaat atggatagca taaatgatat ctgcattgcc      4800
taattcgaaa tcaacagcaa cgaaaaaat cccttgtaca acataaatag tcatcgagaa      4860
atatcaacta tcaaagaaca gctattcaca cgttactatt gagattatta ttggacgaga    4920
atcacacact caactgtctt tctctcttct agaaatacag gtacaagtat gtactattct     4980
cattgttcat acttctagtc atttcatccc acatattcct tggatttctc tccaatgaat     5040
gacattctat cttgcaaatt caacaattat aataagatat accaaagtag cggtatagtg     5100
gcaatcaaaa agcttctctg gtgtgcttct cgtatttatt tttattctaa tgatccatta     5160
aaggtatata tttatttctt gttatataat ccttttgttt attacatggg ctggatacat     5220
aaaggtattt tgatttaatt ttttgcttaa attcaatccc ccctcgttca gtgtcaactg     5280
taatggtagg aaattaccat acttttgaag aagcaaaaaa aatgaaagaa aaaaaaaatc     5340
gtatttccag gttagacgtt ccgcagaatc tagaatgcgg tatgcggtac attgttcttc     5400
gaacgtaaaa gttgcgctcc ctgagatatt gtacattttt gcttttacaa gtacaagtac     5460
atcgtacaac tatgtactac tgttgatgca tccacaacag tttgttttgt tttttttgt     5520 tttttttttt tctaatgatt cattaccgct atgtatacct acttgtactt gtagtaagcc     5580
gggttattgg cgttcaatta atcatagact tatgaatctg cacggtgtgc gctgcgagtt     5640
acttttagct tatgcatgct acttgggtgt aatattggga tctgttcgga aatcaacgga     5700
tgctcaaccg atttcgacag taattaatta agtcatacac aagtcagctt tcttcgagcc     5760
tcatataagt ataagtagtt caacgtatta gcactgtacc cagcatctcc gtatcgagaa     5820
acacaacaac atgccccatt ggacagatca tgcggataca caggttgtgc agtatcatac     5880
atactcgatc agacaggtcg tctgaccatc atacaagctg aacaagcgct ccatacttgc     5940
acgctctcta tatacacagt taaattacat atccatagtc taacctctaa cagttaatct     6000
tctggtaagc ctcccagcca gccttctggt atcgcttggc ctcctcaata ggatctcggt     6060
tctggccgta cagacctcgg ccgacaatta tgatatccgt tccggtagac atgacatcct     6120
caacagttcg gtactgctgt ccgagagcgt ctcccttgtc gtcaagaccc accccggggg     6180
tcagaataag ccagtcctca gagtcgccct taggtcggtt ctgggcaatg aagccaacca     6240
caaactcggg gtcggatcgg gcaagctcaa tggtctgctt ggagtactcg ccagtggcca     6300
gagagccctt gcaagacagc tcggccagca tgagcagacc tctggccagc ttctcgttgg     6360 gagagggac taggaactcc ttgtactggg agttctcgta gtcagagacg tcctccttct     6420
```

-continued

```
tctgttcaga gacagtttcc tcggcaccag ctcgcaggcc agcaatgatt ccggttccgg      6480
gtacaccgtg ggcgttggtg atatcggacc actcggcgat tcggtgacac cggtactggt      6540
gcttgacagt gttgccaata tctgcgaact ttctgtcctc gaacaggaag aaaccgtgct      6600
taagagcaag ttccttgagg gggagcacag tgccggcgta ggtgaagtcg tcaatgatgt      6660
cgatatgggt tttgatcatg cacacataag gtccgacctt atcggcaagc tcaatgagct      6720
ccttggtggt ggtaacatcc agagaagcac acaggttggt tttcttggct gccacgagct      6780
tgagcactcg agcggcaaag gcggacttgt ggacgttagc tcgagcttcg taggagggca      6840
ttttggtggt gaagaggaga ctgaaataaa tttagtctgc agaactttt atcggaacct       6900 tatctggggc agtgaagtat atgttatggt aatagttacg agttagttga acttatagat      6960
agactggact atacggctat cggtccaaat tagaaagaac gtcaatggct ctctgggcgt      7020
cgcctttgcc gacaaaaatg tgatcatgat gaaagccagc aatgacgttg cagctgatat      7080
tgttgtcggc caaccgcgcc gaaaacgcag ctgtcagacc cacagcctcc aacgaagaat      7140
gtatcgtcaa agtgatccaa gcacactcat agttggagtc gtactccaaa ggcggcaatg      7200
acgagtcaga cagatactcg tcgacgcagt aggatgtcct gcacgggtct ttttgtgggg      7260
tgtggagaaa ggggtgcttg gagatggaag ccggtagaac cgggctgctt gtgcttggag      7320
atggaagccg gtagaaccgg gctgcttggg gggatttggg gccgctgggc tccaaagagg      7380
ggtaggcatt tcgttggggt tacgtaattg cggcatttgg gtcctgcgcg catgtcccat      7440
tggtcagaat tagtccggat aggagactta tcagccaatc acagcgccgg atccacctgt      7500
aggttgggtt gggtgggagc accctccac agagtagagt caaacagcag cagcaacatg       7560
atagttgggg gtgtgcgtgt taaaggaaaa aaaagaagct tgggttatat tcccgctcta      7620
tttagaggtt gcgggataga cgccgacgga gggcaatggc gccatggaac cttgcggata      7680
tcgatacgcc gcggcggact gcgtccgaac cagctccagc agcgtttttt ccgggccatt      7740
gagccgactg cgaccccgcc aacgtgtctt ggcccacgca ctcatgtcat gttggtgttg      7800
ggaggccact ttttaagtag cacaaggcac ctagctcgca gcaaggtgtc cgaaccaaag      7860
aagcggctgc agtggtgcaa acggggcgga aacggcggga aaaagccacg ggggcacgaa      7920
ttgaggcacg ccctcgaatt tgagacgagt cacggcccca ttcgcccgcg caatggctcg      7980
ccaacgcccg gtcttttgca ccacatcagg ttaccccaag ccaaaccttt gtgttaaaaa      8040
gcttaacata ttataccgaa cgtaggtttg ggcgggcttg ctccgtctgt ccaaggcaac      8100
atttatataa gggtctgcat cgccggctca attgaatctt ttttcttctt ctcttctcta      8160
tattcattct tgaattaaac acacatcaat ccgc                                   8194
```

<210> SEQ ID NO 57
<211> LENGTH: 10838
<212> TYPE: DNA
<213> ORGANISM: Artificial Sequence
<220> FEATURE:
<223> OTHER INFORMATION: Plasmid pKO2UF2PE
<220> FEATURE:
<221> NAME/KEY: misc_feature
<222> LOCATION: (1615)..(1618)
<223> OTHER INFORMATION: n is a, c, g, or t
<220> FEATURE:
<221> NAME/KEY: misc_feature
<222> LOCATION: (1623)..(1623)
<223> OTHER INFORMATION: n is a, c, g, or t

<400> SEQUENCE: 57

```
aaattgcccc ggagaagacg gccaggccgc ctagatgaca aattcaacaa ctcacagctg       60
```

-continued

```
actttctgcc attgccacta ggggggggcc tttttatatg gccaagccaa gctctccacg      120
tcggttgggc tgcacccaac aataaatggg tagggttgca ccaacaaagg gatgggatgg      180
ggggtagaag atacgaggat aacgggctc aatggcacaa ataagaacga atactgccat       240
taagactcgt gatccagcga ctgacaccat tgcatcatct aagggcctca aaactacctc      300
ggaactgctg cgctgatctg gacaccacag aggttccgag cactttaggt tgcaccaaat      360
gtcccaccag gtgcaggcag aaaacgctgg aacagcgtgt acagtttgtc ttaacaaaaa      420
gtgagggcgc tgaggtcgag cagggtggtg tgacttgtta tagcctttag agctgcgaaa      480
gcgcgtatgg atttggctca tcaggccaga ttgagggtct gtggacacat gtcatgttag      540
tgtacttcaa tcgcccctg gatatagccc cgacaatagg ccgtggcctc atttttttgc       600
cttccgcaca tttccattgc tcgatacccca caccttgctt ctcctgcact tgccaacctt     660
aatactggtt tacattgacc aacatcttac aagcgggggg cttgtctagg gtatatataa      720
acagtggctc tcccaatcgg ttgccagtct cttttttcct ttctttcccc acagattcga      780
aatctaaact acacatcaca gaattccgag ccgtgagtat ccgacacaag atcagtgtcg      840
agacgacgcg ttttgtgtaa tgacacaatc cgaaagtcgc tagcaacaca cactctctac      900
acaaactaac ccagctctgg taccatggcg tccacttcgg ctctgcccaa gcagaaccct      960
gcgcttagac gcaccgtcac ctcaactact gtgacggatt ctgagtctgc cgccgtctct     1020
ccttcagact ctccccgcca ctcggcctct tccacatcgc tctcgtccat gtccgaggtt     1080
gatatcgcca agcccaagtc cgagtatggt gtcatgctcg acacctacgg caaccagttc     1140
gaggttcccg actttaccat caaggacatc tacaatgcca tccctaagca ctgcttcaag     1200
cgctccgctc tcaagggata cggttatatc ctccgcgaca ttgtcctcct gactaccact     1260
ttcagcatct ggtacaactt tgtgaccccc gaatatatcc cctccacccc cgcccgcgct     1320
ggtctgtggg ccgtgtacac cgttcttcag ggtcttttcg gtactggtct ctgggttatt     1380
gcccatgagt gcggtcacgg tgctttctcc gattctcgca tcatcaacga cattactggc     1440
tgggttcttc actcttccct ccttgtcccc tacttcagct ggcaaatctc ccaccgaaag     1500
caccacaagg ccactggcaa catggagcgt gacatggtct tcgttccccg aacccgcgag     1560
cagcaggcta ctcgtctcgg aaagatgacc cacgagctcg ctcatcttac tgagnnnntc     1620
gtnggctggc ccaactacct catcaccaat gttaccggcc acaactacca cgagcgccag     1680
cgtgagggtc gcggcaaggg caagcataac ggcctcggcg tggtgttaa ccacttcgat      1740 ccccgcagcc ctctgtacga aacagtgac gctaagctca tcgtcctcag cgatattggt       1800
atcggtctga tggccactgc tctgtacttc ctcgttcaga agttcggttt ctacaacatg     1860
gccatctggt actttgttcc ctacctctgg gttaaccact ggctcgttgc catcaccttc     1920
ctccagcaca ccgaccctac ccttcccccac tacaccaacg acgagtggaa cttcgtccgt    1980
ggtgccgctg ctaccattga ccgtgagatg ggcttcatcg gccgccacct tctccacggc     2040
atcatcgaga ctcatgtcct ccaccactac gtcagcagca tccccttcta caacgcggac     2100
gaggccaccg aggccattaa gcccatcatg ggcaagcact accgggctga tgtccaggat     2160
ggtcctcgtg gcttcatccg cgccatgtac cgcagtgcgc gtatgtgcca gtgggttgag     2220
cccagcgctg gtgccgaggg tgctggtaag ggtgttctgt tcttccgcaa ccgcaacaac     2280
gtgggcaccc ccccgctgt tatcaagccc gttgcttaag taggcgcggc cgcaagtgtg      2340
gatggggaag tgagtgcccg gttctgtgtg cacaattggc aatccaagat ggatggattc     2400
```

```
aacacaggga tatagcgagc tacgtggtgg tgcgaggata tagcaacgga tatttatgtt    2460
tgacacttga gaatgtacga tacaagcact gtccaagtac aatactaaac atactgtaca    2520
tactcatact cgtacccggg caacggtttc acttgagtgc agtggctagt gctcttactc    2580
gtacagtgtg caatactgcg tatcatagtc tttgatgtat atcgtattca ttcatgttag    2640
ttgcgtacgg gtgaagcttc cactggtcgg cgtggtagtg gggcagagtg gggtcggtgt    2700
gctgcaggta ggtgatggcc acgagccagt ggttgaccca caggtagggg atcaggtagt    2760
agagggtgac ggaagccagg ccccatcggt tgatggagta tgcgatgacg gacatggtga    2820
taccaatacc gacgttagag atccagatgt tgaaccagtc cttcttctca aacagcgggg    2880
cgttggggtt gaagtggttg acagcccatt tgttgagctt ggggtacttc tgtccggtaa    2940
cgtaagacag cagatacaga ggccatccaa acacctgctg ggtgatgagg ccgtagaggg    3000
tcatgagggg agcgtcctca gcaagctcag accagtcatg ggcgcctcgg ttctccataa    3060
actcctttcg gtccttgggc acaaacacca tatcacgggt gaggtgacca gtggacttgt    3120
ggtgcatgga gtgggtcagc ttccaggcgt agtaagggac cagcatggag gagtgcagaa    3180
cccatccggt gacgttgttg acggtgttag agtcggagaa agcagagtgg ccacactcgt    3240
gggcaagaac ccacagaccg gtgccaaaca gaccctggac aatggagtac atggcccagg    3300
ccacagctcg gccggaagcc gagggaataa gaggcaggta cgcgtaggcc atgtaggcaa    3360
aaacggcgat aaagaagcag gcgcgccagc tgcattaatg aatcggccaa cgcgcgggga    3420
gaggcggttt gcgtattggg cgctcttccg cttcctcgct cactgactcg ctgcgctcgg    3480
tcgttcggct gcggcgagcg gtatcagctc actcaaaggc ggtaatacgg ttatccacag    3540
aatcagggga taacgcagga agaacatgt gagcaaaagg ccagcaaaag gccaggaacc    3600
gtaaaaaggc cgcgttgctg gcgttttttcc ataggctccg cccccctgac gagcatcaca    3660
aaaatcgacg ctcaagtcag aggtggcgaa acccgacagg actataaaga taccaggcgt    3720
ttccccctgg aagctccctc gtgcgctctc ctgttccgac cctgccgctt accggatacc    3780
tgtccgcctt tctcccttcg ggaagcgtgg cgctttctca tagctcacgc tgtaggtatc    3840
tcagttcggt gtaggtcgtt cgctccaagc tgggctgtgt gcacgaaccc cccgttcagc    3900
ccgaccgctg cgccttatcc ggtaactatc gtcttgagtc aacccggta agacacgact    3960 tatcgccact ggcagcagcc actggtaaca ggattagcag agcgaggtat gtaggcggtg    4020
ctacagagtt cttgaagtgg tggcctaact acggctacac tagaagaaca gtatttggta    4080
tctgcgctct gctgaagcca gttaccttcg gaaaaagagt tggtagctct tgatccggca    4140
aacaaaccac cgctggtagc ggtggttttt tgtttgcaa gcagcagatt acgcgcagaa    4200
aaaaaggatc tcaagaagat cctttgatct tttctacggg gtctgacgct cagtggaacg    4260
aaaactcacg ttaagggatt ttggtcatga gattatcaaa aaggatcttc acctagatcc    4320
ttttaaatta aaaatgaagt tttaaatcaa tctaaagtat atatgagtaa acttggtctg    4380
acagttacca atgcttaatc agtgaggcac ctatctcagc gatctgtcta tttcgttcat    4440
ccatagttgc ctgactcccc gtcgtgtaga taactacgat acgggagggc ttaccatctg    4500
gccccagtgc tgcaatgata ccgcgagacc cacgctcacc ggctccagat ttatcagcaa    4560
taaaccagcc agccggaagg gccgagcgca gaagtggtcc tgcaacttta tccgcctcca    4620
tccagtctat taattgttgc cgggaagcta gagtaagtag ttcgccagtt aatagtttgc    4680
gcaacgttgt tgccattgct acaggcatcg tggtgtcacg ctcgtcgttt ggtatggctt    4740
cattcagctc cggttcccaa cgatcaaggc gagttacatg atccccatg ttgtgcaaaa    4800
```

-continued

| | |
|---|---|
| aagcggttag ctccttcggt cctccgatcg ttgtcagaag taagttggcc gcagtgttat | 4860 |
| cactcatggt tatggcagca ctgcataatt ctcttactgt catgccatcc gtaagatgct | 4920 |
| tttctgtgac tggtgagtac tcaaccaagt cattctgaga atagtgtatg cggcgaccga | 4980 |
| gttgctcttg cccggcgtca atacgggata ataccgcgcc acatagcaga actttaaaag | 5040 |
| tgctcatcat tggaaaacgt tcttcggggc gaaaactctc aaggatctta ccgctgttga | 5100 |
| gatccagttc gatgtaaccc actcgtgcac ccaactgatc ttcagcatct tttactttca | 5160 |
| ccagcgtttc tgggtgagca aaaacaggaa ggcaaaatgc cgcaaaaaag gaataagggg | 5220 |
| cgacacggaa atgttgaata ctcatactct tcctttttca atattattga agcatttatc | 5280 |
| agggttattg tctcatgagc ggatacatat ttgaatgtat ttagaaaaat aaacaaatag | 5340 |
| gggttccgcg cacatttccc cgaaaagtgc cacctgatgc ggtgtgaaat accgcacaga | 5400 |
| tgcgtaagga gaaaataccg catcaggaaa ttgtaagcgt taatattttg ttaaaattcg | 5460 |
| cgttaaattt ttgttaaatc agctcatttt ttaaccaata ggccgaaatc ggcaaaatcc | 5520 |
| cttataaatc aaaagaatag accgagatag ggttgagtgt tgttccagtt tggaacaaga | 5580 |
| gtccactatt aaagaacgtg gactccaacg tcaaagggcg aaaaaccgtc tatcagggcg | 5640 |
| atggcccact acgtgaacca tcaccctaat caagtttttt ggggtcgagg tgccgtaaag | 5700 |
| cactaaatcg gaaccctaaa gggagccccc gatttagagc ttgacgggga agccggcga | 5760 |
| acgtggcgag aaaggaaggg aagaaagcga aggagcgggc gctagggcg ctggcaagtg | 5820 |
| tagcggtcac gctgcgcgta accaccacac ccgccgcgct taatgcgccg ctacagggcg | 5880 |
| cgtccattcg ccattcaggc tgcgcaactg ttgggaaggg cgatcggtgc gggcctcttc | 5940 |
| gctattacgc cagctggcga aaggggatg tgctgcaagg cgattaagtt gggtaacgcc | 6000 |
| agggttttcc cagtcacgac gttgtaaaac gacggccagt gaattgtaat acgactcact | 6060 |
| ataggcgaa ttgggcccga cgtcgcatgc ttgaatctac aagtaggagg gttggagtga | 6120 |
| ttaagtgaaa cttctttaac ggctctatgc cagttctatt gatatccgaa acatcagtat | 6180 |
| gaaggtctga taagggtgac ttcttcccac agattcgtat cagtacgagt acgagaccgg | 6240 |
| tacttgtaac agtattgata ctaaagggaa actacaacgg ttgtcagcgt aatgtgactt | 6300 |
| cgcccatgaa cgcagacacg cagtgccgag tgcggtgata tcgcctactc gttacgtcca | 6360 |
| tggactacac aaccccctcgg cttcgcttgg cttagcctcg ggctcggtgc tgttcagtta | 6420 |
| aaacacaatc aaataacatt tctacttttt agaaggcagg ccgtcaggag caactccgac | 6480 |
| tccattgacg tttctaaaca tctgaatgcc ttccttacct tcaacaaact ggcaggttcg | 6540 |
| ggcgacagtg taaagagact tgatgaagtt ggtgtcgtcg tgtcggtagt gcttgcccat | 6600 |
| gaccttcttg atcttctcag tggcgattcg ggcgttgtag aagggaattc cgtcgtcgcc | 6660 |
| tgagtcgacg agtatctgtc tgactcgtca ttgccgcctt tggagtacga ctccaactat | 6720 |
| gagtgtgctt ggatcacttt gacgatacat tcttcgttgg aggctgtggg tctgacagct | 6780 |
| gcgttttcgg cgcggttggc cgacaacaat atcagctgca acgtcattgc tggctttcat | 6840 |
| catgatcaca ttttttgtcgg caaaggcgac gcccagagag ccattgacgt tctttctaat | 6900 |
| ttggaccgat agccgtatag tccagtctat ctataagttc aactaactcg taactattac | 6960 |
| cataacatat acttcactgc cccagataag gttccgataa aaagttctgc agactaaatt | 7020 |
| tatttcagtc tcctcttcac caccaaaatg ccctcctacg aagctcgagc taacgtccac | 7080 |
| aagtccgcct ttgccgctcg agtgctcaag ctcgtggcag ccaagaaaac caacctgtgt | 7140 |

```
gcttctctgg atgttaccac caccaaggag ctcattgagc ttgccgataa ggtcggacct    7200
tatgtgtgca tgatcaaaac ccatatcgac atcattgacg acttcaccta cgccggcact    7260
gtgctccccc tcaaggaact tgctcttaag cacggtttct tcctgttcga ggacagaaag    7320
ttcgcagata ttggcaacac tgtcaagcac cagtaccggt gtcaccgaat cgccgagtgg    7380
tccgatatca ccaacgccca cggtgtaccc ggaaccggaa tcattgctgg cctgcgagct    7440
ggtgccgagg aaactgtctc tgaacagaag aaggaggacg tctctgacta cgagaactcc    7500
cagtacaagg agttcctagt cccctctccc aacgagaagc tggccagagg tctgctcatg    7560
ctggccgagc tgtcttgcaa gggctctctg gccactggcg agtactccaa gcagaccatt    7620
gagcttgccc gatccgaccc cgagtttgtg gttggcttca ttgcccagaa ccgacctaag    7680
ggcgactctg aggactggct tattctgacc cccggggtgg gtcttgacga caagggagac    7740
gctctcggac agcagtaccg aactgttgag gatgtcatgt ctaccggaac ggatatcata    7800
attgtcggcc gaggtctgta cggccagaac cgagatccta ttgaggaggc caagcgatac    7860
cagaaggctg gctgggaggc ttaccagaag attaactgtt agaggttaga ctatggatat    7920
gtaatttaac tgtgtatata gagagcgtgc aagtatggag cgcttgttca gcttgtatga    7980
tggtcagacg acctgtctga tcgagtatgt atgatactgc acaacctgtg tatccgcatg    8040
atctgtccaa tggggcatgt tgttgtgttt ctcgatacgg agatgctggg tacagtgcta    8100
atacgttgaa ctacttatac ttatatgagg ctcgaagaaa gctgacttgt gtatgactta    8160
attaatttga atcgaatcga tgagcctaaa atgaacccga gtatatctca taaaattctc    8220
ggtgagaggt ctgtgactgt cagtacaagg tgccttcatt atgccctcaa ccttaccata    8280
cctcactgaa tgtagtgtac ctctaaaaat gaaatacagt gccaaaagcc aaggcactga    8340
gctcgtctaa cggacttgat atacaaccaa ttaaaacaaa tgaaagaaa tacagttctt    8400 tgtatcattt gtaacaatta ccctgtacaa actaaggtat tgaaatccca caatattccc    8460
aaagtccacc cctttccaaa ttgtcatgcc tacaactcat ataccaagca ctaacctacc    8520
gtttaaacag tgtacgcaga tcccgtcaac agttttatat atcgtagtta caaccatcaa    8580
cactttttgg taagtgtacc attctatact ccaactggtc tgcaactgta caagtagaca    8640
tgttaatggt agttaataac atctacagca gaacctatgg taaagacatt gcattttttac    8700 aggaagtatc gtcctacacg ttgataaatc caaagatgcg gaacttcttc cacttttatc    8760
atcatcccct actcgtacac tcgtactctt tgttcgatcg cgattcattt ctataaataa    8820
tcttgtatgt acatgcggcc gcttactgga gcttctggcc cttctccttg gcagcgtcag    8880
ccttggcctg cttggcgagc ttggcgttct ttcggtaaaa gttgtagaag agaccgagca    8940
tggtccacat gtagaaccag agcagagcgg tgatgaagaa ggggtatcca ggtcggccaa    9000
ggaccttcat ggcgtacatg tcccaggaag actggacaga catcatgcag aactgggtca    9060
tctgggatcg agtgatgtag aacttgatga acgacacctg cttgaagccc agggcagaca    9120
gaaagtagta gccgtacatg atgacgtgga tgaaggagtt cagggcagca gagaagtagg    9180
cttcaccgtt gggagcaacg aaggtgacca gccaccagat ggtgaagatg gaagagtggt    9240
ggtacacgtg cagaaaggaa atctgtcggt tgttcttctt gaggaccatg atcatggtgt    9300
cgacaaactc catgatcttg gagaagtaga agagccagat catcttagcc ataggggagac    9360 ccttgaaggt gtgatcggca gcgttctcaa acagtccata gttggcctga taagcctcgt    9420
acaggatgcc accgcacatg taggcggaga tggagaccag acagaagttg tgcaggaggg    9480
agaaggtctt gacctcgaat cgttcaaagt tcttcatgat ctgcataccc acaaacacgg    9540
```

-continued

```
tgaccaggta ggcgagcacg atcaggagca cgtggaaggg gttcatcaga ggcagctctc      9600
gagccagggg agactccacg gcaaccagga agcctcgagt gtgatggaca atggtgggaa      9660
tgtacttctc ggcctgggca accagggcag cctccagggg atcgacgtag ggagcagctc      9720
ggacaccgat agcgctggcg aggtccatga acaggtcctg aggcatcttg gagggcagga      9780
agggagcaat ggactccatg gttagcgtgt cgtgttttg ttgtgctgga agaaccaaag       9840
ggtggcgcaa tgtgtgtaga tatatatgtc gtgacccaca agtcacacaa acaagtatcg      9900
ggaggagtgg tgcacctcta tgcggagaaa ccttataccg ctgtagacca actggggcag      9960
aggtgtgagt tgaagtcagc tggaggagat gtgtgacaga agcacaagaa gtgagattgt      10020
gagatgtatg tctagggggg gaagttttgt gtcaaatata tgggaattat tatcagcacc      10080
acgaaattat acgcctcata tgacccattt aggtggatag atcatggaca ctgttgacag      10140
ctgcgaagaa aaagcgtatt ggggatgatc cgaaattagt ccggtaccga ggcgcaaata      10200
cgtaagacag ccgatwaaat atatgcgaga acaccaaag agactctaga tgtttgtttg       10260
gcacagtttt gacttctgcg aaggccttac accaccttgt tgacccttgt cgcgggtcgg      10320
gcaatatcgg ctgacagagt tttacttgct caataagata cgagctgcat agagttgaac      10380
tacaggacaa tattggggct ggccacatga agggcattgt ttggaggtgt attgatggtg      10440
aaaacacgat atgaaatgac aacgccccct gttttattat tattcttatt attttgggtg      10500
cttctctatc catacaagca cctcctaaca tgcttcataa gtgacctcct catcacaagg      10560
cctgaggtct catttatcca gtggcgccaa gctaaactaa aactggtccg agtagactaa      10620
ggcgaagaga gaaggagaga agacagtttt tttgtggccg cctgtgaaca atgaaaacga      10680
tgagggtgag atggagcaaa ccatatggac agtcagagga gtacacgctg cttacataat      10740
ggcgcaacga ccacatgtcc cacagatacg cattatgcct gtacatattc cgggggaggt      10800
atgtaccagt agttcgcctg ctaccgttag ctacatttt                            10838
```

<210> SEQ ID NO 58
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<223> OTHER INFORMATION: delta-12 desaturase

<400> SEQUENCE: 58

```
cgtagttata tacaagaggt agatgcgtgc tggtgttaga ggggctctca ggattaggag       60
gaaaatttga cattggccct caacatataa cctcgggtgt gcctctgttt accctcagct      120
tttgcttgtc cccaagtcag tcacgccagg ccaaaaaggt tggtggattg acagggagaa      180
aaaaaaaagc ctagtggggtt taaactcgag gtaagacatt gaaatatata ccggtcggca      240
tcctgagtcc ctttctcgta ttccaacaga ccgaccatag aa atg gat tcg acc         294
                                                 Met Asp Ser Thr
                                                  1 acg cag acc aac acc ggc acc ggc aag gtg gcc gtg cag ccc ccc acg      342
Thr Gln Thr Asn Thr Gly Thr Gly Lys Val Ala Val Gln Pro Pro Thr
  5                  10                  15                  20 gcc ttc att aag ccc att gag aag gtg tcc gag ccc gtc tac gac acc      390
Ala Phe Ile Lys Pro Ile Glu Lys Val Ser Glu Pro Val Tyr Asp Thr
              25                  30                  35 ttt ggc aac gag ttc act cct cca gac tac tct atc aag gat att ctg      438
Phe Gly Asn Glu Phe Thr Pro Pro Asp Tyr Ser Ile Lys Asp Ile Leu
```

```
                  40              45              50
gat gcc att ccc cag gag tgc tac aag cgg tcc tac gtt aag tcc tac     486
Asp Ala Ile Pro Gln Glu Cys Tyr Lys Arg Ser Tyr Val Lys Ser Tyr
            55              60              65 tcg tac gtg gcc cga gac tgc ttc ttt atc gcc gtt ttt gcc tac atg     534
Ser Tyr Val Ala Arg Asp Cys Phe Phe Ile Ala Val Phe Ala Tyr Met
 70              75              80 gcc tac gcg tac ctg cct ctt att ccc tcg gct tcc ggc cga gct gtg     582
Ala Tyr Ala Tyr Leu Pro Leu Ile Pro Ser Ala Ser Gly Arg Ala Val
 85              90              95             100 gcc tgg gcc atg tac tcc att gtc cag ggt ctg ttt ggc acc ggt ctg     630
Ala Trp Ala Met Tyr Ser Ile Val Gln Gly Leu Phe Gly Thr Gly Leu
                105             110             115 tgg gtt ctt gcc cac gag tgt ggc cac tct gct ttc tcc gac tct aac     678
Trp Val Leu Ala His Glu Cys Gly His Ser Ala Phe Ser Asp Ser Asn
                120             125             130 acc gtc aac aac gtc acc gga tgg gtt ctg cac tcc tcc atg ctg gtc     726
Thr Val Asn Asn Val Thr Gly Trp Val Leu His Ser Ser Met Leu Val
            135             140             145 cct tac tac gcc tgg aag ctg acc cac tcc atg cac cac aag tcc act     774
Pro Tyr Tyr Ala Trp Lys Leu Thr His Ser Met His His Lys Ser Thr
150             155             160 ggt cac ctc acc cgt gat atg gtg ttt gtg ccc aag gac cga aag gag     822
Gly His Leu Thr Arg Asp Met Val Phe Val Pro Lys Asp Arg Lys Glu
165             170             175             180 ttt atg gag aac cga ggc gcc cat gac tgg tct gag ctt gct gag gac     870
Phe Met Glu Asn Arg Gly Ala His Asp Trp Ser Glu Leu Ala Glu Asp
                185             190             195 gct ccc ctc atg acc ctc tac ggc ctc atc acc cag cag gtg ttt gga     918
Ala Pro Leu Met Thr Leu Tyr Gly Leu Ile Thr Gln Gln Val Phe Gly
                200             205             210 tgg cct ctg tat ctg ctg tct tac gtt acc gga cag aag tac ccc aag     966
Trp Pro Leu Tyr Leu Leu Ser Tyr Val Thr Gly Gln Lys Tyr Pro Lys
            215             220             225 ctc aac aaa tgg gct gtc aac cac ttc aac ccc aac gcc ccg ctg ttt    1014
Leu Asn Lys Trp Ala Val Asn His Phe Asn Pro Asn Ala Pro Leu Phe
230             235             240 gag aag aag gac tgg ttc aac atc tgg atc tct aac gtc ggt att ggt    1062
Glu Lys Lys Asp Trp Phe Asn Ile Trp Ile Ser Asn Val Gly Ile Gly
245             250             255             260 atc acc atg tcc gtc atc gca tac tcc atc aac cga tgg ggc ctg gct    1110
Ile Thr Met Ser Val Ile Ala Tyr Ser Ile Asn Arg Trp Gly Leu Ala
                265             270             275 tcc gtc acc ctc tac tac ctg atc ccc tac ctg tgg gtc aac cac tgg    1158
Ser Val Thr Leu Tyr Tyr Leu Ile Pro Tyr Leu Trp Val Asn His Trp
                280             285             290 ctc gtg gcc atc acc tac ctg cag cac acc gac ccc act ctg ccc cac    1206
Leu Val Ala Ile Thr Tyr Leu Gln His Thr Asp Pro Thr Leu Pro His
            295             300             305 tac cac gcc gac cag tgg aac ttc acc cga gga gcc gcc gcc acc atc    1254
Tyr His Ala Asp Gln Trp Asn Phe Thr Arg Gly Ala Ala Ala Thr Ile
310             315             320 gac cga gag ttt ggc ttc atc ggc tcc ttc tgc ttc cat gac atc atc    1302
Asp Arg Glu Phe Gly Phe Ile Gly Ser Phe Cys Phe His Asp Ile Ile
325             330             335             340 gag acc cac gtt ctg cac cac tac gtg tct cga att ccc ttc tac aac    1350
Glu Thr His Val Leu His His Tyr Val Ser Arg Ile Pro Phe Tyr Asn
                345             350             355 gcc cga atc gcc act gag aag atc aag aag gtc atg ggc aag cac tac    1398
Ala Arg Ile Ala Thr Glu Lys Ile Lys Lys Val Met Gly Lys His Tyr
```

-continued

| | | | | | | | | | | | | |
|---|---|---|---|---|---|---|---|---|---|---|---|---|
| Ala | Arg | Ile | Ala | Thr | Glu | Lys | Ile | Lys | Lys | Val | Met | Gly | Lys | His | Tyr |
| | | 360 | | | | | 365 | | | | | 370 | | | |

```
cga cac gac gac acc aac ttc atc aag tct ctt tac act gtc gcc cga     1446
Arg His Asp Asp Thr Asn Phe Ile Lys Ser Leu Tyr Thr Val Ala Arg
        375                 380                 385 acc tgc cag ttt gtt gaa ggt aag gaa ggc att cag atg ttt aga aac     1494
Thr Cys Gln Phe Val Glu Gly Lys Glu Gly Ile Gln Met Phe Arg Asn
390                 395                 400 gtc aat gga gtc gga gtt gct cct gac ggc ctg cct tct aaa aag         1539
Val Asn Gly Val Gly Val Ala Pro Asp Gly Leu Pro Ser Lys Lys
405                 410                 415 tagagctaga aatgttattt gattgtgttt taactgaaca gcaccgagcc cgaggctaag   1599
ccaagcgaag ccgaggggtt gtgtagtcca tggacgtaac gagtaggcga tatcaccgca   1659
ctcggcactg cgtgtctgcg ttcatgggcg aagtcacatt acgctgacaa ccgttgtagt   1719
ttccctttag tatcaatact gttacaagta ccggtctcgt actcgtactg atacgaatct   1779
gtgggaagaa gtcacccttA tcagaccttc atactgatgt ttcggatatc aatagaactg   1839
gcatagagcc gttaaagaag tttcacttaa tcactccaac cctcctactt gtagattcaa   1899
gcagatcgat aagatggatt tgatggtcag tgctagc                            1936
```

<210> SEQ ID NO 59
<211> LENGTH: 419
<212> TYPE: PRT
<213> ORGANISM: Yarrowia lipolytica

<400> SEQUENCE: 59

```
Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
                20                  25                  30

Val Tyr Asp Thr Phe Gly Asn Glu Phe Thr Pro Pro Asp Tyr Ser Ile
            35                  40                  45

Lys Asp Ile Leu Asp Ala Ile Pro Gln Glu Cys Tyr Lys Arg Ser Tyr
        50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220
```

-continued

```
Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
            245                 250                 255

Val Gly Ile Gly Ile Thr Met Ser Val Ile Ala Tyr Ser Ile Asn Arg
        260                 265                 270

Trp Gly Leu Ala Ser Val Thr Leu Tyr Tyr Leu Ile Pro Tyr Leu Trp
    275                 280                 285

Val Asn His Trp Leu Val Ala Ile Thr Tyr Leu Gln His Thr Asp Pro
290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 60
<211> LENGTH: 1130
<212> TYPE: DNA
<213> ORGANISM: Yarrowia lipolytica
<220> FEATURE:
<221> NAME/KEY: misc_feature
<223> OTHER INFORMATION: GPAT promoter

<400> SEQUENCE: 60
caacttttct tgtcgacctg agataccgag gttgcgcagg ggatcaactt ttgtgtctca      60
gagggaccca agtgcgtacg gagagtacag tacatactgt agctaacggt agcaggcgaa     120
ctactggtac atacctcccc cggaatatgt acaggcataa tgcgtatctg tgggacatgt     180
ggtcgttgcg ccattatgta agcagcgtgt actcctctga ctgtccatat ggtttgctcc     240
atctcaccct catcgttttc attgttcaca ggcggccaca aaaaaactgt cttctctcct     300
tctctcttcg ccttagtcta ctcggaccag ttttagttta gcttggcgcc actggataaa     360
tgagacctca ggccttgtga tgaggaggtc acttatgaag catgttagga ggtgcttgta     420
tggatagaga agcacccaaa ataataagaa taataataaa acaggggggcg ttgtcatttc     480 atatcgtgtt ttcaccatca atacacctcc aaacaatgcc cttcatgtgg ccagccccaa     540
tattgtcctg tagttcaact ctatgcagct cgtatcttat tgagcaagta aaactctgtc     600
agccgatatt gcccgacccg cgacaagggt caacaaggtg gtgtaaggcc ttcgcagaag     660
tcaaaactgt gccaaacaaa catctagagt ctctttggtg tttctcgcat atatttaatc     720
ggctgtctta cgtatttggc ctcggtaccg gactaatttc ggatcatccc caatacgctt     780
tttcttcgca gctgtcaaca gtgtccatga tctatccacc taaatgggtc atatgaggcg     840
tataatttcg tggtgctgat aataattccc atatatttga cacaaaactt ccccccctag     900
```

| | |
|---|---:|
| acatacatct cacaatctca cttcttgtgc ttctgtcaca catctcctcc agctgacttc | 960 |
| aactcacacc tctgccccag ttggtctaca gcggtataag gtttctccgc atagaggtgc | 1020 |
| accactcctc ccgatacttg tttgtgtgac ttgtgggtca cgacatatat atctacacac | 1080 |
| attgcgccac cctttggttc ttccagcaca acaaaaacac gacacgctaa | 1130 |

<210> SEQ ID NO 61
<211> LENGTH: 5833
<212> TYPE: DNA
<213> ORGANISM: Artificial Sequence
<220> FEATURE:
<223> OTHER INFORMATION: Plasmid pZKUT16

<400> SEQUENCE: 61

| | |
|---|---:|
| gtacgaggaa actgtctctg aacagaagaa ggaggacgtc tctgactacg agaactccca | 60 |
| gtacaaggag ttcctagtcc cctctcccaa cgagaagctg gccagaggtc tgctcatgct | 120 |
| ggccgagctg tcttgcaagg gctctctggc cactggcgag tactccaagc agaccattga | 180 |
| gcttgcccga tccgaccccg agtttgtggt tggcttcatt gcccagaacc gacctaaggg | 240 |
| cgactctgag gactggctta ttctgacccc cggggtgggt cttgacgaca agggagacgc | 300 |
| tctcggacag cagtaccgaa ctgttgagga tgtcatgtct accggaacgg atatcataat | 360 |
| tgtcggccga ggtctgtacg gccagaaccg agatcctatt gaggaggcca agcgatacca | 420 |
| gaaggctggc tgggaggctt accagaagat taactgttag aggttagact atggatatgt | 480 |
| aatttaactg tgtatataga gagcgtgcaa gtatggagcg cttgttcagc ttgtatgatg | 540 |
| gtcagacgac ctgtctgatc gagtatgtat gatactgcac aacctgtgta tccgcatgat | 600 |
| ctgtccaatg gggcatgttg ttgtgttttct cgatacggag atgctgggta cagtgctaat | 660 |
| acgttgaact acttatactt atatgaggct cgaagaaagc tgacttgtgt atgacttaat | 720 |
| taatcgagct tggcgtaatc atggtcatag ctgtttcctg tgtgaaattg ttatccgctc | 780 |
| acaattccac acaacatacg agccggaagc ataaagtgta aagcctgggg tgcctaatga | 840 |
| gtgagctaac tcacattaat tgcgttgcgc tcactgcccg ctttccagtc gggaaacctg | 900 |
| tcgtgccagc tgcattaatg aatcggccaa cgcgcgggga gaggcggttt gcgtattggg | 960 |
| cgctcttccg cttcctcgct cactgactcg ctgcgctcgg tcgttcggct gcggcgagcg | 1020 |
| gtatcagctc actcaaaggc ggtaatacgg ttatccacag aatcagggga taacgcagga | 1080 |
| aagaacatgt gagcaaaagg ccagcaaaag gccaggaacc gtaaaaaggc cgcgttgctg | 1140 |
| gcgtttttcc ataggctccg ccccccctgac gagcatcaca aaaatcgacg ctcaagtcag | 1200 |
| aggtggcgaa acccgacagg actataaaga taccaggcgt ttccccctgg aagctccctc | 1260 |
| gtgcgctctc ctgttccgac cctgccgctt accggatacc tgtccgcctt tctcccttcg | 1320 |
| ggaagcgtgg cgctttctca tagctcacgc tgtaggtatc tcagttcggt gtaggtcgtt | 1380 |
| cgctccaagc tgggctgtgt gcacgaaccc cccgttcagc ccgaccgctg cgccttatcc | 1440 |
| ggtaactatc gtcttgagtc aacccggta agacacgact tatcgccact ggcagcagcc | 1500 |
| actggtaaca ggattagcag agcgaggtat gtaggcggtg ctacagagtt cttgaagtgg | 1560 |
| tggcctaact acggctacac tagaaggaca gtatttggta tctgcgctct gctgaagcca | 1620 |
| gttaccttcg gaaaaagagt tggtagctct tgatccggca acaaaccac cgctggtagc | 1680 |
| ggtggttttt tgtttgcaa gcagcagatt acgcgcagaa aaaaggatc tcaagaagat | 1740 |
| cctttgatct tttctacggg gtctgacgct cagtggaacg aaaactcacg ttaagggatt | 1800 |
| ttggtcatga gattatcaaa aaggatcttc acctagatcc ttttaaatta aaaatgaagt | 1860 |

```
tttaaatcaa tctaaagtat atatgagtaa acttggtctg acagttacca atgcttaatc    1920
agtgaggcac ctatctcagc gatctgtcta tttcgttcat ccatagttgc ctgactcccc    1980
gtcgtgtaga taactacgat acgggagggc ttaccatctg gccccagtgc tgcaatgata    2040
ccgcgagacc cacgctcacc ggctccagat ttatcagcaa taaaccagcc agccggaagg    2100
gccgagcgca gaagtggtcc tgcaacttta tccgcctcca tccagtctat taattgttgc    2160
cgggaagcta gagtaagtag ttcgccagtt aatagtttgc gcaacgttgt tgccattgct    2220
acaggcatcg tggtgtcacg ctcgtcgttt ggtatggctt cattcagctc cggttcccaa    2280
cgatcaaggc gagttacatg atcccccatg ttgtgcaaaa aagcggttag ctccttcggt    2340
cctccgatcg ttgtcagaag taagttggcc gcagtgttat cactcatggt tatggcagca    2400
ctgcataatt ctcttactgt catgccatcc gtaagatgct tttctgtgac tggtgagtac    2460
tcaaccaagt cattctgaga atagtgtatg cggcgaccga gttgctcttg cccggcgtca    2520
atacgggata ataccgcgcc acatagcaga actttaaaag tgctcatcat tggaaaacgt    2580
tcttcggggc gaaaactctc aaggatctta ccgctgttga gatccagttc gatgtaaccc    2640
actcgtgcac ccaactgatc ttcagcatct tttactttca ccagcgtttc tgggtgagca    2700
aaaacaggaa ggcaaaatgc cgcaaaaaag gaataagggc gacacggaaa atgttgaata    2760
ctcatactct tcctttttca atattattga agcatttatc agggttattg tctcatgagc    2820
ggatacatat ttgaatgtat ttagaaaaat aaacaaatag gggttccgcg cacatttccc    2880
cgaaaagtgc cacctgacgc gccctgtagc ggcgcattaa gcgcggcggg tgtggtggtt    2940
acgcgcagcg tgaccgctac acttgccagc gccctagcgc ccgctccttt cgctttcttc    3000
ccttcctttc tcgccacgtt cgccggcttt ccccgtcaag ctctaaatcg ggggctccct    3060
ttagggttcc gatttagtgc tttacggcac ctcgacccca aaaaacttga ttagggtgat    3120
ggttcacgta gtgggccatc gccctgatag acggtttttc gccctttgac gttggagtcc    3180
acgttcttta atagtggact cttgttccaa actggaacaa cactcaaccc tatctcggtc    3240
tattcttttg atttataagg gattttgccg atttcggcct attggttaaa aaatgagctg    3300
atttaacaaa aatttaacgc gaattttaac aaaatattaa cgcttacaat ttccattcgc    3360
cattcaggct gcgcaactgt tgggaagggc gatcggtgcg ggcctcttcg ctattacgcc    3420
agctggcgaa aggggggatgt gctgcaaggc gattaagttg ggtaacgcca gggttttccc    3480
agtcacgacg ttgtaaaacg acggccagtg aattgtaata cgactcacta tagggcgaat    3540
tgggtaccgg gccccccctc gaggtcgacg agtatctgtc tgactcgtca ttgccgcctt    3600
tggagtacga ctccaactat gagtgtgctt ggatcacttt gacgatacat tcttcgttgg    3660
aggctgtggg tctgacagct gcgttttcgg cgcggttggc cgacaacaat atcagctgca    3720
acgtcattgc tggctttcat catgatcaca tttttgtcgg caaaggcgac gcccagagag    3780
ccattgacgt tctttctaat ttggaccgat agccgtatag tccagtctat ctataagttc    3840
aactaactcg taactattac cataacatat acttcactgc cccagataag gttccgataa    3900
aaagttctgc agactaaatt tatttcagtc tcctcttcac caccaaaatg ccctcctacg    3960
aagctcgagt gctcaagctc gtggcagcca agaaaaccaa cctgtgtgct tctctggatg    4020
ttaccaccac caaggagctc attgagcttg ccgataaggt cggaccttat gtgtgcatga    4080
tcaaaaccca tatcgacatc attgacgact caccctacgc cggcactgtg ctccccctca    4140
aggaacttgc tcttaagcac ggtttcttcc tgttcgagga cagaaagttc gcagatattg    4200
```

-continued

```
gcaacactgt caagcaccag taccggtgtc accgaatcgc cgagtggtcc gatatcacca    4260
acgcccacgg tgtacccgga accggaatcg atgcagaatt caggagagac cgggttggcg    4320
gcgtatttgt gtcccaaaaa acagcccaa ttgccccaat tgaccccaaa ttgacccagt    4380
agcgggccca accccggcga gagccccctt caccccacat atcaaacctc ccccggttcc    4440
cacacttgcc gttaagggcg tagggtactg cagtctggaa tctacgcttg ttcagacttt    4500
gtactagttt ctttgtctgg ccatccgggt aacccatgcc ggacgcaaaa tagactactg    4560
aaaatttttt tgctttgtgg ttgggacttt agccaagggt ataaaagacc accgtccccg    4620
aattaccttt cctcttcttt tctctctctc cttgtcaact cacacccgaa atcgttaagc    4680
atttccttct gagtataaga atcattcacc atggacatgt ccgtcctgac tctccaagag    4740
tacgagttcg agaagcagtt caacgagaat gaagccatcc aatggatgca ggaaaactgg    4800
aagaaatcct tcctgttttc tgccctctac gctgccttta tctttggtgg acgacatctg    4860
atgaacaagc gagccaagtt tgagctgcga aaacctctcg tgctctggtc cctgaccctc    4920
gctgtcttct ctatcttcgg tgctctgcga actggagcct acatgctcta catcctgatg    4980
accaaaggcc tgaaacagtc tgtttgtgac cagtcctttt acaacggacc cgtctcgaaa    5040
ttctgggctt acgcctttgt gctctccaaa gctcccgaac ttggcgatac catcttcatc    5100
attctgcgaa agcagaaact catcttcctg cactggtatc accacatcac cgtcctcctg    5160
tactcttggt actcctacaa ggacatggtg gctggaggtg gctggttcat gactatgaac    5220
tacggtgtcc acgccgtgat gtactcctac tacgccctcc gagctgccgg tttccgagtc    5280
tctcgaaagt ttgccatgtt catcaccctg tcgcagatca ctcagatgct catgggctgt    5340
gtcattaact acctggtctt caactggatg cagcatgaca atgaccagtg ctactcccac    5400
tttcagaaca tcttctggtc ctctctcatg tacctctcct accttctgct cttctgccat    5460 tcttctttg aggcctacat tggcaaagtg aagaaagcca ccaaggctga gtaagcggcc    5520
gcaagtgtgg atggggaagt gagtgcccgg ttctgtgtgc acaattggca atccaagatg    5580
gatggattca acacagggat atagcgagct acgtggtggt gcgaggatat agcaacggat    5640
atttatgttt gacacttgag aatgtacgat acaagcactg tccaagtaca atactaaaca    5700
tactgtacat actcatactc gtacccgggc aacggtttca cttgagtgca gtggctagtg    5760
ctcttactcg tacagtgtgc aatactgcgt atcatagtct ttgatgtata tcgtattcat    5820
tcatgttagt tgc                                                       5833
```

```
<210> SEQ ID NO 62
<211> LENGTH: 804
<212> TYPE: DNA
<213> ORGANISM: Rattus norvegicus
<220> FEATURE:
<221> NAME/KEY: misc_feature
<223> OTHER INFORMATION: synthetic C16 elongase (codon-optimized)

<400> SEQUENCE: 62
```

```
atggacatgt ccgtcctgac tctccaagag tacgagttcg agaagcagtt caacgagaat      60
gaagccatcc aatggatgca ggaaaactgg aagaaatcct tcctgttttc tgccctctac     120
gctgccttta tctttggtgg acgacatctg atgaacaagc gagccaagtt tgagctgcga     180
aaacctctcg tgctctggtc cctgaccctc gctgtcttct ctatcttcgg tgctctgcga     240
actggagcct acatgctcta catcctgatg accaaaggcc tgaaacagtc tgtttgtgac     300
cagtcctttt acaacggacc cgtctcgaaa ttctgggctt acgcctttgt gctctccaaa     360
```

```
gctcccgaac ttggcgatac catcttcatc attctgcgaa agcagaaact catcttcctg      420
cactggtatc accacatcac cgtcctcctg tactcttggt actcctacaa ggacatggtg      480
gctggaggtg gctggttcat gactatgaac tacggtgtcc acgccgtgat gtactcctac      540
tacgccctcc gagctgccgg tttccgagtc tctcgaaagt ttgccatgtt catcaccctg      600
tcgcagatca ctcagatgct catgggctgt gtcattaact acctggtctt caactggatg      660
cagcatgaca atgaccagtg ctactcccac tttcagaaca tcttctggtc ctctctcatg      720
tacctctcct accttctgct cttctgccat ttcttctttg aggcctacat tggcaaagtg      780
aagaaagcca ccaaggctga gtaa                                              804
```

<210> SEQ ID NO 63
<211> LENGTH: 267
<212> TYPE: PRT
<213> ORGANISM: Rattus norvegicus (GenBank Accession No. AB071986)

<400> SEQUENCE: 63

```
Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Leu Tyr Ile Leu Met Thr Lys Gly Leu Lys Gln
                85                  90                  95

Ser Val Cys Asp Gln Ser Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe His Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Ile Asn Tyr Leu Val Phe Asn Trp Met Gln His Asp Asn
    210                 215                 220

Asp Gln Cys Tyr Ser His Phe Gln Asn Ile Phe Trp Ser Ser Leu Met
225                 230                 235                 240

Tyr Leu Ser Tyr Leu Leu Phe Cys His Phe Phe Glu Ala Tyr
                245                 250                 255

Ile Gly Lys Val Lys Lys Ala Thr Lys Ala Glu
            260                 265
```

<210> SEQ ID NO 64
<211> LENGTH: 8165
<212> TYPE: DNA

<213> ORGANISM: Artificial Sequence
<220> FEATURE:
<223> OTHER INFORMATION: Plasmid pZUF17

<400> SEQUENCE: 64

```
gtacgagccg aagcataaa gtgtaaagcc tggggtgcct aatgagtgag ctaactcaca      60
ttaattgcgt tgcgctcact gcccgctttc cagtcgggaa acctgtcgtg ccagctgcat     120
taatgaatcg gccaacgcgc ggggagaggc ggtttgcgta ttgggcgctc ttccgcttcc     180
tcgctcactg actcgctgcg ctcggtcgtt cggctgcggc gagcggtatc agctcactca     240
aaggcggtaa tacggttatc cacagaatca ggggataacg caggaaagaa catgtgagca     300
aaaggccagc aaaaggccag gaaccgtaaa aaggccgcgt tgctggcgtt tttccatagg     360
ctccgccccc ctgacgagca tcacaaaaat cgacgctcaa gtcagaggtg gcgaaacccg     420
acaggactat aaagatacca ggcgtttccc cctggaagct ccctcgtgcg ctctcctgtt     480
ccgaccctgc cgcttaccgg atacctgtcc gcctttctcc cttcgggaag cgtggcgctt     540
tctcatagct cacgctgtag gtatctcagt tcggtgtagg tcgttcgctc caagctgggc     600
tgtgtgcacg aaccccccgt tcagcccgac cgctgcgcct tatccggtaa ctatcgtctt     660
gagtccaacc cggtaagaca cgacttatcg ccactggcag cagccactgg taacaggatt     720
agcagagcga ggtatgtagg cggtgctaca gagttcttga agtggtggcc taactacggc     780
tacactagaa ggacagtatt tggtatctgc gctctgctga agccagttac cttcggaaaa     840
agagttggta gctcttgatc cggcaaacaa accaccgctg gtagcggtgg tttttttgtt     900
tgcaagcagc agattacgcg cagaaaaaaa ggatctcaag aagatccttt gatcttttct     960
acggggtctg acgctcagtg gaacgaaaac tcacgttaag ggattttggt catgagatta    1020
tcaaaaagga tcttcaccta gatccttttaa aattaaaaat gaagttttaa atcaatctaa    1080
agtatatatg agtaaacttg gtctgacagt taccaatgct taatcagtga ggcacctatc    1140
tcagcgatct gtctatttcg ttcatccata gttgcctgac tccccgtcgt gtagataact    1200
acgatacggg agggcttacc atctggcccc agtgctgcaa tgataccgcg agacccacgc    1260
tcaccggctc cagatttatc agcaataaac cagccagccg aagggccga gcgcagaagt    1320
ggtcctgcaa ctttatccgc ctccatccag tctattaatt gttgccggga agctagagta    1380
agtagttcgc cagttaatag tttgcgcaac gttgttgcca ttgctacagg catcgtggtg    1440
tcacgctcgt cgtttggtat ggcttcattc agctccggtt cccaacgatc aaggcgagtt    1500
acatgatccc ccatgttgtg caaaaaagcg gttagctcct tcggtcctcc gatcgttgtc    1560
agaagtaagt tggccgcagt gttatcactc atggttatgg cagcactgca taattctctt    1620
actgtcatgc catccgtaag atgcttttct gtgactggtg agtactcaac caagtcattc    1680
tgagaatagt gtatgcggcg accgagttgc tcttgcccgg cgtcaatacg ggataatacc    1740
gcgccacata gcagaacttt aaaagtgctc atcattggaa aacgttcttc ggggcgaaaa    1800
ctctcaagga tcttaccgct gttgagatcc agttcgatgt aacccactcg tgcacccaac    1860
tgatcttcag catcttttac tttcaccagc gtttctgggt gagcaaaaac aggaaggcaa    1920
aatgccgcaa aaagggaat aagggcgaca cggaaatgtt gaatactcat actcttcctt    1980
tttcaatatt attgaagcat ttatcagggt tattgtctca tgagcggata catatttgaa    2040
tgtatttaga aaaataaaca aataggggtt ccgcgcacat ttccccgaaa agtgccacct    2100
gacgcgccct gtagcggcgc attaagcgcg gcgggtgtgg tggttacgcg cagcgtgacc    2160
gctacacttg ccagcgccct agcgcccgct cctttcgctt tcttcccttc ctttctcgcc    2220
```

-continued

```
acgttcgccg gctttccccg tcaagctcta atcggggc tccctttagg gttccgattt    2280
agtgctttac ggcacctcga ccccaaaaaa cttgattagg gtgatggttc acgtagtggg    2340
ccatcgccct gatagacggt ttttcgccct ttgacgttgg agtccacgtt ctttaatagt    2400
ggactcttgt tccaaactgg aacaacactc aaccctatct cggtctattc ttttgattta    2460
taagggattt tgccgatttc ggcctattgg ttaaaaaatg agctgattta acaaaaattt    2520
aacgcgaatt ttaacaaaat attaacgctt acaatttcca ttcgccattc aggctgcgca    2580
actgttggga agggcgatcg gtgcgggcct cttcgctatt acgccagctg gcgaaagggg    2640
gatgtgctgc aaggcgatta agttgggtaa cgccagggtt ttcccagtca cgacgttgta    2700
aaacgacggc cagtgaattg taatacgact cactataggg cgaattgggt accgggcccc    2760
ccctcgaggt cgatggtgtc gataagcttg atatcgaatt catgtcacac aaaccgatct    2820
tcgcctcaag gaaacctaat tctacatccg agagactgcc gagatccagt ctacactgat    2880
taattttcgg gccaataatt taaaaaaatc gtgttatata atattatatg tattatatat    2940
atacatcatg atgatactga cagtcatgtc ccattgctaa atagacagac tccatctgcc    3000
gcctccaact gatgttctca atatttaagg ggtcatctcg cattgtttaa taataaacag    3060
actccatcta ccgcctccaa atgatgttct caaaatatat tgtatgaact tatttttatt    3120
acttagtatt attagacaac ttacttgctt tatgaaaaac acttcctatt taggaaacaa    3180
tttataatgg cagttcgttc atttaacaat ttatgtagaa taaatgttat aaatgcgtat    3240
gggaaatctt aaatatggat agcataaatg atatctgcat tgcctaattc gaaatcaaca    3300
gcaacgaaaa aaatcccttg tacaacataa atagtcatcg agaaatatca actatcaaag    3360
aacagctatt cacacgttac tattgagatt attattggac gagaatcaca cactcaactg    3420
tctttctctc ttctagaaat acaggtacaa gtatgtacta ttctcattgt tcatacttct    3480
agtcatttca tcccacatat tccttggatt tctctccaat gaatgacatt ctatcttgca    3540
aattcaacaa ttataataag ataccaaa gtagcggtat agtggcaatc aaaaagcttc    3600
tctggtgtgc ttctcgtatt tattttatt ctaatgatcc attaaggta tatatttatt    3660
tcttgttata taatcctttt gtttattaca tgggctggat acataaaggt attttgattt    3720
aattttttgc ttaaattcaa tccccctcg ttcagtgtca actgtaatgg taggaaatta    3780
ccatactttt gaagaagcaa aaaaaatgaa agaaaaaaa aatcgtattt ccaggttaga    3840
cgttccgcag aatctagaat gcggtatgcg gtacattgtt cttcgaacgt aaaagttgcg    3900
ctccctgaga tattgtacat ttttgctttt acaagtacaa gtacatcgta caactatgta    3960
ctactgttga tgcatccaca acagtttgtt ttgttttttt ttgttttttt tttttctaat    4020
gattcattac cgctatgtat acctacttgt acttgtagta agccgggtta ttggcgttca    4080
attaatcata gacttatgaa tctgcacggt gtgcgctgcg agttactttt agcttatgca    4140
tgctacttgg gtgtaatatt gggatctgtt cggaaatcaa cggatgctca atcgatttcg    4200
acagtaatta attaagtcat acacaagtca gctttcttcg agcctcatat aagtataagt    4260
agttcaacgt attagcactg tacccagcat ctccgtatcg agaaacacaa caacatgccc    4320
cattggacag atcatgcgga tacacaggtt gtgcagtatc atacatactc gatcagacag    4380
gtcgtctgac catcatacaa gctgaacaag cgctccatac ttgcacgctc tctatataca    4440
cagttaaatt acatatccat agtctaacct ctaacagtta atcttctggt aagcctccca    4500
gccagccttc tggtatcgct tggcctcctc aataggatct cggttctggc cgtacagacc    4560
```

-continued

```
tcggccgaca attatgatat ccgttccggt agacatgaca tcctcaacag ttcggtactg    4620
ctgtccgaga gcgtctccct tgtcgtcaag acccaccccg ggggtcagaa taagccagtc    4680
ctcagagtcg cccttaggtc ggttctgggc aatgaagcca accacaaact cggggtcgga    4740
tcgggcaagc tcaatggtct gcttggagta ctcgccagtg ccagagagc ccttgcaaga     4800
cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag aagaaaccg tgcttaagag caagttcctt    5100
gagggggagc acagtgccgg cgtaggtgaa gtcgtcaatg atgtcgatat gggttttgat    5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg ggcagtgaa    5400
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
gggttggcgg cgtatttgtg tcccaaaaaa cagccccaat tgccccggag aagacggcca    5820
ggccgcctag atgacaaatt caacaactca cagctgactt tctgccattg ccactagggg    5880
ggggccttt tatatggcca agccaagctc tccacgtcgg ttgggctgca cccaacaata    5940
aatgggtagg gttgcaccaa caaagggatg ggatgggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata    6360
tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc gggggcttg tctagggtat atataaacag tggctctccc aatcggttgc     6540
cagtctcttt tttccttct ttccccacag attcgaaatc taaactacac atcacacaat     6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggctgagga    6780
taagaccaag gtcgagttcc ctaccctgac tgagctgaag cactctatcc ctaacgcttg    6840
ctttgagtcc aacctcggac tctcgctcta ctacactgcc cgagcgatct tcaacgcatc    6900
tgcctctgct gctctgctct acgctgcccg atctactccc ttcattgccg ataacgttct    6960
```

-continued

```
gctccacgct ctggtttgcg ccacctacat ctacgtgcag ggtgtcatct tctggggttt     7020
ctttaccgtc ggtcacgact gtggtcactc tgccttctcc cgataccact ccgtcaactt     7080
catcattggc tgcatcatgc actctgccat tctgactccc ttcgagtcct ggcgagtgac     7140
ccaccgacac catcacaaga acactggcaa cattgataag gacgagatct tctaccctca     7200
tcggtccgtc aaggacctcc aggacgtgcg acaatgggtc tacaccctcg gaggtgcttg     7260
gtttgtctac ctgaaggtcg gatatgctcc tcgaaccatg tcccactttg acccctggga     7320
ccctctcctg cttcgacgag cctccgctgt catcgtgtcc ctcggagtct gggctgcctt     7380
cttcgctgcc tacgcctacc tcacatactc gctcggcttt gccgtcatgg gcctctacta     7440
ctatgctcct ctctttgtct ttgcttcgtt cctcgtcatt actaccttct tgcatcacaa     7500
cgacgaagct actccctggt acggtgactc ggagtggacc tacgtcaagg caacctgag     7560 ctccgtcgac cgatcgtacg gagctttcgt ggacaacctg tctcaccaca ttggcaccca     7620
ccaggtccat cacttgttcc ctatcattcc ccactacaag ctcaacgaag ccaccaagca     7680
ctttgctgcc gcttaccctc acctcgtgag acgtaacgac gagcccatca ttactgcctt     7740
cttcaagacc gctcacctct ttgtcaacta cggagctgtg cccgagactg ctcagatttt     7800 cacccctcaaa gagtctgccg ctgcagccaa ggccaagagc gactaagcgg ccgcaagtgt     7860 ggatgggaa gtgagtgccc ggttctgtgt gcacaattgg caatccaaga tggatggatt     7920
caacacaggg atatagcgag ctacgtggtg gtgcgaggat atagcaacgg atatttatgt     7980
ttgacacttg agaatgtacg atacaagcac tgtccaagta caatactaaa catactgtac     8040
atactcatac tcgtacccgg gcaacggttt cacttgagtg cagtggctag tgctcttact     8100
cgtacagtgt gcaatactgc gtatcatagt ctttgatgta tatcgtattc attcatgtta     8160
gttgc                                                                8165
```

<210> SEQ ID NO 65
<211> LENGTH: 28
<212> TYPE: DNA
<213> ORGANISM: Artificial Sequence
<220> FEATURE:
<223> OTHER INFORMATION: Primer MDGAT-F
<400> SEQUENCE: 65

```
gatcccatgg cgctctttgc gcctttac                                         28
```

<210> SEQ ID NO 66
<211> LENGTH: 35
<212> TYPE: DNA
<213> ORGANISM: Artificial Sequence
<220> FEATURE:
<223> OTHER INFORMATION: Primer MDGAT-R1

<400> SEQUENCE: 66

```
gatcgcggcc gcctattcga tgatgcacag ttcct                                 35
```

<210> SEQ ID NO 67
<211> LENGTH: 8084
<212> TYPE: DNA
<213> ORGANISM: Artificial Sequence
<220> FEATURE:
<223> OTHER INFORMATION: Plasmid pMDGAT2-17

<400> SEQUENCE: 67

```
catggcgctc tttgcgcctt tacggatgcc cgtcaagcgt cgtatgcaga caggagctgt     60
```

```
cctatactgg attgcgggga tgatttactg cattggcatc tttgccttcc tctgcacgtt    120
caagatcctt cgacccttga tcatcatcta tgtcctgtgg gcctacatgc tcgaccgagc    180
accagagcgg ggtgcacgca cagtccaatg gtattgtaac tggatcggat ggaaacactt    240
tgcacagtac tttcctatga cccttgtcaa ggagggagag ctggacccat ccaagaacta    300
catctttggg tatcacccac acggaatcat ttccttgggt gccctctgcg cctttgggac    360
cgagggcctt catttctcca aacgcttccc gggtatcaag cctcatctgc tcaccattca    420
cgccaacttt cagatcccac tctatcgcga tatgatcatg gcccacggct gtgcttccgt    480
gtcgagggcc tcttgtgaac acatcctgcg gtctggcgaa ggatcctcgg tcgtgatcgt    540
tgtcgggggt gcacaagaaa gtttgtcgac tcaacctggc acgttaaatc tgacactcaa    600
gaaaagactg ggattttgca agctggcctt tgtcaatggc gcaagtctgg tacctacgtt    660
ggcctttggt gagaacgagc tctatgaggt gtaccacacc aagcccacaa gcctgatata    720
caagctccag cagttgacta aacgcacgat cggcttcaca atgcccgtgt tcaacggacg    780
aggaatcttc aattatgagt ttggactgct gccaaggagg aagcctgtct atatcgttat    840
aggaaacccc attcatgtag acaaggtcga aacccaacg attgaacaga tgcagaaact    900
gcagtcaatt tacattgatg aggtgctaaa catttgggaa agatacaagg acaagtatgc    960
cgcaggacga actcaggaac tgtgcatcat cgaataggcg gccgcaagtg tggatgggga    1020
agtgagtgcc cggttctgtg tgcacaattg gcaatccaag atggatggat tcaacacagg    1080
gatatagcga gctacgtggt ggtgcgagga tatagcaacg gatatttatg tttgacactt    1140
gagaatgtac gatacaagca ctgtccaagt acaatactaa acatactgta catactcata    1200
ctcgtacccg ggcaacggtt tcacttgagt gcagtggcta gtgctcttac tcgtacagtg    1260
tgcaatactg cgtatcatag tctttgatgt atatcgtatt cattcatgtt agttgcgtac    1320
gagccggaag cataaagtgt aaagcctggg gtgcctaatg agtgagctaa ctcacattaa    1380
ttgcgttgcg ctcactgccc gctttccagt cgggaaacct gtcgtgccag ctgcattaat    1440
gaatcggcca acgcgcgggg agaggcggtt tgcgtattgg gcgctcttcc gcttcctcgc    1500
tcactgactc gctgcgctcg gtcgttcggc tgcggcgagc ggtatcagct cactcaaagg    1560
cggtaatacg gttatccaca gaatcagggg ataacgcagg aaagaacatg tgagcaaaag    1620
gccagcaaaa ggccaggaac cgtaaaaagg ccgcgttgct ggcgtttttc cataggctcc    1680
gcccccctga cgagcatcac aaaaatcgac gctcaagtca gaggtggcga acccgacag    1740 gactataaag ataccaggcg tttccccctg gaagctccct cgtgcgctct cctgttccga    1800
ccctgccgct taccggatac ctgtccgcct ttctcccttc gggaagcgtg gcgctttctc    1860
atagctcacg ctgtaggtat ctcagttcgg tgtaggtcgt tcgctccaag ctgggctgtg    1920
tgcacgaacc cccgttcag cccgaccgct gcgccttatc cggtaactat cgtcttgagt    1980
ccaacccggt aagacacgac ttatcgccac tggcagcagc cactggtaac aggattagca    2040
gagcgaggta tgtaggcggt gctacagagt tcttgaagtg gtggcctaac tacggctaca    2100
ctagaaggac agtatttggt atctgcgctc tgctgaagcc agttaccttc ggaaaaagag    2160
ttggtagctc ttgatccggc aaacaaacca ccgctggtag cggtggtttt tttgtttgca    2220
agcagcagat tacgcgcaga aaaaaggat ctcaagaaga tcctttgatc ttttctacgg    2280
ggtctgacgc tcagtggaac gaaaactcac gttaagggat tttggtcatg agattatcaa    2340
aaaggatctt cacctagatc cttttaaatt aaaaatgaag ttttaaatca atctaaagta    2400
tatatgagta aacttggtct gacagttacc aatgcttaat cagtgaggca cctatctcag    2460
```

```
cgatctgtct atttcgttca tccatagttg cctgactccc cgtcgtgtag ataactacga   2520
tacgggaggg cttaccatct ggccccagtg ctgcaatgat accgcgagac ccacgctcac   2580
cggctccaga tttatcagca ataaaccagc cagccggaag ggccgagcgc agaagtggtc   2640
ctgcaacttt atccgcctcc atccagtcta ttaattgttg ccgggaagct agagtaagta   2700
gttcgccagt taatagtttg cgcaacgttg ttgccattgc tacaggcatc gtggtgtcac   2760
gctcgtcgtt tggtatggct tcattcagct ccggttccca acgatcaagg cgagttacat   2820
gatcccccat gttgtgcaaa aaagcggtta gctccttcgg tcctccgatc gttgtcagaa   2880
gtaagttggc cgcagtgtta tcactcatgg ttatggcagc actgcataat tctcttactg   2940
tcatgccatc cgtaagatgc ttttctgtga ctggtgagta ctcaaccaag tcattctgag   3000
aatagtgtat gcggcgaccg agttgctctt gcccggcgtc aatacgggat aataccgcgc   3060
cacatagcag aactttaaaa gtgctcatca ttggaaaacg ttcttcgggg cgaaaactct   3120
caaggatctt accgctgttg agatccagtt cgatgtaacc cactcgtgca cccaactgat   3180
cttcagcatc ttttactttc accagcgttt ctgggtgagc aaaaacagga aggcaaaatg   3240
ccgcaaaaaa gggaataagg gcgacacgga aatgttgaat actcatactc ttcctttttc   3300
aatattattg aagcatttat cagggttatt gtctcatgag cggatacata tttgaatgta   3360
tttagaaaaa taaacaaata ggggttccgc gcacatttcc ccgaaaagtg ccacctgacg   3420
cgccctgtag cggcgcatta agcgcggcgg gtgtggtggt tacgcgcagc gtgaccgcta   3480
cacttgccag cgccctagcg cccgctcctt tcgctttctt cccttccttt ctcgccacgt   3540
tcgccggctt tccccgtcaa gctctaaatc ggggggctccc tttagggttc cgatttagtg   3600
ctttacggca cctcgacccc aaaaaacttg attagggtga tggttcacgt agtgggccat   3660
cgccctgata gacggttttt cgccctttga cgttggagtc cacgttcttt aatagtggac   3720
tcttgttcca aactggaaca acactcaacc ctatctcggt ctattctttt gatttataag   3780
ggattttgcc gatttcggcc tattggttaa aaaatgagct gatttaacaa aaatttaacg   3840
cgaattttaa caaaatatta acgcttacaa tttccattcg ccattcaggc tgcgcaactg   3900
ttgggaaggg cgatcggtgc gggcctcttc gctattacgc cagctggcga aggggggatg   3960
tgctgcaagg cgattaagtt gggtaacgcc agggttttcc cagtcacgac gttgtaaaac   4020
gacggccagt gaattgtaat acgactcact atagggcgaa ttgggtaccg gccccccct   4080 cgaggtcgat ggtgtcgata agcttgatat cgaattcatg tcacacaaac cgatcttcgc   4140
ctcaaggaaa cctaattcta catccgagag actgccgaga tccagtctac actgattaat   4200
tttcgggcca ataatttaaa aaaatcgtgt tatataatat tatatgtatt atatatatac   4260
atcatgatga tactgacagt catgtcccat tgctaaatag acagactcca tctgccgcct   4320
ccaactgatg ttctcaatat ttaaggggtc atctcgcatt gtttaataat aaacagactc   4380
catctaccgc ctccaaatga tgttctcaaa atatattgta tgaacttatt tttattactt   4440
agtattatta gacaacttac ttgctttatg aaaaacactt cctatttagg aaacaattta   4500
taatggcagt tcgttcattt aacaatttat gtagaataaa tgttataaat gcgtatggga   4560
aatcttaaat atggatagca taatgatat ctgcattgcc taattcgaaa tcaacagcaa   4620 cgaaaaaat cccttgtaca acataaatag tcatcgagaa atatcaacta tcaaagaaca   4680
gctattcaca cgttactatt gagattatta ttggacgaga atcacacact caactgtctt   4740
tctctcttct agaaatacag gtacaagtat gtactattct cattgttcat acttctagtc   4800
```

```
atttcatccc acatattcct tggatttctc tccaatgaat gacattctat cttgcaaatt    4860
caacaattat aataagatat accaaagtag cggtatagtg gcaatcaaaa agcttctctg    4920
gtgtgcttct cgtatttatt tttattctaa tgatccatta aaggtatata tttatttctt    4980
gttatataat cctttgttt attacatggg ctggatacat aaaggtattt tgatttaatt    5040
ttttgcttaa attcaatccc ccctcgttca gtgtcaactg taatggtagg aaattaccat    5100
acttttgaag aagcaaaaaa aatgaaagaa aaaaaaatc gtatttccag gttagacgtt    5160
ccgcagaatc tagaatgcgg tatgcggtac attgttcttc gaacgtaaaa gttgcgctcc    5220
ctgagatatt gtacattttt gcttttacaa gtacaagtac atcgtacaac tatgtactac    5280
tgttgatgca tccacaacag tttgttttgt ttttttttgt ttttttttt tctaatgatt    5340
cattaccgct atgtatacct acttgtactt gtagtaagcc gggttattgg cgttcaatta    5400
atcatagact tatgaatctg cacggtgtgc gctgcgagtt acttttagct tatgcatgct    5460
acttgggtgt aatattggga tctgttcgga aatcaacgga tgctcaatcg atttcgacag    5520
taattaatta agtcatacac aagtcagctt tcttcgagcc tcatataagt ataagtagtt    5580
caacgtatta gcactgtacc cagcatctcc gtatcgagaa acacaacaac atgccccatt    5640
ggacagatca tgcggataca caggttgtgc agtatcatac atactcgatc agacaggtcg    5700
tctgaccatc atacaagctg aacaagcgct ccatacttgc acgctctcta tatacacagt    5760
taaattacat atccatagtc taacctctaa cagttaatct tctggtaagc ctcccagcca    5820
gccttctggt atcgcttggc ctcctcaata ggatctcggt tctggccgta cagacctcgg    5880
ccgacaatta tgatatccgt tccggtagac atgacatcct caacagttcg gtactgctgt    5940
ccgagagcgt ctcccttgtc gtcaagaccc accccggggg tcagaataag ccagtcctca    6000
gagtcgccct taggtcggtt ctgggcaatg aagccaacca caaactcggg gtcggatcgg    6060
gcaagctcaa tggtctgctt ggagtactcg ccagtggcca gagagccctt gcaagacagc    6120
tcggccagca tgagcagacc tctggccagc ttctcgttgg gagaggggac taggaactcc    6180
ttgtactggg agttctcgta gtcagagacg tcctccttct tctgttcaga gacagtttcc    6240
tcggcaccag ctcgcaggcc agcaatgatt ccggttccgg gtacaccgtg ggcgttggtg    6300
atatcggacc actcggcgat tcggtgcaca cggtactggt gcttgacagt gttgccaata    6360
tctgcgaact ttctgtcctc gaacaggaag aaaccgtgct taagagcaag ttccttgagg    6420
gggagcacag tgccggcgta ggtgaagtcg tcaatgatgt cgatatgggg tttgatcatg    6480
cacacataag gtccgacctt atcggcaagc tcaatgagct ccttggtggt ggtaacatcc    6540
agagaagcac acaggttggt tttcttggct gccacgagct tgagcactcg agcggcaaag    6600
gcggacttgt ggacgttagc tcgagcttcg taggagggca ttttggtggt gaagaggaga    6660
ctgaaataaa tttagtctgc agaactttt atcggaacct tatctggggc agtgaagtat    6720
atgttatggt aatagttacg agttagttga acttatagat agactggact atacggctat    6780
cggtccaaat tagaaagaac gtcaatggct ctctgggcgt cgcctttgcc gacaaaaatg    6840
tgatcatgat gaaagccagc aatgacgttg cagctgtatt tgttgtcggc caaccgcgcc    6900
gaaaacgcag ctgtcagacc cacagcctcc aacgaagaat gtatcgtcaa agtgatccaa    6960
gcacactcat agttggagtc gtactccaaa ggcggcaatg acgagtcaga cagatactcg    7020
tcgactcagg cgacgacgga attcctgcag cccatctgca gaattcagga gagaccgggt    7080
tggcggcgta tttgtgtccc aaaaaacagc cccaattgcc ccgagaagaa cggccaggcc    7140
gcctagatga caaattcaac aactcacagc tgactttctg ccattgccac tagggggggg    7200
```

-continued

| | |
|---|---|
| ccttttttata tggccaagcc aagctctcca cgtcggttgg gctgcaccca acaataaatg | 7260 |
| ggtagggttg caccaacaaa gggatgggat gggggtaga agatacgagg ataacggggc | 7320 |
| tcaatggcac aaataagaac gaatactgcc attaagactc gtgatccagc gactgacacc | 7380 |
| attgcatcat ctaagggcct caaaactacc tcggaactgc tgcgctgatc tggacaccac | 7440 |
| agaggttccg agcactttag gttgcaccaa atgtcccacc aggtgcaggc agaaaacgct | 7500 |
| ggaacagcgt gtacagtttg tcttaacaaa aagtgagggc gctgaggtcg agcagggtgg | 7560 |
| tgtgacttgt tatagccttt agagctgcga aagcgcgtat ggatttggct catcaggcca | 7620 |
| gattgagggt ctgtggacac atgtcatgtt agtgtacttc aatcgccccc tggatatagc | 7680 |
| cccgacaata ggccgtggcc tcatttttt gccttccgca catttccatt gctcggtacc | 7740 |
| cacaccttgc ttctcctgca cttgccaacc ttaatactgg tttacattga ccaacatctt | 7800 |
| acaagcgggg ggcttgtcta gggtatatat aaacagtggc tctcccaatc ggttgccagt | 7860 |
| ctcttttttc ctttctttcc ccacagattc gaaatctaaa ctacacatca cacaatgcct | 7920 |
| gttactgacg tccttaagcg aaagtccggt gtcatcgtcg gcgacgatgt ccgagccgtg | 7980 |
| agtatccacg acaagatcag tgtcgagacg acgcgttttg tgtaatgaca caatccgaaa | 8040 |
| gtcgctagca acacacactc tctacacaaa ctaacccagc tctc | 8084 |

<210> SEQ ID NO 68
<211> LENGTH: 7323
<212> TYPE: DNA
<213> ORGANISM: Artificial Sequence
<220> FEATURE:
<223> OTHER INFORMATION: Plasmid pZUF-MOD-1

<400> SEQUENCE: 68

| | |
|---|---|
| gtacgagccg gaagcataaa gtgtaaagcc tggggtgcct aatgagtgag ctaactcaca | 60 |
| ttaattgcgt tgcgctcact gcccgctttc cagtcgggaa acctgtcgtg ccagctgcat | 120 |
| taatgaatcg gccaacgcgc ggggagaggc ggtttgcgta ttgggcgctc ttccgcttcc | 180 |
| tcgctcactg actcgctgcg ctcggtcgtt cggctgcggc gagcggtatc agctcactca | 240 |
| aaggcggtaa tacggttatc cacagaatca ggggataacg caggaaagaa catgtgagca | 300 |
| aaaggccagc aaaaggccag gaaccgtaaa aaggccgcgt tgctggcgtt tttccatagg | 360 |
| ctccgccccc ctgacgagca tcacaaaaat cgacgctcaa gtcagaggtg gcgaaacccg | 420 |
| acaggactat aaagatacca ggcgtttccc cctggaagct ccctcgtgcg ctctcctgtt | 480 |
| ccgaccctgc cgcttaccgg atacctgtcc gcctttctcc cttcgggaag cgtggcgctt | 540 |
| tctcatagct cacgctgtag gtatctcagt tcggtgtagg tcgttcgctc caagctgggc | 600 |
| tgtgtgcacg aaccccccgt tcagcccgac cgctgcgcct tatccggtaa ctatcgtctt | 660 |
| gagtccaacc cggtaagaca cgacttatcg ccactggcag cagccactgg taacaggatt | 720 |
| agcagagcga ggtatgtagg cggtgctaca gagttcttga agtggtggcc taactacggc | 780 |
| tacactagaa ggacagtatt tggtatctgc gctctgctga agccagttac cttcggaaaa | 840 |
| agagttggta gctcttgatc cggcaaacaa accaccgctg gtagcggtgg tttttttgtt | 900 |
| tgcaagcagc agattacgcg cagaaaaaaa ggatctcaag aagatccttt gatcttttct | 960 |
| acgggtctg acgctcagtg gaacgaaaac tcacgttaag ggattttggt catgagatta | 1020 |
| tcaaaaagga tcttcaccta gatccttta aattaaaaat gaagttttaa atcaatctaa | 1080 |
| agtatatatg agtaaacttg gtctgacagt taccaatgct taatcagtga ggcacctatc | 1140 |

```
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca atagggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tattttattt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
```

-continued

| | |
|---|---|
| aattcaacaa ttataataag atataccaaa gtagcggtat agtggcaatc aaaaagcttc | 3600 |
| tctggtgtgc ttctcgtatt tattttatt ctaatgatcc attaaaggta tatatttatt | 3660 |
| tcttgttata taatcctttt gtttattaca tgggctggat acataaaggt attttgattt | 3720 |
| aattttttgc ttaaattcaa tcccccctcg ttcagtgtca actgtaatgg taggaaatta | 3780 |
| ccatactttt gaagaagcaa aaaaatgaa agaaaaaaaa aatcgtattt ccaggttaga | 3840 |
| cgttccgcag aatctagaat gcggtatgcg gtacattgtt cttcgaacgt aaaagttgcg | 3900 |
| ctccctgaga tattgtacat ttttgctttt acaagtacaa gtacatcgta caactatgta | 3960 |
| ctactgttga tgcatccaca acagtttgtt ttgttttttt ttgttttttt tttttctaat | 4020 |
| gattcattac cgctatgtat acctacttgt acttgtagta agccgggtta ttggcgttca | 4080 |
| attaatcata gacttatgaa tctgcacggt gtgcgctgcg agttactttt agcttatgca | 4140 |
| tgctacttgg gtgtaatatt gggatctgtt cggaaatcaa cggatgctca atcgatttcg | 4200 |
| acagtaatta attaagtcat acacaagtca gctttcttcg agcctcatat aagtataagt | 4260 |
| agttcaacgt attagcactg tacccagcat ctccgtatcg agaaacacaa caacatgccc | 4320 |
| cattggacag atcatgcgga tacacaggtt gtgcagtatc atacatactc gatcagacag | 4380 |
| gtcgtctgac catcatacaa gctgaacaag cgctccatac ttgcacgctc tctatataca | 4440 |
| cagttaaatt acatatccat agtctaacct ctaacagtta atcttctggt aagcctccca | 4500 |
| gccagccttc tggtatcgct tggcctcctc aataggatct cggttctggc cgtacagacc | 4560 |
| tcggccgaca attatgatat ccgttccggt agacatgaca tcctcaacag ttcggtactg | 4620 |
| ctgtccgaga gcgtctccct tgtcgtcaag acccacccg ggggtcagaa taagccagtc | 4680 |
| ctcagagtcg cccttaggtc ggttctgggc aatgaagcca accacaaact cggggtcgga | 4740 |
| tcgggcaagc tcaatggtct gcttggagta ctcgccagtg gccagagagc ccttgcaaga | 4800 |
| cagctcggcc agcatgagca gacctctggc cagcttctcg ttgggagagg ggactaggaa | 4860 |
| ctccttgtac tgggagttct cgtagtcaga gacgtcctcc ttcttctgtt cagagacagt | 4920 |
| ttcctcggca ccagctcgca ggccagcaat gattccggtt ccgggtacac cgtgggcgtt | 4980 |
| ggtgatatcg gaccactcgg cgattcggtg acaccggtac tggtgcttga cagtgttgcc | 5040 |
| aatatctgcg aactttctgt cctcgaacag gaagaaaccg tgcttaagag caagttcctt | 5100 |
| gaggggagc acagtgccgg cgtaggtgaa gtcgtcaatg atgtcgatat gggttttgat | 5160 |
| catgcacaca taaggtccga ccttatcggc aagctcaatg agctccttgg tggtggtaac | 5220 |
| atccagagaa gcacacaggt tggttttctt ggctgccacg agcttgagca ctcgagcggc | 5280 |
| aaaggcggac ttgtggacgt tagctcgagc ttcgtaggag ggcattttgg tggtgaagag | 5340 |
| gagactgaaa taaatttagt ctgcagaact ttttatcgga accttatctg gggcagtgaa | 5400 |
| gtatatgtta tggtaatagt tacgagttag ttgaacttat agatagactg gactatacgg | 5460 |
| ctatcggtcc aaattagaaa gaacgtcaat ggctctctgg gcgtcgcctt tgccgacaaa | 5520 |
| aatgtgatca tgatgaaagc cagcaatgac gttgcagctg atattgttgt cggccaaccg | 5580 |
| cgccgaaaac gcagctgtca gacccacagc ctccaacgaa gaatgtatcg tcaaagtgat | 5640 |
| ccaagcacac tcatagttgg agtcgtactc caaaggcggc aatgacgagt cagcagata | 5700 |
| ctcgtcgact caggcgacga cggaattcct gcagcccatc tgcagaattc aggagagacc | 5760 |
| gggttggcgg cgtatttgtg tcccaaaaaa cagcccaat tgccccggag aagacggcca | 5820 |
| ggccgcctag atgacaaatt caacaactca cagctgactt tctgccattg ccactagggg | 5880 |

-continued

```
gggggccttttt tatatggcca agccaagctc tccacgtcgg ttgggctgca cccaacaata    5940
aatgggtagg gttgcaccaa caaagggatg ggatgggggg tagaagatac gaggataacg    6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagagtt tccgagcact ttaggttgca ccaaatgtcc caccaggtgc aggcagaaaa    6180
cgctggaaca gcgtgtacag tttgtcttaa caaaagtga gggcgctgag gtcgagcagg     6240
gtggtgtgac ttgttatagc ctttagagct gcgaaagcgc gtatggattt ggctcatcag    6300
gccagattga gggtctgtgg acacatgtca tgttagtgta cttcaatcgc ccctggata    6360 tagccccgac aataggccgt ggcctcattt ttttgccttc cgcacatttc cattgctcgg    6420
tacccacacc ttgcttctcc tgcacttgcc aaccttaata ctggtttaca ttgaccaaca    6480
tcttacaagc gggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgacaaga tcagtgtcga gacgacgcgt tttgtgtaat gacacaatcc    6720
gaaagtcgct agcaacacac actctctaca caaactaacc cagctctcca tggatccagg    6780
cctgttaacg gccattacgg cctgcaggat ccgaaaaaac ctcccacacc tccccctgaa    6840
cctgaaacat aaaatgaatg caattgttgt tgttaacttg tttattgcag cttataatgg    6900
ttacaaataa agcaatagca tcacaaattt cacaaataaa gcatttttt cactgcattc    6960 tagttgtggt ttgtccaaac tcatcaatgt atcttatcat gtctgcggcc gcaagtgtgg    7020
atggggaagt gagtgcccgg ttctgtgtgc acaattggca atccaagatg gatggattca    7080
acacagggat atagcgagct acgtggtggt gcgaggatat agcaacggat atttatgttt    7140
gacacttgag aatgtacgat acaagcactg tccaagtaca atactaaaca tactgtacat    7200
actcatactc gtacccgggc aacggtttca cttgagtgca gtggctagtg ctcttactcg    7260
tacagtgtgc aatactgcgt atcatagtct ttgatgtata tcgtattcat tcatgttagt    7320
tgc                                                                  7323
```

<210> SEQ ID NO 69
<211> LENGTH: 28
<212> TYPE: DNA
<213> ORGANISM: Artificial Sequence
<220> FEATURE:
<223> OTHER INFORMATION: Primer PZUF-mod1

<400> SEQUENCE: 69

```
gatcccatgg atccaggcct gttaacgg                                       28
```

<210> SEQ ID NO 70
<211> LENGTH: 32
<212> TYPE: DNA
<213> ORGANISM: Artificial Sequence
<220> FEATURE:
<223> OTHER INFORMATION: Primer PZUF-mod2

<400> SEQUENCE: 70

```
gatcgcggcc gcagacatga taagatacat tg                                  32
```

MORTIERELLA ALPINA DIACYLGLYCEROL ACYLTRANSFERASE FOR ALTERATION OF POLYUNSATURATED FATTY ACIDS AND OIL CONTENT IN OLEAGINOUS ORGANISMS

This application claims the benefit of U.S. patent application Ser. No. 60/624,812, filed Nov. 4, 2004.

FIELD OF THE INVENTION

This invention is in the field of biotechnology. More specifically, this invention pertains to the identification of a nucleic acid fragment isolated from *Mortierella alpina* encoding a diacylglycerol acyltransferase (DGAT2). This enzyme is useful for altering the quantity of oil in oleaginous microorganisms, such as oleaginous yeast.

BACKGROUND OF THE INVENTION

The present invention is directed toward the development of an oleaginous yeast that accumulates oils enriched in long-chain ω-3 and/or ω-6 polyunsaturated fatty acids ("PUFAs"; e.g., 18:3, 18:4, 20:3, 20:4, 20:5, 22:6 fatty acids). Toward this end, the natural abilities of oleaginous yeast (mostly limited to 18:2 fatty acid production) have been enhanced by advances in genetic engineering, leading to the production of 20:4 (arachidonic acid or "ARA"), 20:5 (eicosapentaenoic acid or "EPA") and 22:6 (docosahexaenoic acid or "DHA") PUFAs in transformant *Yarrowia lipolytica*. These ω-3 and ω-6 fatty acids were produced by introducing and expressing heterologous genes encoding the ω-3/ω-6 biosynthetic pathway in the oleaginous host (see co-pending U.S. patent applications Ser. No. 10/840,579 and Ser. No. 60/624,812, each entirely incorporated herein by reference). However, in addition to developing techniques to introduce the appropriate fatty acid desaturases and elongases into these particular host organisms, it is also necessary to increase the transfer of PUFAs into storage lipid pools following their synthesis.

Most free fatty acids become esterified to coenzyme A (CoA) to yield acyl-CoAs. These molecules are then substrates for glycerolipid synthesis in the endoplasmic reticulum of the cell, where phosphatidic acid and diacylglycerol (DAG) are produced. Either of these metabolic intermediates may be directed to membrane phospholipids (e.g., phosphatidylglycerol, phosphatidylethanolamine, phosphatidylcholine) or DAG may be directed to form triacylglycerols (TAGs), the primary storage reserve of lipids in eukaryotic cells.

In the yeast *Saccharomyces cerevisiae*, three pathways have been described for the synthesis of TAGs. First, TAGs are mainly synthesized from DAG and acyl-CoAs by the activity of diacylglycerol acyltransferases. More recently, however, a phospholipid:diacylglycerol acyltransferase has also been identified that is responsible for conversion of phospholipid and DAG to lysophospholipid and TAG, respectively, thus producing TAG via an acyl-CoA-independent mechanism (Dahlqvist et al., *PNAS*. 97(12): 6487–6492 (2000)). Finally, two acyl-CoA:sterol-acyltransferases are known that utilize acyl-CoAs and sterols to produce sterol esters (and TAGs in low quantities; see Sandager et al., *Biochem. Soc. Trans.* 28(6):700–702 (2000)).

A comprehensive mini-review on TAG biosynthesis in yeast, including details concerning the genes involved and the metabolic intermediates that lead to TAG synthesis, is that of D. Sorger and G. Daum (*Appl. Microbiol. Biotechnol.* 61:289–299 (2003)). However, the authors acknowledge that most work performed thus far has focused on *Saccharomyces cerevisiae* and numerous questions regarding TAG formation and regulation remain. In this organism it has been conclusively demonstrated that only four genes are involved in storage lipid synthesis: ARE1 and ARE2 (encoding acyl-CoA:sterol-acyltransferases), LRO1 (encoding a phospholipid:diacylglycerol acyltransferase, or PDAT enzyme) and DGA1 (encoding a diacylglycerol acyltransferase, or DGAT2 enzyme) (Sandager, L. et al., *J. Biol. Chem.* 277(8):6478–6482 (2002)).

Although homologs of the acyltransferase genes described above have been identified in various other organisms and disclosed in the public literature, few genes are available from oleaginous organisms. Concerning diacylglycerol acyltransferases, a single DGAT2 enzyme from oleaginous yeast (i.e., *Yarrowia lipolytica*) has been isolated and characterized in co-pending U.S. patent application Ser. No. 10/882,760. Since the natural capabilities of this organism are limited to 18:2 fatty acid production, however, its native diacylglycerol acyltransferases (including DGAT2) are not likely to utilize longer chain PUFAs (i.e., $C_{20}$ or greater) as efficiently as those from organisms that are naturally capable of producing longer chain PUFAs. The production of ARA, EPA and DHA PUFAs in transformant *Yarrowia lipolytica* therefore is likely to be improved by the use of heterologous acyltransferases (e.g., DGAT2) having altered substrate specificies, as compared to the native enzymes. Furthermore, techniques for modifying the transfer of fatty acids to the TAG pool in oleaginous yeast have not been developed.

Only three DGAT2 enzymes have been isolated from oleaginous fungi. Specifically, Lardizabal et al. isolated and characterized two DGAT2s (i.e., MrDGAT2A and MrDGAT2B) from *Mortierella ramanniana* (*J. Biol. Chem.* 276(42):38862–28869 (2001)); US 2003/0028923 A1, US 2003/0115632 A1) and one DGAT2 from *Neurospora crassa* (Nc DGAT2; see US 2004/0107459 A1). Upon expression of MrDGAT2A, MrDGAT2B, and NcDGAT2 in insect cells, high levels of DGAT activity were obtained on membranes isolated from those cells. Like *Y. lipolytica*, however, *M. ramanniana* and *N. crassa* are generally limited to production of 16:0, 18:0, 18:1, 18:2 and 18:3 fatty acids (although synthesis of 20:0 fatty acids is observed in *M. ramanniana* during lower temperature growth; see da Silva M., et al. *Rev. Microbiol.* 29:4 São Paulo (October/December 1998)). Thus, the DGAT2s from *M. ramanniana* and *N. crassa* are likely not preferred for the transfer of 20:4, 20:5 and 22:6 PUFAs to the TAG pool in a transformant oleaginous yeast.

A variety of microorganisms are known that naturally produce long-chain PUFAs (e.g., ARA and EPA, DHA). For example, microorganisms in the genera *Mortierella* (filamentous fungus), *Entomophthora*, *Pythium* and *Porphyridium* (red alga) can be used for commercial production of the ω-6 fatty acid, ARA. The fungus *Mortierella alpina*, for example, is used to produce an oil containing ARA, while U.S. Pat. No. 5,658,767 (Martek Corporation) teaches a method for the production of an oil containing ARA comprising cultivating *Pythium insidiuosum* in a culture medium containing a carbon and nitrogen source. Likewise, U.S. Pat. No. 5,244,921 (Martek Corporation) describes a process for producing an edible oil containing EPA, by cultivating the heterotrophic diatoms *Cyclotella* sp. and *Nitzschia* sp. in a fermentor. DHA can be obtained by cultivation of the heterotrophic microalgae *Crypthecodinium cohnii* (U.S. Pat. No. 5,492,938 and U.S. Pat. No. 5,407,957). Other long-chain PUFA-producing organisms include *Thraus-* tochytrium sp. and the green alga *Parietochloris incisa*. It is likely that many of these organisms possess genes encoding acyltransferases that would be preferred for the incorporation of long-chain PUFAs in a transformant oleaginous yeast, relative to the native acyltransferases that do not naturally produce long-chain PUFAs.

Thus, there is a need for the identification and isolation of a gene encoding an acyltransferase from an organism such as those above, to permit its use in the production and accumulation of long-chain PUFAs in the storage lipid pools (i.e., TAG fraction) of transformant oleaginous yeast.

Applicants have solved the stated problem by isolating the gene encoding DGAT2 from the oleaginous fungus, *Mortierella alpina*. This gene will be useful to enable one to modify the transfer of long-chain free fatty acids (e.g., $\omega$-3 and/or $\omega$-6 fatty acids) to the TAG pool in oleaginous yeast.

SUMMARY OF THE INVENTION

The invention relates to the discovery of a gene encoding a diacylglycerol acyltransferase enzyme from *Mortierella*. This gene and encoded enzyme are useful in manipulating the production of commercially useful oils in microorganisms, and particularly in oleaginous yeast. Accordingly the invention provides an isolated nucleic acid molecule encoding an diacylglycerol acyltransferase 2 enzyme, selected from the group consisting of:

(a) an isolated nucleic acid molecule encoding the amino acid sequence as set forth in SEQ ID NO:2;
(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or
(c) an isolated nucleic acid molecule that is completely complementary to (a) or (b).

Similarly the invention provides a polypeptide having diacylglycerol acyltransferase 2 activity encoded by the isolated nucleic acid molecule of the invention as well as genetic chimera of these molecules and host cells comprising the same.

In one preferred embodiment the invention provides a method of increasing triacylglycerol content in a transformed host cell comprising:

(a) providing a transformed host cell comprising:
  (i) at least one gene encoding a diacylglycerol acyltransferase 2 enzyme having the amino acid sequence as set forth in SEQ ID NO:2 under the control of suitable regulatory sequences; and
  (ii) a source of fatty acids;
(b) growing the cell of step (a) under conditions whereby the at least one gene encoding a diacylglycerol acyltransferase 2 enzyme is expressed, resulting in the transfer of the fatty acids to triacylglycerol; and
(c) optionally recovering the triacylglycerol of step (b).

In an additional preferred embodiment the invention provides a method of increasing the $\omega$-3 or $\omega$-6 fatty acid content of triacylglycerols in a transformed host cell comprising:

(a) providing a transformed host cell comprising:
  (i) at least one gene encoding at least one enzyme of the $\omega$-3/$\omega$-6 fatty acid biosynthetic pathway;
  (ii) at least one gene encoding a diacylglycerol acyltransferase 2 enzyme having the amino acid sequence as set forth in SEQ ID NO:2 under the control of suitable regulatory sequences;
(b) growing the cell of step (a) under conditions whereby the genes of (i) and (ii) are expressed, resulting in the production of at least one $\omega$-3 or $\omega$-6 fatty acid and its transfer to triacylglycerol; and
(c) optionally recovering the triacylglycerol of step (b).

Alternatively the invention provides a method of increasing triacylglycerol content in a transformed host cell comprising:

(a) providing a transformed host cell comprising:
  (i) at least one gene encoding a heterologous diacylglycerol acyltransferase 2 enzyme having the amino acid sequence as set forth in SEQ ID NO:2 under the control of suitable regulatory sequences; and
  (ii) a source of fatty acids;
  wherein said transformed host has a disruption in the gene encoding the native diacylglycerol acyltransferase 2 enzyme;
(b) growing the cell of step (a) under conditions whereby the at least one gene encoding a diacylglycerol acyltransferase 2 enzyme is expressed, resulting in the transfer of the fatty acids to triacylglycerol; and
(c) optionally recovering the triacylglycerol of step (b).

In similar fashion the method provides a method of increasing the $\omega$-3/$\omega$-6 fatty acid content of triacylglycerols in a transformed host cell comprising:

(a) providing a transformed host cell comprising:
  (i) at least one gene encoding at least one enzyme of the $\omega$-3/$\omega$-6 fatty acid biosynthetic pathway;
  wherein said transformed host has a disruption in the gene encoding the native diacylglycerol acyltransferase 2 enzyme;
  (ii) at least one gene encoding a diacylglycerol acyltransferase 2 enzyme having the amino acid sequence as set forth in SEQ ID NO:2 under the control of suitable regulatory sequences;
(b) growing the cell of step (a) under conditions whereby the genes of (i) and (ii) are expressed, resulting in the production of at least one $\omega$-3 or $\omega$-6 fatty acid and its transfer to triacylglycerol; and
(c) optionally recovering the triacylglycerol of step (b).

BRIEF DESCRIPTION OF THE DRAWINGS AND SEQUENCE DESCRIPTIONS

Figure 3:
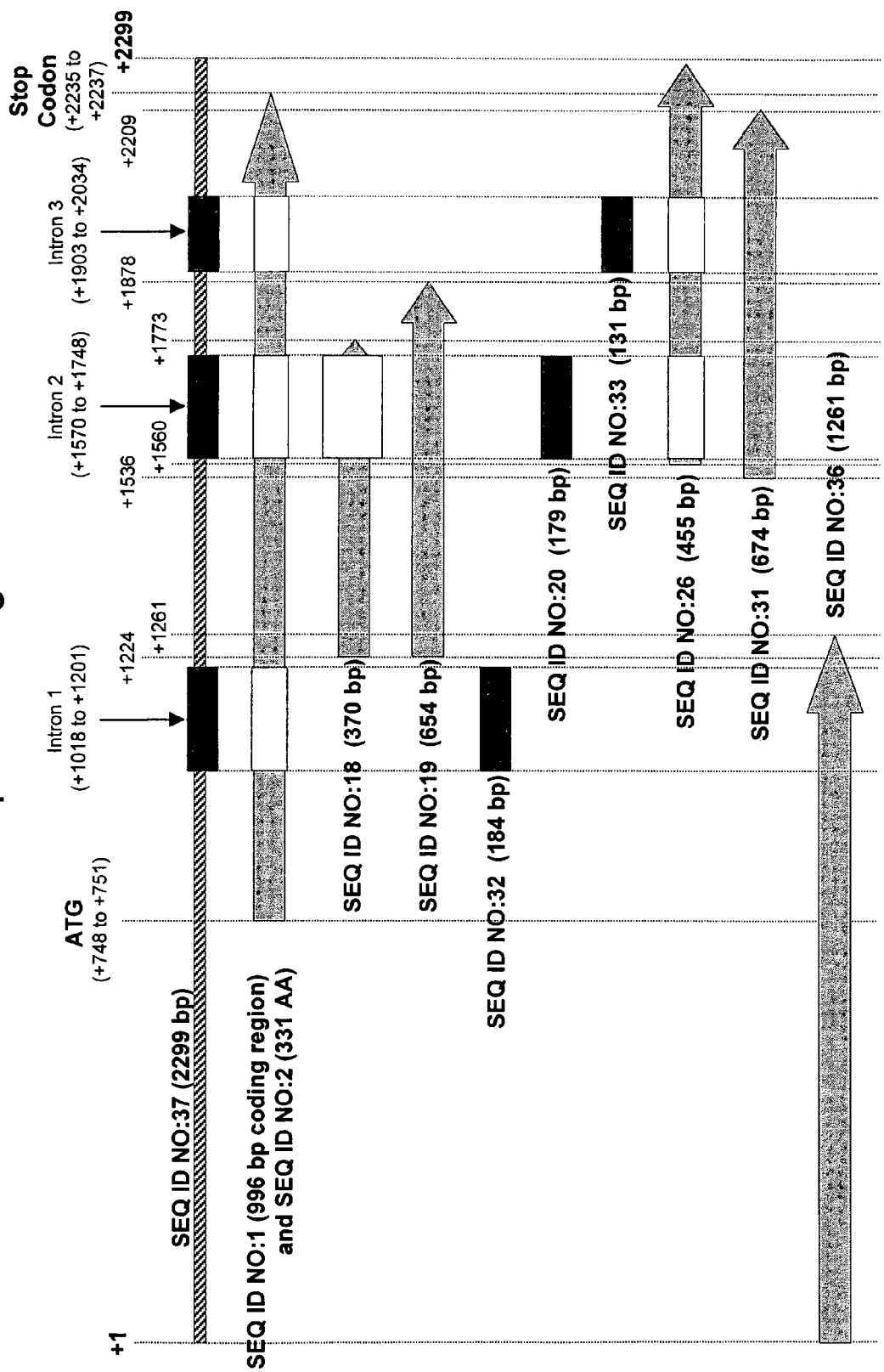

FIG. 3 graphically represents the relationship between SEQ ID NOs:1, 2, 18, 19, 20, 26, 31, 32, 33, 36 and 37, each of which relates to the diacylglycerol acyltransferase 2 (dgat2) gene in *Mortierella alpina*.

FIG. 4A diagrams the development of *Yarrowia lipolytica* strain Y2067U, producing up to 14% EPA in the total lipid fraction. FIG. 4B provides a plasmid map for pKUNF12T6E; FIG. 4C provides a plasmid map for pDMW232; and FIG. 4D provides a plasmid map for pZP3L37.

Figure 5:
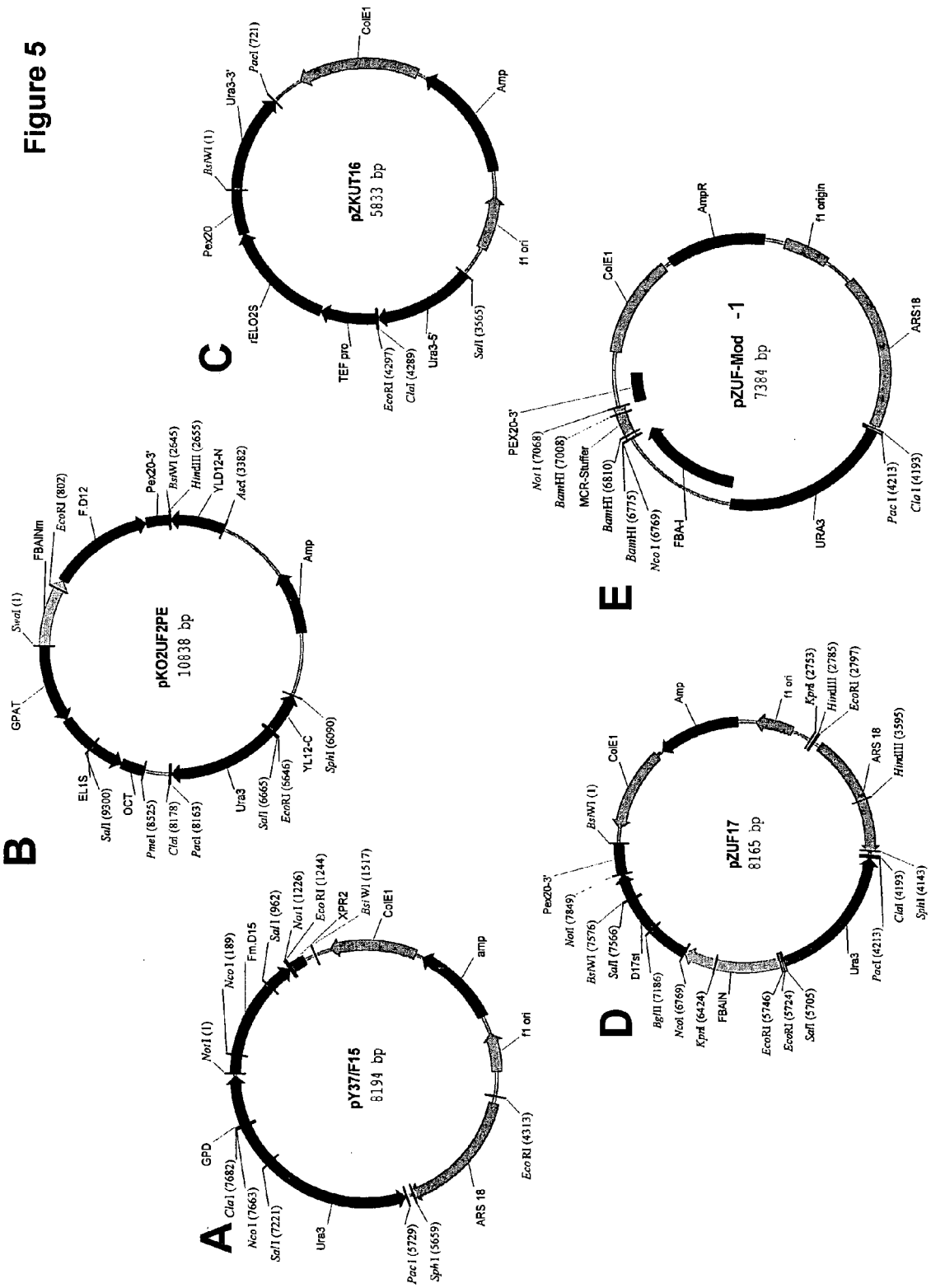

FIG. 5 provides plasmid maps for the following: (A) pY37/F15; (B) pKO2UF2PE; (C) pZKUT16; (D) pZUF17; and (E) pZUF-Mod-1.

The invention can be more fully understood from the following detailed description and the accompanying sequence descriptions, which form a part of this application.

The following sequences comply with 37 C.F.R. §1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–8, 18–20, 26, 31–33, 36, 37, 40–43, 45–48, 50, 51, 53, 54, 58, 59, 62 and 63 are ORFs encoding genes or proteins (or portions thereof) or protein motifs, as identified in Table 1.

TABLE 1

Summary of Gene and Protein SEQ ID Numbers

| Description and Abbreviation | Nucleic acid SEQ ID NO. | Protein SEQ ID NO. |
| --- | --- | --- |
| *Mortierella alpina* diacylglycerol acyltransferase 2 (DGAT2) coding region | 1 (996 bp) | 2 (331 AA) |
| *Mortierella alpina* DGAT2-partial cDNA sequence | 18 (370 bp) | — |
| *Mortierella alpina* DGAT2-internal genomic fragment | 19 (654 bp) | — |
| *Mortierella alpina* DGAT2-intron 1 | 32 (184 bp) | — |
| *Mortierella alpina* DGAT2-intron 2 | 20 (179 bp) | — |
| *Mortierella alpina* DGAT2-intron 3 | 33 (131 bp) | — |
| *Mortierella alpina* DGAT2-3' fragment | 26 (455 bp) | — |
| *Mortierella alpina* DGAT2-3' fragment | 31 (674 bp) | — |
| *Mortierella alpina* DGAT2-5' fragment | 36 (1261 bp) | — |
| *Mortierella alpina* DGAT2-genomic fragment | 37 (2299 bp) | — |
| *Yarrowia lipolytica* DGAT2 ("YI DGAT2") | 3 (2119 bp) 5 (1380 bp) 7 (1068 bp) | 4 (514 AA) 6 (459 AA) 8 (355 AA) |
| Synthetic elongase gene derived from *Mortierella alpina*, codon-optimized for expression in *Yarrowia lipolytica* | 40 (957 bp) | 41 (318 AA) |
| Synthetic Δ6 desaturase, derived from *Mortierella alpina*, codon-optimized for expression in *Yarrowia lipolytica* | 42 (1374 bp) | 43 (457 AA) |
| *Fusarium moniliforme* Δ12 desaturase | 45 (1434 bp) | 46 (477 AA) |
| Synthetic elongase gene derived from *Thraustochytrium aureum*, codon-optimized for expression in *Yarrowia lipolytica* | 47 (819 bp) | 48 (272 AA) |
| *Mortierella alpina* Δ5 desaturase | 50 (1341 bp) | 51 (446 AA) |
| Synthetic Δ17 desaturase gene derived from *Saprolegnia diclina*, codon-optimized for expression in *Yarrowia lipolytica* | 53 (1077 bp) | 54 (358 AA) |
| *Yarrowia lipolytica* Δ12 desaturase | 58 (1936 bp) | 59 (419 AA) |
| Synthetic $C_{16}$ elongase gene derived from *Rattus norvegicus*, codon-optimized for expression in *Yarrowia lipolytica* | 62 (804 bp) | 63 (267 AA) |

SEQ ID NOs:38, 49, 52, 56, 57, 61, 64, 67 and 68 are plasmids as identified in Table 2.

TABLE 2

Summary of Plasmid SEQ ID Numbers

| Plasmid | Corresponding Figure | SEQ ID NO |
| --- | --- | --- |
| pKUNF12T6E | 4B | 38 (12,649 bp) |
| pDMW232 | 4C | 49 (10,945 bp) |
| pZP3L37 | 4D | 52 (12,690 bp) |
| pY37/F15 | 5A | 56 (8,194 bp) |
| pKO2UF2PE | 5B | 57 (10,838 bp) |
| pZKUT16 | 5C | 61 (5,833 bp) |
| pZUF17 | 5D | 64 (8,165 bp) |
| pMDGAT2-17 | — | 67 (8,084 bp) |
| pZUF-MOD-1 | 5E | 68 (7,323 bp) |

SEQ ID NOs:9, 10 and 11 correspond to BD-Clontech Creator Smart® cDNA library kit primers SMART IV oligonucleotide, CDSIII/3' PCR primer and 5'-PCR primer.

SEQ ID NOs:12, 14 and 16 are the degenerate primers identified as MDGAT-FN1, MDGAT-RN1 and MDGAT-RN2, respectively, used for the amplification of a partial putative *Mortierella alpina* DGAT2.

SEQ ID NOs:13, 15 and 17 are the amino acid consensus sequences that correspond to the degenerate primers MDGAT-FN1, MDGAT-RN1 and MDGAT-RN2, respectively.

SEQ ID NOs:21–25 correspond to primers AP, MDGAT-3-1, UAP, MDGAT-3-2 and MDGAT-3-3, respectively, used for genome-walking to isolate the 3'-end region of the *M. alpina* DGAT2.

SEQ ID NOs:27 and 28 correspond to the Genome Walker adaptor from ClonTech's Universal GenomeWalker™ Kit, used for genome-walking to isolate the 3'-end region of the *M. alpina* DGAT2.

SEQ ID NOs:29 and 30 correspond to primers AP1 and AP2, respectively, used for genome-walking to isolate the 3'-end region of the *M. alpina* DGAT2.

SEQ ID NOs:34 and 35 correspond to primers MDGAT-5-1 and MDGAT-5-2, respectively, used for genome-walking to isolate the 5'-end region of the *M. alpina* DGAT2.

SEQ ID NOs:39, 44, 55 and 60 correspond to the following *Yarrowia lipolytica* promoters, respectively: fructose-bisphosphate aldolase+intron (FBAIN; 973 bp), fructose-bisphosphate aldolase (FBA; 1001 bp), fructose-bisphosphate aldolase+modified intron (FBAINm; 924 bp), glycerol-3-phosphate acyltransferase (GPAT; 1130 bp).

SEQ ID NOs:65 and 66 correspond to primers MDGAT-F and MDGAT-R1, respectively, used for cloning of the *M. alpina* DGAT2 ORF.

SEQ ID NOs:69 and 70 correspond to primers pzuf-mod1 and pzuf-mod2, respectively, used for creating "control" plasmid pZUF-MOD-1.

DETAILED DESCRIPTION OF THE INVENTION

In accordance with the subject invention, Applicants have isolated and confirmed the identity of a *Mortierella alpina* gene encoding a diacylglycerol acyltransferase 2 (DGAT2) enzyme useful for transferring fatty acids into storage triacylglycerols (TAGs). This may be useful to alter the quantity of long chain polyunsaturated fatty acids (PUFAs) produced in oleaginous yeast.

The importance of PUFAs are undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA) or α-linolenic acid (ALA); constituents of plasma membranes of cells, where they may be found in such forms as phospholipids or TAGs; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg, J. et al., *Amer. J. Clin Nutr.* 28:958–966 (1975); Dyerberg, J. et al., *Lancet* 2(8081):117–119 (Jul. 15, 1978); Shimokawa, H., *World Rev Nutr Diet*, 88:100–108 (2001); von Schacky, C., and Dyerberg, J., *World Rev Nutr Diet*, 88:90–99 (2001)). And, numerous other studies document wide-ranging health benefits conferred by administration of ω-3 and/or ω-6 fatty acids against a variety of symptoms and diseases (e.g., asthma, psoriasis, eczema, diabetes, cancer).

As such, the subject invention finds many applications. PUFAs, or derivatives thereof, accumulated by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with ARA can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Diacylglycerol acyltransferase" is abbreviated DAG AT or DGAT.

"Diacylglycerol" is abbreviated DAG.

"Triacylglycerols" are abbreviated TAGs.

"Co-enzyme A" is abbreviated CoA.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 3, in the column titled "Shorthand Notation". The remainder of the Table summarizes the common names of ω-3 and ω-6 fatty acids, the abbreviations that will be used throughout the specification and each compounds' chemical name.

TABLE 3

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

"Microbial oils" or "single cell oils" are those oils naturally produced by microorganisms (e.g., algae, oleaginous yeast and filamentous fungi) during their lifespan. The term "oil" refers to a lipid substance that is liquid at 25° C. and usually polyunsaturated. In contrast, the term "fat" refers to a lipid substance that is solid at 25° C. and usually saturated.

"Lipid bodies" refer to lipid droplets that usually are bounded by specific proteins and a monolayer of phospholipid. These organelles are sites where most organisms transport/store neutral lipids. Lipid bodies are thought to arise from microdomains of the endoplasmic reticulum that contain TAG-biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water.

Neutral lipids generally refer to mono-, di-, and/or tri-esters of glycerol with fatty acids, also called monoacylglycerol, diacylglycerol or TAG, respectively (or collectively, acylglycerols). A hydolysis reaction must occur to release free fatty acids from acylglycerols.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

The term "DAG AT" refers to a diacylglycerol acyltransferase (also known as an acyl-CoA-diacylglycerol acyltransferase or a diacylglycerol O-acyltransferase) (EC 2.3.1.20). This enzyme is responsible for the conversion of acyl-CoA and 1,2-diacylglycerol to TAG and CoA (thereby involved in the terminal step of TAG biosynthesis). Two families of DAG AT enzymes exist: DGAT1 and DGAT2. The former family shares homology with the acyl-CoA:cholesterol acyltransferase (ACAT) gene family, while the latter family is unrelated (Lardizabal et al., *J. Biol. Chem.* 276(42):38862–28869 (2001)). A representative DGAT2 enzyme is encoded by the DGA1 gene of *Saccharomyces cerevisiae* (locus NP_014888 of Genbank Accession No. NC_001147; Oelkers et. al. *J. Biol. Chem.* 277:8877 (2002)); a gene encoding DGAT2 isolated from *Mortierella alpina* is provided as SEQ ID NO:1.

The term "PDAT" refers to a phospholipid:diacylglycerol acyltransferase enzyme (EC 2.3.1.158). This enzyme is responsible for the transfer of an acyl group from the sn-2 position of a phospholipid to the sn-3 position of 1,2-diacylglycerol, thus resulting in lysophospholipid and TAG (thereby involved in the terminal step of TAG biosynthesis). This enzyme differs from DGAT (EC 2.3.1.20) by synthesizing TAG via an acyl-CoA-independent mechanism.

The term "PUFA biosynthetic pathway enzyme" refers to any of the following enzymes (and genes which encode said enzymes) associated with the biosynthesis of a PUFA including: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s).

Figure 2:
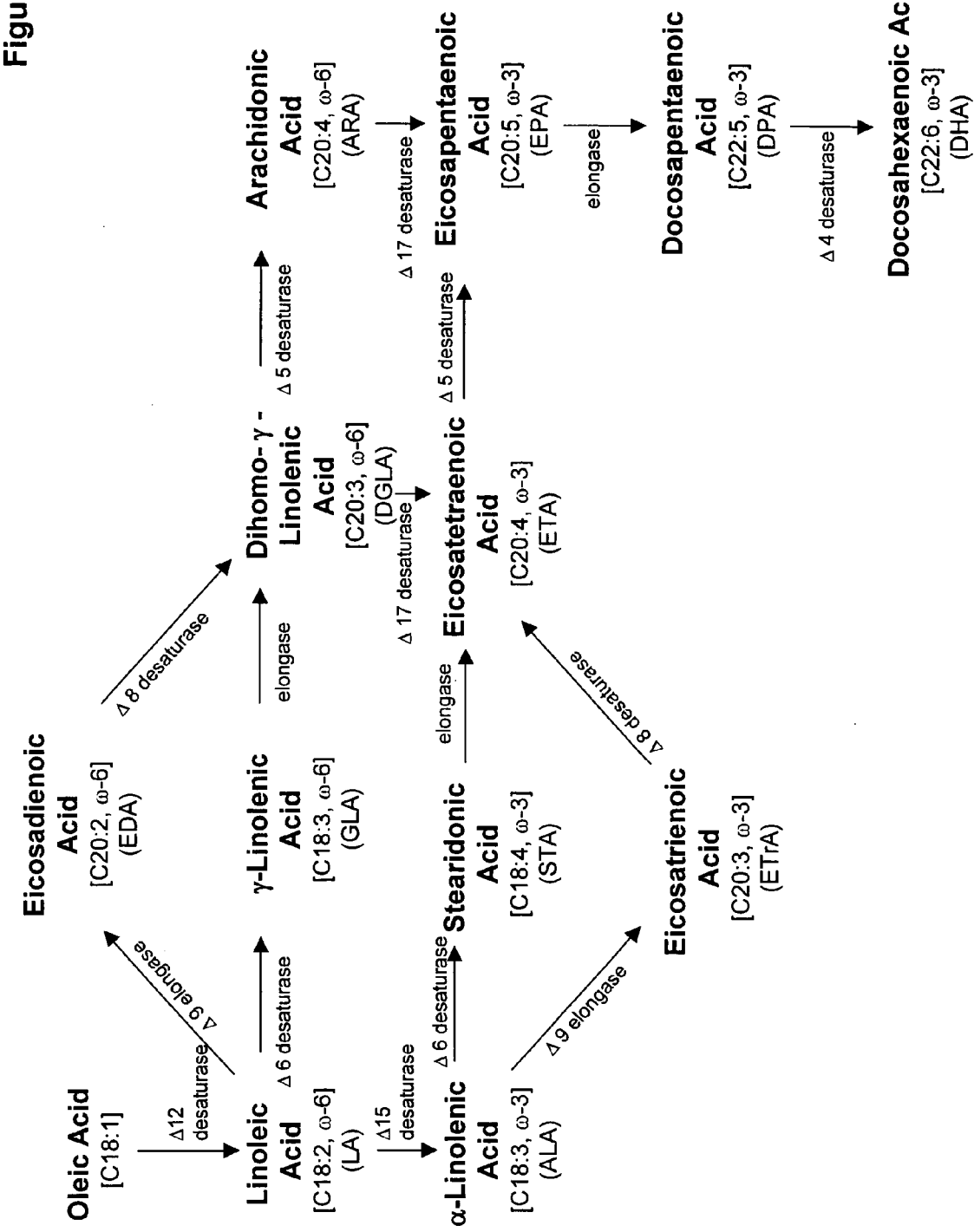
FIG. 2 illustrates the $\omega$-3 and $\omega$-6 fatty acid biosynthetic pathways.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase, Δ5 desaturase, Δ17 desaturase, Δ15 desaturase, Δ9 desaturase, Δ8 desaturase and Δ4 desaturase. A representative pathway is illustrated in FIG. 2, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all of) the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are: Δ12 desaturases that desaturate a fatty acid between the $12^{th}$ and $13^{th}$ carbon atoms numbered from the carboxyl-terminal end of the molecule and that catalyze the conversion of oleic acid to LA; Δ15 desaturases that catalyze the conversion of LA to ALA; Δ17 desaturases that catalyze the conversion of ARA to EPA and/or DGLA to ETA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of eicosadienoic acid (EDA; C20:2) to DGLA and/or eicosatrienoic acid (ETrA; C20:3) to ETA; and Δ9 desaturases that catalyze the conversion of palmitate to palmitoleic acid (16:1) and/or stearate to oleic acid (18:1).

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281–292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA, and EPA to DPA. In general, the substrate selectivity of elongases is somewhat broad but segregated by both chain length and the degree of unsaturation. Accordingly, elongases can have different specificities. For example, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ9 elongase is able to catalyze the conversion of LA and ALA to eicosadienoic acid (EDA; C20:2) and eicosatrienoic acid (ETrA; C20:3), respectively.

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product])* 100, where 'product' includes the immediate product and all products in the pathway derived from it.

The term "oleaginous" refers to those organisms that tend to store their energy source in the form of lipid (Weete, In: Fungal Lipid Biochemistry, $2^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419–25 (1991)).

The term "oleaginous yeast" refers to those microorganisms classified as yeasts that can make oil. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419–25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon substrate" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

As used herein, the terms "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular yeast proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151–153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111–20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized", as it refers to genes or coding regions of nucleic acid molecules, refers to modification of codons such that the altered codons reflect the typical codon usage of the host organism without altering the polypeptide for which the DNA codes.

"Chemically synthesized", as related to a sequence of DNA, means that the component nucleotides were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene(s) and having elements in addition to the foreign gene(s) that facilitate transformation of a particular host cell. "Expression cassette" refers to a specific vector containing a foreign gene(s) and having elements in addition to the foreign gene(s) that allow for enhanced expression of that gene in a foreign host.

The term "homologous recombination" refers to the exchange of DNA fragments between two DNA molecules (during cross over). The fragments that are exchanged are flanked by sites of identical nucleotide sequences between the two DNA molecules (i.e., "regions of homology").

The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis of Fatty Acids and Triacylglycerols

Figure 1:
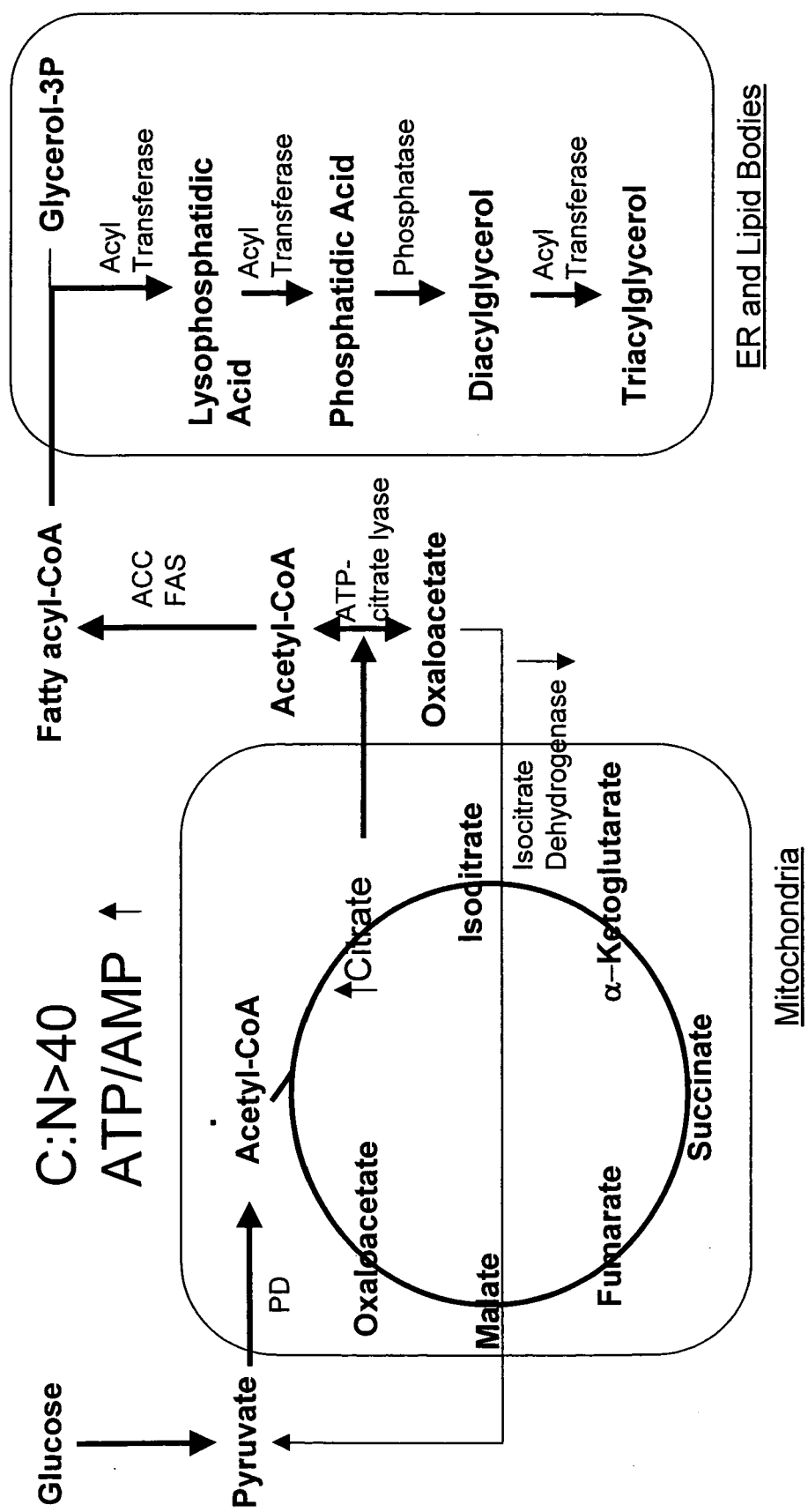
FIG. 1 shows a schematic illustration of the biochemical mechanism for lipid accumulation in oleaginous yeast.

In general, lipid accumulation in oleaginous microorganisms is triggered in response to the overall carbon to nitrogen ratio present in the growth medium (FIG. 1). When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA and oxaloacetate. Acetyl-CoA is the principle building block for de novo biosynthesis of fatty acids. Although any compound that can effectively be metabolized to produce acetyl-CoA can serve as a precursor of fatty acids, glucose is the primary source of carbon in this type of reaction (FIG. 1). Glucose is converted to pyruvate via glycolysis and pyruvate is then transported into the mitochondria where it can be converted to acetyl-CoA by pyruvate dehydrogenase ("PD"). Since acetyl-CoA can not be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. *FASEB J*, 8(15):1248–59 (1994)). First, acetyl-CoA and malonyl-CoA are transferred to the acyl carrier peptide (ACP) of FAS. The acetyl group is then transferred to the malonyl group, forming β-ketobutyryl-ACP and releasing $CO_2$. Secondly, the β-ketobutyryl-ACP undergoes reduction (via β-ketoacyl reductase) and dehydration (via β-hydroxyacyl dehydratase) to form a trans-monounsaturated fatty acyl group. The third reaction occurs when the double bond is reduced by NADPH, yielding a saturated fatty-acyl group two carbons longer than the initial one. The butyryl-group's ability to condense with a new malonyl group and repeat the elongation process is then regenerated. Finally, when the fatty acyl group becomes 16 carbons long, a thioesterase activity hydrolyses it, releasing free palmitate.

Whereas palmitate synthesis occurs in the cytosol, formation of longer chain saturated and unsaturated fatty acid derivates occur in both the mitochondria and endoplasmic reticulum (ER), wherein the ER is the dominant system. Specifically, palmitate (16:0) is the precursor of stearic (18:0), palmitoleic (16:1) and oleic (18:1) acids through the action of elongases and desaturases. For example, palmitate and stearate are converted to their unsaturated derivatives, palmitoleic (16:1) and oleic (18:1) acids, respectively, by the action of a Δ9 desaturase.

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of a DAG acyltransferase (e.g., PDAT, DGAT1 or DGAT2) to form TAG (FIG. 1).

A wide spectrum of fatty acids can be incorporated into TAGs, including saturated and unsaturated fatty acids and short-chain and long-chain fatty acids. Some non-limiting examples of fatty acids that can be incorporated into TAGs by acyltransferases (e.g., DGAT2) include: capric (10:0), lauric (12:0), myristic (14:0), palmitic (16:0), palmitoleic (16:1), stearic (18:0), oleic (18:1), vaccenic (18:1), linoleic (18:2), eleostearic (18:3), γ-linolenic (18:3), α-linolenic (18:3), stearidonic (18:4), arachidic (20:0), eicosadienoic (20:2), dihomo-γ-linoleic (20:3), eicosatrienoic (20:3), arachidonic (20:4), eicosa-tetraenoic (20:4), eicosa-pentaenoic (20:5), behenic (22:0), docosa-pentaenoic (22:5), docosa-hexaenoic (22:6), lignoceric (24:0), nervonic (24:1), cerotic (26:0), and montanic (28:0) fatty acids. In preferred embodiments of the present invention, incorporation of PUFAs into TAG is most desirable.

Genes Encoding DGAT2

Historically, DGAT1 (responsible for the third acyl transferase reaction, wherein an acyl-CoA group is transferred from acyl-CoA to the sn-3 position of DAG to form TAG) was thought to be the only enzyme specifically involved in TAG synthesis. This enzyme was known to be homologous to acyl-CoA:cholesterol acyltransferases (ACATs); however, recent studies have identified a new family of DAG acyltransferase enzymes that are unrelated to the ACAT gene family. Thus, nomenclature now distinguishes between the DAG acyltransferase enzymes that are related to the ACAT gene family (DGAT1 family) versus those that are unrelated (DGAT2 family) (Lardizabal et al., *J. Biol. Chem.* 276(42): 38862–28869 (2001)). Members of the DGAT2 family appear to be present in all major phyla of eukaryotes (fungi, plants, animals and basal eukaryotes).

Many genes encoding DGAT2 enzymes have been identified through genetic means and the DNA sequences of some of these genes are publicly available. For example, some non-limiting examples include the following GenBank Accession Numbers: NC_001147 (locus NP_014888; *Saccharomyces cerevisiae*); NM_012079 (human); NM_127503, AF051849 and AJ238008 (*Arabidopsis thaliana*); NM_026384, NM_010046 and AB057816 (mouse); AY093657 (pig); AB062762 (rat); AF221132 (*Caenorhabditis elegans*); AF391089 and AF391090 (*Mortierella ramanniana*); AF129003 (*Nicotiana tabacum*); and, AF251794 and AF164434 (*Brassica napus*). Additionally, the patent literature provides many additional DNA sequences of DGAT2 genes (and/or details concerning several of the genes above and their methods of isolation). See, for example: US 2003/124126 (Cases et al.); WO 2001/034814 (Banas et al.); and US 2003/115632, US2003/0028923 and US 2004/0107459 (Lardizabal et al.). The work of Lardizabal et al. includes DNA sequences of DGAT2s from, e.g., *Mortierella ramanniana, Neurospora crassa* (GenBank Accession No. CAE76475), *Saccharomyces cerevisiae* (see also Sorger and Daum, *J. Bacteriol.* 184(2):519–524 (2002)), *Hordeum vulgare, Zea mays, Glycine max, Triticum aestivum, Drosophilia, Homo sapiens, Schizosaccharomyces pombe* (see also Zhang et al., *J. Biol. Chem.* 278(47):47145–47155 (2003)), *Candida albicans* and *Arabidopsis thaliana*. Despite disclosure of several complete and incomplete sequences encoding DGAT2 (supra), very few of these sequences have been shown to have DGAT2 activity. The exceptions include the work of: 1.) Bouvier-Nave, P. et al. (*Biochem. Soc. Trans.* 28(6):692–695 (2000)), wherein the DGAT2 of the nematode worm *Caenorhabditis elegans* was expressed in *Saccharomyces cerevisiae*, leading to an increase in TAG content and in microsomal oleyl-CoA:DAG acyltransferase activity; and, 2.) Lardizabal et al. (supra), wherein two DGAT2s of the fungus *Mortierella ramanniana* and one DGAT2 from the fungus *Neurospora crassa* were expressed in insect cells, leading to high levels of DGAT activity on membranes isolated from those cells. In addition to these demonstrations where oil biosynthesis was increased by over-expression of DGAT2, disruption of the genes encoding DGAT2 have also been shown to result in a decrease in the cellular TAG content (Oelkers et al., *J Biol. Chem.* 277(11):8877–81 (2002); Sandager et al., *J Biol. Chem.* 277:6478–6482 (2002); Sorger and Daum, *J. Bacteriol.* 184:519–524 (2002)).

Most recently, a single DGAT2 enzyme from the oleaginous yeast *Yarrowia lipolytica* has been isolated and characterized in co-pending U.S. patent application Ser. No. 10/882,760. Briefly, following cloning of a partial putative DGAT2 DNA fragment from *Y. lipolytica*, targeted disruption of the endogenous *Y. lipolytica* gene was carried out to test the identity of the fragment. Lower oil content in the disrupted strain confirmed that the native DGAT2 activity was disrupted. Subsequently, a full-length *Y. lipolytica* DGAT2 gene (2119 bp; SEQ ID NO:3) was assembled, which included three nested open reading frames [ORF 1: nucleotides +291 to +1835 of SEQ ID NO:3, corresponding to a deduced encoded amino acid sequence of 514 residues (SEQ ID NO:4); ORF 2: nucleotides +456 to +1835 of SEQ ID NO:3 (i.e., SEQ ID NO:5), corresponding to a deduced encoded amino acid sequence of 459 residues (SEQ ID NO:6); and ORF 3: nucleotides +768 to +1835 of SEQ ID NO:3 (i.e., SEQ ID NO:7), corresponding to a deduced encoded amino acid sequence of 355 residues (SEQ ID NO:8)].

Biosynthesis of Omega-3 and Omega-6 Polyunsaturated Fatty Acids

The metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 2). This requires a series of desaturation and elongation enzymes. Specifically, oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase. In like manner, linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically, 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to eicosadienoic acid (EDA; C20:2) and eicosatrienoic acid (ETrA; C20:3), respectively. A Δ8 desaturase then converts these products to DGLA and ETA, respectively.

Many microorganisms, including algae, bacteria, molds, fungi and yeast, can synthesize PUFAs and omega fatty acids in the ordinary course of cellular metabolism. Particularly well-studied are fungi including *Schizochytrium aggregatm*, species of the genus *Thraustochytrium* and *Mortierella alpina*. Additionally, many dinoflagellates (Dinophyceaae) naturally produce high concentrations of PUFAs. As such, a variety of desaturase and elongase genes involved in PUFA production have been identified through genetic means and the DNA sequences of some of these genes are publicly available. For instance, the GenBank Accession Numbers of some non-limiting examples are: AY131238, Y055118, AY055117, AF296076, AF007561, L11421, NM_031344, AF465283, AF465281, AF110510, AF465282, AF419296, AB052086, AJ250735, AF126799, AF126798 (Δ6 desaturases); AF199596, AF226273, AF320509, AB072976, AF489588, AJ510244, AF419297, AF07879, AF067654, AB022097 (Δ5 desaturases); AF489589.1, AY332747 (Δ4 fatty acid desaturases); AAG36933, AF110509, AB020033, AAL13300, AF417244, AF161219, AY332747, AAG36933, AF110509, AB020033, AAL13300, AF417244, AF161219, X86736, AF240777, AB007640, AB075526, AP002063 (Δ12 desaturases); NP_441622, BAA18302, BAA02924, AAL36934 (Δ15 desaturases); AF338466, AF438199, E11368, E11367, D83185, U90417, AF085500, AY504633, NM_069854, AF230693 (Δ9 desaturases); and AX464731, NM_119617, NM_134255, NM_134383, NM_134382, NM_068396, NM_068392, NM_070713, NM_068746, NM_064685 (elongases).

Additionally, the patent literature provides many additional DNA sequences of genes (and/or details concerning several of the genes above and their methods of isolation) involved in PUFA production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); WO 00/12720 and U.S. 2002/0139974A1 (elongases); U.S. 2003/0196217 A1 (Δ17 desaturase); WO 00/34439 (Δ8 desaturases); and, WO 02/090493 (Δ4 desaturases). Each of these patents and applications are herein incorporated by reference in their entirety.

Depending upon the host cell, the availability of substrate, and the desired end product(s), several desaturases and elongases are of interest for use in production of PUFAs. Considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired fatty acid substrate.

Sequence Identification of *Mortierella alpina* DGAT2 Acyltransferase

Despite the availability of several genes encoding DGAT2 (supra) that could be used for heterologous expression in oleaginous yeast (e.g., *Yarrowia lipolytica*), only three DGAT2 genes have been isolated and characterized from oleaginous organisms (e.g., from *Mortierella ramanniana* and *Yarrowia lipolytica*). And, none of the three DGAT2 genes from oleaginous organisms are expected to favor longer chain PUFAs (i.e., those PUFAs having a chain length equal to or greater than $C_{20}$). In the present invention, a DGAT2 gene has been isolated from *Mortierella alpina*. *M. alpina* is an organism that naturally accumulates fatty acids having chain-lengths equal to or greater than $C_{20}$ in its TAG fraction, thus indicating that the DGAT2 is likely to have the desired substrate specificity.

Comparison of the DGAT2 nucleotide base and deduced amino acid sequences to public databases, using a BLAST algorithm (Altschul, S. F., et al., *Nucleic Acids Res.* 25:3389–3402 (1997)), reveals that the most similar known sequences are about 47% identical to the amino acid sequence of DGAT2 reported herein over a length of 331 amino acids. Preferred amino acid fragments are at least about 70%–80% identical to the sequences herein, where those sequences that are 85%–90% identical are particularly suitable and those sequences that are about 95% identical are most preferred. Similarly, preferred DGAT2 encoding nucleic acid sequences corresponding to the instant ORF are those encoding active proteins and which are at least about 70%–80% identical to the nucleic acid sequences encoding DGAT2 reported herein, where those sequences that are 85%–90% identical are particularly suitable and those sequences that are about 95% identical are most preferred.

Isolation of Homologs

DGAT2 nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the DGAT2 described herein could be isolated directly by using all or a portion of the instant nucleic acid fragments as DNA hybridization probes to screen libraries from any desired yeast or fungus using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33–50, IRL: Herndon, V A; and Rychlik, W., In *Methods in Molecular Biology*, White, B. A. Ed., (1993) Vol. 15, pp 31–39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the instant DGAT2 sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia Inc.) (about 300–500 kdal), polyvinylpyrrolidone (about 250–500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can then be used to screen DNA-expression libraries to isolate full-length DNA clones of interest (Lerner, R. A. *Adv. Immunol.* 36:1 (1984); Maniatis, supra).

Gene Optimization for Improved Heterologous Expression

It may be desirable to modify the expression of the instant DGAT2 and/or PUFA biosynthetic pathway enzymes to achieve optimal conversion efficiency of each, according to the specific TAG composition of interest. As such, a variety of techniques can be utilized to improve/optimize the expression of a polypeptide of interest in an alternative host. Two such techniques include codon-optimization and mutagenesis of the gene.

Codon Optimization

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Thus, the coding sequence for a polypeptide having acyltransferase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

Thus, for example, it may be desirable to modify a portion of the codons encoding the polypeptide having DGAT2 activity, to enhance the expression of the gene in *Yarrowia lipolytica*. The codon usage profile and the consensus sequence around the 'ATG' translation initiation codon for this particular organism are taught in co-pending U.S. patent application Ser. No. 10/840,478 (herein incorporated entirely by reference); likewise, a method for rapid synthesis of genes optimized for expression in *Yarrowia lipolytica* is also provided.

Mutagenesis

Methods for synthesizing sequences and bringing sequences together are well established in the literature. For example, in vitro mutagenesis and selection, site-directed mutagenesis, error prone PCR (Melnikov et al., *Nucleic Acids Research,* 27(4):1056–1062 (Feb. 15, 1999)), "gene shuffling" or other means can be employed to obtain mutations of naturally occurring DGAT2 genes. This would permit production of a polypeptide having acyltransferase activity in vivo with more desirable physical and kinetic parameters for function in the host cell (e.g., a longer half-life or a higher rate of synthesis of TAGs from fatty acids).

If desired, the regions of a DGAT2 polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a DGAT2 polypeptide important for activity. A mutated construct is expressed, and the ability of the resulting altered protein to function as an acyltransferase is assayed. Such structure-function analysis can determine which regions may be deleted, which regions tolerate insertions, and which point mutations allow the mutant protein to function in substantially the same way as the native acyltransferase.

All such mutant proteins and nucleotide sequences encoding them that are derived from the DGAT2 described herein are within the scope of the present invention.

Microbial Production of Fatty Acids and Triacylglycerols

Microbial production of fatty acids and TAGs has several advantages over purification from natural sources such as fish or plants. For example: (1) many microbes are known with greatly simplified oil compositions compared with those of higher organisms, making purification of desired components easier; (2) microbial production is not subject to fluctuations caused by external variables, such as weather and food supply; (3) microbially produced oil is substantially free of contamination by environmental pollutants; and, (4) microbial oil production can be manipulated by controlling culture conditions, notably by providing particular substrates for microbially expressed enzymes, or by addition of compounds or genetic engineering approaches to suppress undesired biochemical pathways. With respect to the production of ω-3 and/or ω-6 fatty acids in particular, and TAGs containing those PUFAs, additional advantages are incurred since microbes can provide fatty acids in particular forms that may have specific uses; and, recombinant microbes provide the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs.

Thus, knowledge of the sequence of the present DGAT2 will be useful for manipulating fatty acid biosynthesis and accumulation in oleaginous yeast, and particularly, in *Yarrowia lipolytica*. This may require metabolic engineering directly within the fatty acid or TAG biosynthetic pathways or additional manipulation of pathways that contribute carbon to the fatty acid biosynthetic pathway. Methods useful for manipulating biochemical pathways are well known to those skilled in the art.

Metabolic Engineering to Up-Regulate Genes and Biosynthetic Pathways Affecting Fatty Acid Synthesis and Oil Accumulation in Oleaginous Yeast It is expected that introduction of chimeric genes encoding the DGAT2 described herein, under the control of the appropriate promoters, will result in increased transfer of fatty acids to storage TAGs. As such, the present invention encompasses a method for increasing the TAG content in an oleaginous yeast comprising expressing the DGAT2 enzyme of the present invention in a transformed oleaginous yeast host cell producing a fatty acid, such that the fatty acid is transferred to the TAG pool.

Additional copies of DGAT2 genes may be introduced into the host to increase the transfer of fatty acids to the TAG fraction. Expression of the genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910, 141). Yet another approach to increase expression of heterologous genes is to increase the translational efficiency of the encoded mRNAs by replacement of codons in the native gene with those for optimal gene expression in the selected host microorganism.

In one specific embodiment, the present invention encompasses a method of increasing the ω-3 and ω-6 fatty acid content of TAGs in an oleaginous yeast, since it is possible to introduce an expression cassette encoding each of the enzymes necessary for ω-3 and ω-6 fatty acid biosynthesis into the organism (since naturally produced PUFAs in these organisms are limited to 18:2 (i.e., LA), and less commonly 18:3 (i.e., ALA) fatty acids). Thus, the method comprises:
  a) providing a transformed oleaginous yeast host cell possessing at least one gene encoding at least one enzyme of the ω-3/ω-6 fatty acid biosynthetic pathway and the DGAT2 enzyme of the present invention;
  b) growing the yeast cells of step (a) in the presence of a fermentable carbon substrate, whereby the gene(s) of the ω-3/ω-6 fatty acid biosynthetic pathway and the DGAT2 are expressed, whereby a ω-3 and/or ω-6 fatty acid is produced, and whereby the ω-3 and/or ω-6 fatty acid is transferred to TAGs.

A variety of PUFA products can be produced (prior to their transfer to TAGs), depending on the fatty acid substrate and the particular genes of the ω-3/ω-6 fatty acid biosynthetic pathway that are transformed into the host cell. As such, production of the desired fatty acid product can occur directly (wherein the fatty acid substrate is converted directly into the desired fatty acid product without any intermediate steps or pathway intermediates) or indirectly (wherein multiple genes encoding the PUFA biosynthetic pathway may be used in combination, such that a series of reactions occur to produce a desired PUFA). Specifically, for example, it may be desirable to transform an oleaginous yeast with an expression cassette comprising a Δ12 desaturase, Δ6 desaturase, an elongase, a Δ5 desaturase and a Δ17 desaturase for the overproduction of EPA. As is well known to one skilled in the art, various other combinations of the following enzymatic activities may be useful to express in a host in conjunction with the DGAT2 described herein: a Δ15 desaturase, a Δ4 desaturase, a Δ5 desaturase, a Δ6 desaturase, a Δ17 desaturase, a Δ9 desaturase, a Δ8 desaturase and/or an elongase(s) (see FIG. 2). The particular genes included within a particular expression cassette will depend on the host cell (and its PUFA profile and/or desaturase profile), the availability of substrate and the desired end product(s).

Thus, within the context of the present invention, it may be useful to modulate the expression of the TAG biosynthetic pathway by any one of the methods described above. For example, the present invention provides a gene encoding a key enzyme in the fatty acid biosynthetic pathway leading to the storage of TAGs. This gene encodes the DGAT2 enzyme. It will be particularly useful to express this gene in oleaginous yeast to maximize production and accumulation of TAGs using various means for metabolic engineering of the host organism. In preferred embodiments, modification of the expression levels of this gene in combination with expression of ω-3/ω-6 biosynthetic genes can be utilized to maximize production and accumulation of preferred PUFAs in the TAG pool.

Metabolic Engineering to Down-Regulate Undesirable Genes and Biosynthetic Pathways Affecting Fatty Acid Synthesis and Oil Accumulation in Oleaginous Yeast In some embodiments, it may be useful to disrupt or inactivate a host organism's native DGAT2, based on the complete sequences described herein, the complement of those complete sequences, substantial portions of those sequences, codon-optimized acyltransferases derived therefrom, and those sequences that are substantially homologous thereto. In an alternate embodiment, a transformant host organism comprising a disruption or inactivation of its native DGAT2 may then be advantageously transformed to express a heterologous DGAT2 (e.g., if the heterologous DGAT2 has different substrate specificity than the native DGAT2).

For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al., *J. Bacteriol.* 171:4617–4622 (1989); Balbas et al., *Gene* 136:211–213 (1993); Gueldener et al., *Nucleic Acids Res.* 24:2519–2524 (1996); and Smith et al., *Methods Mol. Cell. Biol.* 5:270–277(1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, Mass.; or Deshpande, Mukund V., *Appl. Biochem. Biotechnol.*, 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

As described in U.S. Patent Application No. 60/624,812, the Applicants have discovered that expression of heterologous acyltransferases in conjunction with knockouts of the corresponding native *Yarrowia lipolytica* acyltransferase can significantly increase the overall long-chain w-3 PUFAs that are produced in transformant *Yarrowia lipolytica* host cells engineered for PUFA biosynthesis. This manipulation is thought to reduce substrate competition between the native and heterologous acyltransferase; and, when the heterologous acyltransferase has specificity for those fatty acids that are 18:3 and greater (in comparison to the native enzymes that may not efficiently catalyze reactions with longer-chain fatty acids since naturally produced PUFAs in *Yarrowia lipolytica* are limited to 18:2 fatty acids) likely enables more efficient acyltransferase reactions to occur within the transformant host. Thus, within the context of the present invention, it may be useful to disrupt or inactivate a host organism's native DGAT2 (e.g., the *Yarrowia lipolytica* DGAT2 encoded by SEQ ID NO:4, 6 or 8) that does not have specificity for long-chain PUFAs (e.g., 20:0, 22:0) or that has difficulty efficiently synthesizing TAGs comprising fatty acids that are 18:3 and greater in length (e.g., EPA). Then, the heterologous (or "foreign") DGAT2 of the present invention (i.e. SEQ ID NO:2) could be expressed to enable increased accumulation of long chain PUFAs in the organism's TAG fraction, since substrate competition between the native and heterologous acyltransferase would be reduced. One skilled in the art would readily be able to apply the teachings herein toward the advantageous manipulation of DGAT2 acyltransferases in other oleaginous organisms.

In conjunction with this approach, or alternatively, it may be necessary to disrupt genes and pathways that diminish the existing fatty acid pool and/or that hydrolyze TAGs to regulate (and/or maximize) TAG accumulation.

Expression Systems, Cassettes and Vectors

The gene and gene product of the instant sequences described herein may be produced in microbial host cells, particularly in the cells of oleaginous yeast (e.g., *Yarrowia lipolytica*). Expression in recombinant microbial hosts may be useful for the transfer of various fatty acids to TAGs.

Microbial expression systems and expression vectors containing regulatory sequences that direct high level expression of foreign proteins are well known to those skilled in the art. Any of these could be used to construct chimeric genes for production of the gene products of the instant DGAT2 sequences. These chimeric genes could then be introduced into appropriate microorganisms via transformation to provide high level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. patent application Ser. No. 10/869,630, incorporated herein by reference), phosphoglycerate mutase (see U.S. patent application Ser. No. 10/869,630, incorporated herein by reference), fructose-bisphosphate aldolase (see U.S. patent application Ser. No. 10/987,548, incorporated herein by reference), phosphoglucose-isomerase, phosphoglycerate kinase, glycerol-3-phosphate O-acyltransferase (see U.S. Patent Application No. 60/610,060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest (see, e.g., U.S. patent application Ser. No. 10/840,478 for specific teachings applicable for *Yarrowia lipolytica*).

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the DGAT2 enzyme described herein.

Preferred Microbial Hosts for Recombinant Expression of DGAT2

Host cells for expression of the instant DGAT2 gene and nucleic acid fragments may include microbial hosts that grow on a variety of feedstocks, including simple or complex carbohydrates, organic acids and alcohols and/or hydrocarbons over a wide range of temperature and pH values. Although the gene described in the instant invention has been isolated for expression in an oleaginous yeast, and in particular *Yarrowia lipolytica*, it is contemplated that because transcription, translation and the protein biosynthetic apparatus is highly conserved, any bacteria, yeast, algae and/or filamentous fungus will be a suitable host for expression of the present nucleic acid fragments.

Preferred microbial hosts are oleaginous organisms, such as oleaginous yeast. These oleaginous organisms are naturally capable of oil synthesis and accumulation, wherein the total oil content can comprise greater than about 25% of the cellular dry weight, more preferably greater than about 30% of the cellular dry weight and most preferably greater than about 40% of the cellular dry weight. Additionally, there is basis for the use of these organisms for the production of PUFA's, as seen in co-pending U.S. patent applications Ser. No. 10/840,579 and No. 60/624,812, each incorporated entirely by reference herein.

Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982, ATCC #90812 and/or LGAM S(7)1 (Papanikolaou S., and Aggelis G., *Bioresour. Technol.* 82(1):43–9 (2002)).

Transformation of Microbial Hosts

Once the DNA encoding a polypeptide suitable for expression in an oleaginous yeast has been obtained, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [Methods in *Enzymology*, 194:186–187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol.* 48(2):232–235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the gene products of the instant sequence (and optionally other PUFA enzymes that are expressed within the host cell), may be produced by the host either naturally or transgenically, or they may be provided exogenously.

Fermentation Processes for Triacylglycerol Biosynthesis and Accumulation

The transformed microbial host cell is grown under conditions that optimize activity of fatty acid biosynthetic genes and acyltransferase genes. This leads to production of the greatest and the most economical yield of fatty acids, which can in turn be transferred to TAGs for storage. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10–22 carbons.

Nitrogen may be supplied from an inorganic (e.g., $(NH_4)_2SO_4$) or organic source (e.g., urea, glutamate). In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for fatty acid production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61–97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of fatty acids and TAGs in oleaginous yeast cells requires a two-stage process, since the metabolic state must be "balanced" between growth and synthesis/storage of fats. Thus, most preferably, a two-stage fermentation process is necessary for the production of oils in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of TAGs.

Although cells are typically grown at about 30° C., some studies have shown increased synthesis of unsaturated fatty acids at lower temperatures (Yongmanitchai and Ward, *Appl. Environ. Microbiol.* 57:419–25 (1991)). Based on process economics, this temperature shift should likely occur after the first phase of the two-stage fermentation, when the bulk of the organisms' growth has occurred.

It is contemplated that a variety of fermentation process designs may be applied, where commercial production of fatty acids and TAGs using the instant DGAT2 is desired. For example, commercial production of TAGs containing PUFAs from a recombinant microbial host may be produced by a batch, fed-batch or continuous fermentation process.

A batch fermentation process is a closed system wherein the media composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional substrates (i.e., carbon and nitrogen sources) to the medium. In batch processes the metabolite and biomass compositions of the system change constantly up to the time the culture is terminated. In a typical batch process, cells moderate through a static lag phase to a high-growth log phase and finally to a stationary phase, wherein the growth rate is diminished or halted. Left untreated, cells in the stationary phase will eventually die. A variation of the standard batch process is the fed-batch process, wherein the substrate is continually added to the fermentor over the course of the fermentation process. A fed-batch process is also suitable in the present invention. Fed-batch processes are useful when catabolite repression is apt to inhibit the metabolism of the cells or where it is desirable to have limited amounts of substrate in the media at any one time. Measurement of the substrate concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production of fatty acids using the instant DGAT2 may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification of Fatty Acids

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463–491 (1992)). A brief review of downstream processing is also available by A. Singh and O. Ward (*Adv. Appl. Microbiol.* 45:271–312 (1997)).

In general, means for the purification of fatty acids (including PUFAs) may include extraction with organic solvents, sonication, supercritical fluid extraction (e.g., using carbon dioxide), saponification and physical means such as presses, or combinations thereof. Of particular interest is extraction with methanol and chloroform in the presence of water (E. G. Bligh & W. J. Dyer, *Can. J. Biochem. Physiol.* 37:911–917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation, iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

DESCRIPTION OF PREFERRED EMBODIMENTS

The ultimate goal of the work described herein is the development of an oleaginous yeast that accumulates TAGs enriched in ω-3 and/or ω-6 PUFAs. Toward this end, acyltransferases must be identified that function efficiently in oleaginous yeast to enable synthesis and high accumulation of preferred TAGs in these hosts. Specifically, modification of the expression levels of these acyltransferases will enable increased transfer of fatty acids (and particularly, PUFAs having chain-lengths equal to or greater than $C_{20}$) to TAGs. Thus, identification of efficient acyltransferases is necessary for the manipulation of the amount of ω-3/ω-6 PUFAs incorporated into the TAG fraction produced in transformant host cells.

In the present invention, Applicants have isolated and cloned the gene from *Mortierella alpina* that encodes DGAT2. Based on the ability of the native organism to synthesize ARA at concentrations greater than 50% of the total fatty acids (TFAs), it was expected that the DGAT2 would have excellent efficient synthesizing TAGs comprising long chain fatty acids. Confirmation of this gene's activity was provided based upon sequence homology with DGAT2 from other species.

The Applicants hypothesized that the *M. alpina* acyltransferase gene encoding DGAT2 would be useful for expression in various microbial hosts, and particularly for over-expression in oleaginous yeast whose native DGAT2 may not have the substrate specificity necessary to enable efficient incorporation of PUFAs having chain-lengths equal to or greater than $C_{20}$ into the TAG fraction. To test this, the *M. alpina* DGAT2 was over-expressed in an engineered strain of *Yarrowia lipolytica* producing about 14% EPA. Transformant strains possessed increased oil content (total fatty acids as a % of dry cell weight) relative to the parental strains. Additional benefits may result, since expression of the DGAT2 of the instant invention can also be put under the control of strong constitutive or regulated promoters that do not have the regulatory constraints of the native gene.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP10 cells and *E. coli* Electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., (Madison, Wis.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

Yarrowia lipolytica strains ATCC #20362, #76982 and #90812 were purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol Biotechnol.* 48(2):232–235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of leucine and/or uracil were added as appropriate to a final concentration of 0.01% (thereby producing "MMLe" and "MMU" selection media, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Finally, for the "two-stage growth conditions" designed to promote conditions of oleaginy, High Glucose Media ("HGM") was prepared as follows: 14 g/L $KH_2PO_4$, 4 g/L $K_2HPO_4$, 2 g/L $MgSO_4 \cdot 7H_2O$, 80 g/L glucose (pH 6.5).

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911–917 (1959)). Fatty acid methyl esters were prepared by transesterification of the lipid extract with sodium methoxide (Roughan, G., and Nishida I. *Arch Biochem Biophys.* 276 (1):38–46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5–10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Preparation of *Mortierella alpina* Genomic DNA and cDNA

The present Example describes the preparation of genomic DNA and cDNA from *Mortierella alpina* (ATCC #16266).

Preparation of Genomic DNA from *Mortierella Alpina*

Genomic DNA was isolated from *Mortierella alpina* (ATCC #16266) using a QiaPrep Spin Miniprep Kit (Qiagen, Catalog #627106). Cells grown on a YPD agar plate (2% Bacto-yeast extract, 3% Bactor-peptone, 2% glucose, 2.5% bacto-agar) were scraped off and resuspended in 1.2 mL of kit buffer P1. The resuspended cells were placed in two 2.0 mL screw cap tubes, each containing 0.6 mL glass beads (0.5 mm diameter). The cells were homogenized at the HOMOGENIZE setting on a Biospec (Bartlesville, Okla.) mini bead beater for 2 min. The tubes were then centrifuged at 14,000 rpm in an Eppendorf microfuge for 2 min. The supernatant (0.75 mL) was transferred to three 1.5 mL microfuge tubes. Equal volumes of kit buffer P2 were added to each tube. After mixing the tubes by inversion three times, 0.35 mL of buffer N3 was added to each tube. The contents of each tube were again mixed by inversion for a total of five times. The mixture was centrifuged at 14,000 rpm in an Eppendorf microfuge for 5 min. The supernatant from each tube was transferred individually into 3 separate kit spin columns. The columns were then subjected to the following steps: centrifugation (1 min at 14,000 rpm), wash once with buffer PE, centrifugation (1 min at 14,000 rpm), and then a final centrifugation (1 min at 14,000 rpm). Buffer EB (50 μl) was added to each column and let stand for 1 min. The genomic DNA was then eluted by centrifugation at 14,000 rpm for 1 min.

Preparation of cDNA from *Mortierella alpina* cDNA of *Mortierella alpina* was prepared using the BD-Clontech Creator Smart® cDNA library kit (Mississauga, ON, Canada), according to the manufacturer's protocol.

Specifically, *M. alpina* strain ATCC #16266 was grown in 60 mL YPD medium (2% Bacto-yeast extract, 3% Bactor-peptone, 2% glucose) for 3 days at 23° C. Cells were pelleted by centrifugation at 3750 rpm in a Beckman GH3.8 rotor for 10 min and resuspended in 6×0.6 mL Trizole reagent (Invitrogen). Resuspended cells were transferred to six 2 mL screw cap tubes each containing 0.6 mL of 0.5 mm glass beads. The cells were homogenized at the HOMOGENIZE setting on a Biospec (Bartlesville, Okla.) mini bead beater for 2 min. The tubes were briefly spun to settle the beads. Liquid was transferred to 4 fresh 1.5 mL microfuge tubes and 0.2 mL chloroform:isoamyl alcohol (24:1) was added to each tube. The tubes were shaken by hand for 1 min and let stand for 3 min. The tubes were then spun at 14,000 rpm for 10 min at 4° C. The upper layer was transferred to 4 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol, made with RNase free water and air-dried. The total RNA sample was then redissolved in 500 μl of water, and the amount of RNA was measured by A260 nm using a 1:50 diluted RNA sample. A total of 3.14 mg RNA was obtained.

This total RNA sample was further purified with the Qiagen RNeasy total RNA Midi kit following the manufacturer's protocol. Thus, the total RNA sample was diluted to 2 mL and mixed with 8 mL of buffer RLT with 80 µl of β-mercaptoethanol and 5.6 mL 100% ethanol. The sample was divided into 4 portions and loaded onto 4 RNeasy midid columns. The columns were then centrifuged for 5 min at 4500×g. To wash the columns, 2 mL of buffer RPE was loaded and the columns centrifuged for 2 min at 4500×g. The washing step was repeated once, except that the centrifugation time was extended to 5 min. Total RNA was eluted by applying 250 µl of RNase free water to each column, waiting for 1 min and centrifuging at 4500×g for 3 min.

PolyA(+)RNA was then isolated from the above total RNA sample, following Pharmacia's kit protocol. Briefly, 2 oligo-dT-cellulose columns were used. The columns were washed twice with 1 mL each of high salt buffer. The total RNA sample from the previous step was diluted to 2 mL total volume and adjusted to 10 mM Tris/HCl, pH 8.0, 1 mM EDTA. The sample was heated at 65° C. for 5 min, then placed on ice. Sample buffer (0.4 mL) was added and the sample was then loaded onto the two oligo-dT-cellulose columns under gravity feed. The columns were centrifuged at 350×g for 2 min, washed 2× with 0.25 mL each of high salt buffer, each time followed by centrifugation at 350×g for 2 min. The columns were further washed 3 times with low salt buffer, following the same centrifugation routine. Poly (A)+ RNA was eluted by washing the column 4 times with 0.25 mL each of elution buffer preheated to 65° C., followed by the same centrifugation procedure. The entire purification process was repeated once. Purified poly(A)+RNA was obtained with a concentration of 30.4 ng/µl.

cDNA was generated, using the LD-PCR method specified by BD-Clontech and 0.1 µg of polyA(+) RNA sample. Specifically, for $1^{st}$ strand cDNA synthesis, 3 µl of the poly(A)+ RNA sample was mixed with 1 µl of SMART IV oligo nucleotide (SEQ ID NO:9) and 1 µl of CDSIII/3' PCR primer (SEQ ID NO:10). The mixture was heated at 72° C. for 2 min and cooled on ice for 2 min. To the tube was added the following: 2 µl first strand buffer, 1 µl 20 mM DTT, 1 µl 10 mM dNTP mix and 1 µl Powerscript reverse transcriptase. The mixture was incubated at 42° C. for 1 hr and cooled on ice.

The $1^{st}$ strand cDNA synthesis mixture was used as template for the PCR reaction. Specifically, the reaction mixture contained the following: 2 µl of the $1^{st}$ strand cDNA mixture, 2 µl 5'-PCR primer (SEQ ID NO:11), 2 µl CDSIII/3'-PCR primer (SEQ ID NO:10), 80 µl water, 10 µl 10× Advantage 2 PCR buffer, 2 µl 50×dNTP mix and 2 µl 50× Advantage 2 polymerase mix. The thermocycler conditions were set for 95° C. for 20 sec, followed by 20 cycles of 95° C. for 5 sec and 68° C. for 6 min on a GenAmp 9600 instrument. PCR product was quantitated by agarose gel electrophoresis and ethidium bromide staining.

Example 2

Cloning of a Partial Putative DGAT2 Sequence from *Mortierella alpina* By PCR Using Degenerate PCR Primers PCR amplifications were performed using either *M. alpina* genomic DNA or cDNA as template and several sets of degenerate primers (see Table 4 below) designed to encode conserved amino acid sequences among different known DGAT2s (i.e., GenBank Accession NOs. NC_001147 [*Saccharomyces cerevisiae*] and AF391089 and AF391090 [*Mortierella ramanniana*]). The best results were obtained with degenerate primers MDGAT-FN1 and MDGAT-RN1.

TABLE 4

Degenerate Primers Used For Amplification Of A Partial Putative DGAT2

| Primer Set | Description | Degenerate Nucleotide Sequence | Corresponding Amino Acid Sequence |
|---|---|---|---|
| MDGAT-FN1 | (16) 20-mers | 5'-GAACTACATCTTY GGNTAYCA-3' (SEQ ID NO:12) | NYIFGYH (SEQ ID NO:13) |
| MDGAT-RN1 | (32) 20-mers | 5'-TACAGCTCRTTYT CNCCRAA-3' (SEQ ID NO:14) | Complement of FGENELY (SEQ ID NO:15) |
| MDGAT-RN2 | (32) 20-mers | 5'-CCAAAGTCRTART TRAAAC-3' (SEQ ID NO:16) | Complement of VFNYDFG (SEQ ID NO:17) |

[Note: Abbreviations are standard for nucleotides and proteins. The nucleic acid degeneracy code used is as follows: Y = C/T; R = A/G, and N = A/C/G/T.]

The PCR was carried out in a Perkin Elmer GeneAmp 9600 PCR machine using TaKaRa ExTaq premix Taq polymerase (TaKaRa Bio Inc., Otsu, Shiga, Japan). Amplification was carried out as follows: 30 cycles of denaturation at 94° C. for 30 sec, annealing at 55° C. for 30 sec and elongation at 72° C. for 90 sec, followed by a final elongation cycle at 72° C. for 7 min.

Using cDNA as template, and MDGAT-FN1 and MDGAT-RN1 as primers, a fragment with a size of ca. 370 bp was obtained (SEQ ID NO:18). This fragment was purified with a Qiagen QiaQuick PCR purification kit, cloned into the TOPO® cloning vector pCR2.1-TOPO (In-vitrogen), and sequenced. The resultant sequence, when translated, had homology to known DGAT2s, based on BLAST program analysis (Basic Local Alignment Search Tool; Altschul, S. F., et al., *J. Mol. Biol.* 215:403–410 (1993)).

Using genomic DNA as template, and MDGAT-FN1 and MDGAT-RN2 as primers, a fragment of ca 670 bp was obtained. The fragment was purified, cloned into pCR2.1-TOPO and sequenced, as above. 654 bp of sequence was obtained (SEQ ID NO:19). Again, when translated, the sequence had homology to known DGAT2s, based on the BLAST program analysis. Comparison of the genomic sequence and the cDNA sequence revealed the presence of an intron of 179 bp (SEQ ID NO:20).

Example 3

Isolation of the Full-Length DGAT2 Sequence from *Mortierella alpina*

Based on the sequence of the 370 bp fragment, the 5' and 3' end regions of the *M. alpina* DGAT2 were cloned using genome walking techniques. This enabled assembly of a contig, corresponding to the −747 bp to +1552 bp region of the *M. alpina* DGAT2 (SEQ ID NO:37). This contig included the entire coding region of DGAT2 and three introns.

InVitrogen's 3'-End RACE Protocol

3'-end RACE was carried out using the InVitrogen 3'-end RACE kit, following the manufacturer's protocol. Briefly, 90 ng of *M. alpina* polyA(+)RNA in 11 μl of water was mixed with 1 μl of 10 μM Adaptor primer ("AP"; SEQ ID NO:21) solution. The mixture was heated at 70° C. for 10 min and cooled on ice for 2 min. To this, 2 μl 10×PCR buffer, 2 μl 25 mM MgCl$_2$, 2 μl 0.1 M DTT, and 1 μl of 10 mM dNTP mix were added (from the kit). The reaction mixture was heated to 42° C. for 3 min and then 1 μl of Superscript II reverse transcriptase was added. The reaction was allowed to proceed for 50 min at 42° C., then was heated to 70° C. for 15 min and cooled on ice for 2 min. 1 μl of RNaseH from the kit was added. The entire mixture was then incubated at 37° C. for 20 min.

The above reaction mixture (2 μl) was used directly as a PCR template, while the remainder of the PCR reaction mixture contained 1 μl of 20 μM primer MDGAT-3-1 (SEQ ID NO:22, nested at the 3' end), 2 μl of 10 μM kit primer UAP (SEQ ID NO:23), 25 μl of ExTaq premix Taq 2×PCR solution (TaKaRa Bio Inc., Otsu, Shiga, Japan) and 20 μl of water. PCR amplification was carried out for 30 cycles using the following conditions: denaturation at 94° C. for 30 sec, annealing at 55° C. for 30 sec, and elongation at 72° C. for 90 sec. A final elongation cycle at 72° C. for 7 min was carried out, followed by reaction termination at 4° C.

A second round of PCR was carried out using the same conditions described above, with the exception that the template used was 1 μl of 1:10 diluted PCR reaction mixture and primer MDGAT-3-2 (SEQ ID NO:24, nested at the 3' end) was used in place of primer MDGAT-3-1. This was followed by a third round of PCR using primers MDGAT-3-3 (SEQ ID NO:25, nested at the 3' end) and UAP.

A ca 455 bp fragment was obtained from the PCR. After purification with a Qiagen QiaQuick PCR purification kit, the fragment was cloned into pCR2.1-TOPO and sequenced. Sequence analysis showed that the fragment was the 3'-end of the *M. alpina* DGAT2 cDNA and it included the polyA tail (SEQ ID NO:26).

Genome Walking to Isolate the 3'-End Region of the *M. alpine* DGAT2

A Clontech Universal GenomeWalker™ kit was used to obtain a piece of genomic DNA corresponding to the 3'-end region of the *M. alpina* DGAT2. Briefly, 2.5 μg each of *M. alpina* genomic DNA was digested with DraI, EcoRV, PvuII or StuI individually, the digested DNA samples were purified using Qiagen Qiaquick PCR purification kits and eluted with 30 μl each of kit buffer EB, and the purified samples were then ligated with Genome Walker adaptor (SEQ ID NOs:27 [top strand] and 28 [bottom strand]), as shown below:

```
5'-GTAATACGACTCACTATAGGGCACGCGTGGTCGACGGCCCGGGCTGGT-3'
                                 3'-H2N-CCCGACCA-5'
```

Each ligation reaction mixture contained 1.9 μl of 25 μM Genome Walker adaptor, 1.6 μl 10× ligation buffer, 0.5 μl T4 DNA ligase and 4 μl of one of the purified digested genomic DNA samples. The reaction mixtures were incubated at 16° C. overnight. The reaction was terminated by incubation at 70° C. for 5 min. Then, 72 μl of 10 mM Tris HCl, 1 mM EDTA, pH 7.4 buffer was added to each ligation reaction mix.

Four separate PCR reactions were performed, each using one of the four ligation mixtures as template. The PCR reaction mixtures contained 1 μl of ligation mixture, 1 μl of 20 μM MDGAT-3-1 (SEQ ID NO:22), 2 μl of 10 μM kit primer AP1 (SEQ ID NO:29), 21 μl water, and 25 μl ExTaq premix Taq 2×PCR solution (TaKaRa). The PCR reactions were carried out for 30 cycles using the following conditions: denaturation at 94° C. for 30 sec, annealing at 55° C. for 30 sec, and elongation at 72° C. for 90 sec. A final elongation cycle at 72° C. for 7 min was carried out, followed by reaction termination at 4° C.

The products of each PCR reaction were diluted 1:50 individually and used as templates for a second round of PCR. Each reaction mixture contained 1 μl of one of the diluted PCR product as template, 1 μl of 20 μM MDGAT-3-2 (SEQ ID NO:24), 2 μl of 10 μM kit primer AP2 (SEQ ID NO:30), 21 μl water and 25 μl of ExTaq premix Taq 2×PCR solution (TaKaRa). PCR reactions were carried out for 30 cycles using the same thermocycler conditions described above.

A 674 bp DNA fragment was obtained from the second round of PCR. This fragment was purified and cloned into pCR2.1-TOPO and sequenced. Sequence analysis showed that the fragment was the 3'-end of the *M. alpina* DGAT2 gene (SEQ ID NO:31). Additionally, this fragment was identical to the cDNA fragment (SEQ ID NO:26), with two exceptions: (1) the 3'-end did not extend as far as the cDNA fragment; and (2) two additional regions were present, representing introns that had been spliced off from the cDNA (wherein one intron [SEQ ID NO:20] was located between bases 35–213 of SEQ ID NO:31 and the second intron [SEQ ID NO:33] was located between bases 369–499 of SEQ ID NO:31).

Genome Walking to Isolate the 5'-End Region of the *M. alpine* DGAT2

The same set of four ligation mixtures used in the Clontech 3'-end RACE protocol were also used to obtain the 5'-end region of the *M. alpina* DGAT2. Specifically, a first round of PCR using the same components and conditions as described above was conducted, with the exception that MDGAT-5-1 (SEQ ID NO:34, nested at the 5' end) and AP1 were used as primers. The second round of PCR used MDGAT-5-2 (SEQ ID NO:35, nested at the 5' end) and AP2 as primers. A DNA fragment with 1261 bp was obtained. It was purified and cloned into pCR2.1-TOPO and sequenced. Analysis of the sequence showed that it was the 5'-region of the DGAT2 gene (SEQ ID NO:36).

Assembly of the Full-Length DGAT2 Sequence from *Mortierella alpina*

A 2299 bp sequence (SEQ ID NO:37) containing the complete DGAT2 gene (comprising a region extending 747 bases upstream of the DGAT2 translation initiation 'ATG' codon and extending 62 bases beyond the DGAT2 termination codon) was assembled from the original partial cDNA fragment (SEQ ID NO:18), the partial genomic fragment (SEQ ID NO:19), the 3' cDNA fragment (SEQ ID NO:26) and 3' and 5' genomic sequences (SEQ ID NOs:31 and 36) described above (graphically illustrated in FIG. 3). The complete nucleotide sequence of the *M. alpina* DGAT2 cDNA from 'ATG' to the stop codon 'TAG' is provided as SEQ ID NO:1 (corresponding to bases 748 to 2237 of SEQ ID NO:37, excluding the three introns (i.e., intron 1 [SEQ ID NO:32], corresponding to bases 1018 to 1201 of SEQ ID NO:37; intron 2 [SEQ ID NO:20], corresponding to bases 1570 to 1748 of SEQ ID NO:37; and intron 3 [SEQ ID NO:32], corresponding to bases 1903 to 2034 of SEQ ID NO:37). The translated amino acid sequence (SEQ ID NO:2) showed homology with a number of fungal, plant and animal DGAT2s.

More specifically, identity of the sequence was determined by conducting BLAST (Basic Local Alignment Search Tool; Altschul, S. F., et al., *J. Mol. Biol.* 215:403–410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. *Nature Genetics* 3:266–272 (1993)) provided by the NCBI. The results of the BLAST comparison summarizing the sequence to which SEQ ID NO:2 has the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the amino acid fragment described herein as SEQ ID NO:2 had 47% identity and 66% similarity with the protein sequence of *Mortierella ramanniana* DGAT2A (GenBank Accession No. MK84179.1), with an expectation value of 1e-87; additionally, SEQ ID NO:2 had 47% identity and 65% similarity with hypothetical protein CNBF4150 from *Cryptococcus neoformans* var. *neoformans* B-3501A (GenBank Accession No. EAL20089), with an expectation value of 6e-89.

Example 4

Generation Of EPA-Producing *Yarrowia lipolytica* ATCC #20362 Strain Y2067U

The present Example describes the construction of strain Y2067U, derived from *Yarrowia lipolytica* ATCC #20362, capable of producing significant concentrations of EPA relative to the total lipids (FIG. 4A). The affect of *M. alpina* DGAT2 gene overexpression was examined in this EPA producing strain based on analysis of TAG content, as described in Example 5 (infra).

The development of strain Y2067U herein required the construction of strain M4 (producing 8% DGLA), strain Y2034 (producing 10% ARA), strain E (producing 10% EPA), strain EU (producing 10% EPA) and strain Y2067 (producing 15% EPA).

Construction of Strain M4 Producing 8% DGLA

Construct pKUNF12T6E (FIG. 4B; SEQ ID NO:38) was generated to integrate four chimeric genes (comprising a Δ12 desaturase, a Δ6 desaturase and 2 elongases) into the Ura3 loci of wild type *Yarrowia* strain ATCC #20362, to thereby enable production of DGLA. The pKUNF12T6E plasmid contained the following components:

TABLE 5

Description of Plasmid pKUNF12T6E (SEQ ID NO: 38)

| RE Sites And Nucleotides Within SEQ ID NO: 38 | Description Of Fragment And Chimeric Gene Components |
|---|---|
| AscI/BsiWI (9420-8629) | 784 bp 5' part of *Yarrowia* Ura3 gene (GenBank Accession No. AJ306421) |
| SphI/PacI (12128-1) | 516 bp 3' part of *Yarrowia* Ura3 gene (GenBank Accession No. AJ306421) |
| SwaI/BsiWI (6380-8629) | FBAIN::EL1S:Pex20, comprising: FBAIN: FBAIN promoter (SEQ ID NO: 39; see also U.S. Patent Application No. 10/987548) EL1S: codon-optimized elongase 1 gene (SEQ ID NO: 40), derived from *Mortierella alpina* (GenBank Accession No. AX464731) Pex20: Pex20 terminator sequence from *Yarrowia* Pex20 gene (GenBank Accession No. AF054613) |
| BglII/SwaI (4221-6380) | TEF::Δ6S::Lip1, comprising: TEF: TEF promoter (GenBank Accession No. AF054508) Δ6S: codon-optimized Δ6 desaturase gene (SEQ ID NO: 42), derived from *Mortierella alpina* (GenBank Accession No. AF465281) Lip1: Lip1 terminator sequence from *Yarrowia* Lip1 gene (GenBank Accession No. Z50020) |
| PmeI/ClaI (4207-1459) | FBA::F.Δ12::Lip2, comprising: FBA: FBA promoter (SEQ ID NO: 44; see also U.S. Patent Application No. 10/987548) F.Δ12: *Fusarium moniliforme* Δ12 desaturase gene (SEQ ID NO: 45) Lip2: Lip2 terminator sequence from *Yarrowia* Lip2 gene (GenBank Accession No. AJ012632) |
| ClaI/PacI (1459-1) | TEF::EL2S::XPR, comprising: TEF: TEF promoter (GenBank Accession No. AF054508) EL2S: codon-optimized elongase gene (SEQ ID NO: 47), derived from *Thraustochytrium aureum* (U.S. 6,677,145) XPR: XPR terminator sequence of *Yarrowia* Xpr gene (GenBank Accession No. M17741) |

The pKUNF12T6E plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura- strains. Single colonies of Ura- strains were then inoculated into liquid MMU at 30° C. and shaken at 250 rpm/min for 2 days.

The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E (FIG. 4B), but not in the wild type *Yarrowia* control strain. Most of the selected 32 Ura- strains produced about 6% DGLA of total lipids. There were 2 strains (i.e., strains M4 and 13-8) that produced about 8% DGLA of total lipids.

Construction of Strain Y2034 Producing about 10% ARA

Constructs pDMW232 (FIG. 4C; SEQ ID NO:49) was generated to integrate two Δ5 chimeric genes into the Leu2 gene of *Yarrowia* strain M4. The plasmid pDMW232 contained the following components:

TABLE 6

Description of Plasmid pDMW232 (SEQ ID NO: 49)

| RE Sites And Nucleotides Within SEQ ID NO: 49 | Description Of Fragment And Chimeric Gene Components |
|---|---|
| AscI/BsiWI (5550-4755) | 788 bp 5' part of *Yarrowia* Leu2 gene (GenBank Accession No. AF260230) |
| SphI/PacI (8258-8967) | 703 bp 3' part of *Yarrowia* Leu2 gene (GenBank Accession No. AF260230) |
| SwaI/BsiWI (2114-4755) | FBAIN::MAΔ5::Pex20, comprising: FBAIN: FBAIN Promoter (SEQ ID NO: 39; see also U.S. Patent Application No. 10/987548) MAΔ5: *Mortierella alpina* Δ5 desaturase gene (SEQ ID NO: 50) (GenBank Accession No. AF067654) Pex20: Pex20 terminator sequence of *Yarrowia* Pex20 gene (GenBank Accession No. AF054613) |
| SwaI/ClaI (2114-17) | TEF::MAΔ5::Lip1, comprising: TEF: TEF promoter (GenBank Accession No. AF054508) MAΔ5: as described for FBAIN::MAΔ5::Pex20 (supra) Lip1: Lip1 terminator sequence of *Yarrowia* Lip1 gene (GenBank Accession No. Z50020) |
| PmeI/ClaI (5550-4755) | *Yarrowia* Ura3 gene (GenBank Accession No. AJ306421) |

Plasmid pDMW232 was digested with AscI/SphI, and then used to transform strain M4 according to the General Methods. Following transformation, the cells were plated onto MMLe plates and maintained at 30° C. for 2 to 3 days. The individual colonies grown on MMLe plates from each transformation were picked and streaked onto MM and MMLe plates. Those colonies that could grow on MMLe plates but not on MM plates were selected as Leu2⁻ strains. Single colonies of Leu2⁻ strains were then inoculated into liquid MMLe media at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in pDMW232 transformants, but not in the parental M4 strain. Specifically, among the 48 selected Leu2⁻ transformants with pDMW232, there were 34 strains that produced less than 5% ARA, 11 strains that produced 6–8% ARA, and 3 strains that produced about 10% ARA of total lipids in the engineered *Yarrowia*. One of the strains that produced 10% ARA was named "Y2034".

Construction of Strain E, Producing about 10% EPA

Construct pZP3L37 (FIG. 4D; SEQ ID NO:52) was created to integrate three synthetic Δ17 desaturase chimeric genes into the acyl-CoA oxidase 3 (i.e., POX3) gene of the Y2034 strain. The plasmid pZP3L37 contained the following components:

TABLE 7

Description of Plasmid pZP3L37 (SEQ ID NO: 52)

| RE Sites And Nucleotides Within SEQ ID NO: 52 | Description Of Fragment And Chimeric Gene Components |
|---|---|
| AscI/BsiWI (6813-6043) | 763 bp 5' part of *Yarrowia* Pox3 gene (GenBank Accession No. AJ001301) |
| SphI/PacI (9521-10345) | 818 bp 3' part of *Yarrowia* Pox3 gene (GenBank Accession No. AJ001301) |
| ClaI/BsiWI (4233-6043) | TEF::Δ17S::Pex20, comprising: TEF: TEF promoter (GenBank Accession No. AF054508) Δ17S: codon-optimized Δ17 desaturase gene (SEQ ID NO: 53), derived from *S. diclina* (US 2003/0196217 A1) Pex20: Pex20 terminator sequence of *Yarrowia* Pex20 gene (GenBank Accession No. AF054613) |
| ClaI/PmeI (4233-1811) | FBAIN::Δ17S::Lip2, comprising: FBAIN: FBAIN promoter (SEQ ID NO: 39; see also U.S. Patent Application No. 10/987548) Δ17S: SEQ ID NO: 53 (supra) Lip2: Lip2 terminator sequence of *Yarrowia* Lip2 gene (GenBank Accession No. AJ012632) |
| PmeI/SwaI (1811-1) | *Yarrowia* Leu2 gene (GenBank Accession No. AF260230) |
| PacI/SwaI (10345-1) | FBAINm::Δ17S::Pex16, comprising: FBAINm: FBAINm promoter (SEQ ID NO: 55; see also U.S. Patent Application No. 10/987548) Δ17S: SEQ ID NO: 53 (supra) Pex16: Pex16 terminator sequence of *Yarrowia* Pex16 gene (GenBank Accession No. U75433) |

Plasmid pZP3L37 was digested with AscI/SphI, and then used to transform strain Y2034 according to the General Methods. Following transformation, the cells were plated onto MM plates and maintained at 30° C. for 2 to 3 days. A total of 48 transformants grown on the MM plates were picked and re-streaked onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in most of the transformants with pZP3L37, but not in the parental strain (i.e., Y2034). Among the 48 selected transformants with pZP3L37, there were 18 strains that produced less than 2% EPA, 14 strains that produced 2–3% EPA, and 1 strain that produced about 7% EPA of total lipids in the engineered *Yarrowia*.

The strain that produced 7% EPA was further analyzed after culturing the strain as follows ("two-stage growth conditions"). First, cells were grown in triplicate in liquid MM at 30° C. with shaking at 250 rpm/min for 48 hrs. The cells were collected by centrifugation and the liquid supernatant was extracted. The pelleted cells were resuspended in HGM and grown for 72 hrs at 30° C. with shaking at 250 rpm/min. The cells were again collected by centrifugation and the liquid supernatant was extracted.

GC analyses showed that the engineered strain produced about 10% EPA of total lipids after the two-stage growth. The strain was designated as the "E" strain.

Construction of Strain EU Producing about 10% EPA

Strain EU (Ura⁻) was created by identifying mutant cells of strain E that were 5-FOA resistant. Specifically, one loop of *Yarrowia* E strain cells were inoculated into 3 mL YPD medium and grown at 30° C. with shaking at 250 rpm for 24 hrs. The culture with diluted with YPD to an $OD_{600}$ of 0.4 and then incubated for an additional 4 hrs. The culture was plated (100 μl/plate) onto FOA selection plates and maintained at 30° C. for 2 to 3 days. A total of 16 FOA resistant colonies were picked and streaked onto MM and FOA selection plates. From these, 10 colonies grew on FOA selection plates but not on MM plates and were selected as potential Ura⁻ strains.

One of these strains was used as host for transformation with pY37/F15, comprising a chimeric GPD::*Fusarium moniliforme* Δ15::XPR2 gene and a Ura3 gene as a selection marker (FIG. 5A; SEQ ID NO:56). After three days of selection on MM plates, hundreds of colonies had grown on the plates and there was no colony growth of the transformation control that carried no plasmid. This 5-FOA resistant strain was designated as strain "EU".

Single colonies of the EU strain were then inoculated into liquid MMU additionally containing 0.1 g/L uridine and cultured for 2 days at 30° C. with shaking at 250 rpm/min. The cells were collected by centrifugation, lipids were extracted, and fatty acid methyl esters were prepared by trans-esterification and subsequently analyzed with a Hewlett-Packard 6890 GC. GC analyses showed that the EU strain produced about 10% EPA of total lipids.

Construction of Strain Y2067 Producing about 15% EPA

Plasmid pKO2UF2PE (FIG. 5B; SEQ ID NO:57) was created to integrate a cluster containing two chimeric genes (comprising a heterologous Δ12 desaturase and an elongase) and a Ura3 gene into the native *Yarrowia* Δ12 desaturase gene of strain EU (supra). Plasmid pKO2UF2PE contained the following components:

TABLE 8

Description of Plasmid pKO2UF2PE (SEQ ID NO: 57)

| RE Sites And Nucleotides Within SEQ ID NO: 57 | Description Of Fragment And Chimeric Gene Components |
|---|---|
| AscI/BsiWI (3382-2645) | 730 bp 5' part of *Yarrowia* Δ12 desaturase gene (SEQ ID NO: 58) |
| SphI/EcoRI (6090-6646) | 556 bp 3' part of *Yarrowia* Δ12 desaturase gene (SEQ ID NO: 58) |
| SwaI/BsiWI/ (1-2645) | FBAINm::F.Δ12DS::Pex20, comprising: FBAINm: FBAINm promoter (SEQ ID NO: 55; see also U.S. Patent Application No. 10/987548) F.Δ12: *Fusarium moniliforme* Δ12 desaturase gene (SEQ ID NO: 45) Pex20: Pex20 terminator sequence of *Yarrowia* Pex20 gene (GenBank Accession No. AF054613) |
| SwaI/PmeI (1-8525) | GPAT::EL1S::OCT, comprising: GPAT: GPAT promoter (SEQ ID NO: 60; see also U.S. Patent Application No. 60/610060) EL1S: codon-optimized elongase 1 gene (SEQ ID NO: 40), derived from *Mortierella alpina* (GenBank Accession No. AX464731) OCT: OCT terminator sequence of *Yarrowia* OCT gene (GenBank Accession No. X69988) |
| EcoRI/PacI (6646-8163) | *Yarrowia* Ura3 gene (GenBank Accession No. AJ306421) |

Plasmid pKO2UF2PE was digested with AscI/SphI and then used to transform strain EU according to the General Methods (although strain EU was streaked onto a YPD plate and grown for approximately 36 hr prior to suspension in transformation buffer [versus 18 hrs]). Following transformation, cells were plated onto MM plates and maintained at 30° C. for 2 to 3 days. A total of 72 transformants grown on MM plates were picked and re-streaked separately onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in almost all of the transformants with pKO2UF2PE. More specifically, among the 72 selected transformants, there were 17 strains that produced 8–9.9% EPA, 27 strains that produced 10–10.9% EPA, 16 strains that produced 11–11.9% EPA, and 7 strains that produced 12–12.7% EPA of total lipids in the engineered *Yarrowia*. The strain that produced 12.7% EPA was further analyzed by using two-stage growth conditions. GC analyses showed that the engineered strain produced about 15% EPA of total lipids after the two-stage growth. The strain was designated as strain "Y2067".

Construction of Strain Y2067U Producing about 14% EPA with Ura-Phenotype

In order to disrupt the Ura3 gene in Y2067 strain, construct pZKUT16 (FIG. 5C; SEQ ID NO:61) was created to integrate a TEF::rELO2S::Pex20 chimeric gene into the Ura3 gene of strain Y2067. rELO2S is a codon-optimized rELO gene encoding a rat hepatic enzyme that elongates 16:0 to 18:0. The plasmid pZKUT16 contained the following components:

TABLE 9

Description of Plasmid pZKUT16 (SEQ ID NO: 61)

| RE Sites And Nucleotides Within SEQ ID NO: 61 | Description Of Fragment And Chimeric Gene Components |
|---|---|
| BsiWI/PacI (1-721) | 721 bp 5' part of *Yarrowia* Ura3 gene (GenBank Accession No. AJ306421) |
| SalI/ClaI (3565-4289) | 724 bp 3' part of *Yarrowia* Ura3 gene (GenBank Accession No. AJ306421) |
| ClaI/BsiWI (4289-1) | TEF::rELO2S::Pex20, comprising: TEF: TEF Promoter (GenBank Accession No. AF054508) rELO2S: codon-optimized rELO2 elongase gene (SEQ ID NO: 62), derived from rat (GenBank Accession No. AB071986) Pex 20: Pex20 terminator sequence of *Yarrowia* Pex20 gene (GenBank Accession No. AF054613) |

The plasmid pZKUT16 was digested with SalI/PacI, and then used to transform Y2067 strain according to the General Methods. Following transformation, cells were plated onto FOA selection plates and maintained at 30° C. for 2 to 3 days.

A total of 24 transformants grown on FOA plates were picked and re-streaked onto MM plates and FOA plates, separately. The strains that could grow on FOA plates, but not on MM plates, were selected as Ura-strains. A total of 10 Ura-strains were individually inoculated into liquid MMU media at 30° C. and grown with shaking at 250 rpm/min for 1 day. The cells were collected by centrifugation, lipids were extracted, and fatty acid methyl esters were prepared by trans-esterification, and subsequently analyzed with a Hewlett-Packard 6890 GC.

GC analyses showed the presence of 5 to 7% EPA in all of the transformants with pZKUT16 after one day growth in MMU media. The strain that produced 6.2% EPA was further analyzed using two-stage growth conditions (48 hrs MM+96 hrs in HGM). GC analyses showed that the engineered strain produced about 14% EPA of total lipids. The strain was designated as strain "Y2067U". The final genotype of this strain with respect to wildtype *Yarrowia lipolytica* ATCC #20362 was as follows: Ura3-, Pox3-, Y.Δ12-, FBA::F.Δ12::Lip2, FBAINm::F. Δ12::Pex20, TEF::Δ6S:: Lip1, FBAIN::E1S::Pex20; GPAT::E1S:: Oct, TEF::E2S:: Xpr; FBAIN::MAΔ5::Pex20, TEF::MAΔ5::Lip1, FBAIN:: Δ17S::Lip2, FBAINm::Δ17S::Pex16, TEF::Δ17S::Pex20 and TEF::rELO2S::Pex20.

Example 5

Heterologous Expression of the *Mortierella alpina* DGAT2 ORF Under the Control of a *Yarrowia* Promoter in *Yarrowia lipolytica*

The present Example describes the over-expression of the *M. alpina* DGAT2 ORF in a chimeric gene under the control of a *Yarrowia lipolytica* promoter in *Y. lipolytica* strain Y2067U, and the affect of the overexpression as determined by an analysis of TAG content.

The *M. alpina* DGAT2 ORF was cloned into plasmid pZUF17 (SEQ ID NO:64; FIG. 5D) such that the gene was under the control of the *Y. lipolytica* FBAIN promoter and the PEX20-3' terminator region in the auto-replicating vector for expression in *Y. lipolytica*. First, the ORF was PCR-amplified using upper primer MDGAT-F (SEQ ID NO:65) and lower primer MDGAT-R1 (SEQ ID NO:66) from the *M. alpina* cDNA (supra, Example 1). The expected 1015 bp fragment was isolated, purified, digested with Nco I and Not I and cloned into Nco I-Not I cut pZUF17 vector. Correct transformants were confirmed by miniprep analysis and the resultant plasmid was designated as "pMDGAT2-17" (SEQ ID NO:67).

"Control" vector pZUF-MOD-1 (SEQ ID NO:68; FIG. 5E) was prepared as follows. First, primers pzuf-mod1 (SEQ ID NO:69) and pzuf-mod2 (SEQ ID NO:70) were used to amplify a 252 bp "stuffer" DNA fragment using pDNR-LIB (ClonTech, Palo Alto, Calif.) as template. The amplified fragment was purified with a Qiagen QiaQuick PCR purification kit, digested with NcoI and NotI using standard conditions, and then purified again with a QiaQuick PCR purification kit. This fragment was ligated at room temperature overnight into similarly digested NcoI-/NotI-cut pZUF17 vector (wherein the ligation consisted of 0.5 µg of the digested PCR fragment and 0.3 µg of ~7079 bp digested pZUF17 vector fragment with 2 µl of 10×T4 ligase buffer and 3 units of T4 DNA ligase (Promega) in a total volume of 20 µl) and the resulting ligation mixture was used to transform *E. coli* Top10 cells (Invitrogen). Plasmid DNA was purified from 4 resulting colonies, using a Qiagen QiaPrep Spin Miniprep kit. The purified plasmids were digested with NcoI and NotI to confirm the presence of the ~250 bp fragment. The resulting plasmid was named "pZUF-MOD-1".

*Y. lipolytica* strain Y2067U (from Example 4, producing 14% EPA of total lipids) was transformed with pMDGAT2-17 and pZUF-MOD-1, respectively, according to the General Methods. Transformants were grown for 2 days in synthetic MM supplemented with amino acids, followed by 4 days in HGM. The fatty acid profile of two transformants containing pMDGAT2-17 and two transformants containing pZUF-MOD-1 are shown below based on GC analysis (as described in the General Methods). Fatty acids are identified as 18:0, 18:1 (oleic acid), 18:2 (LA), GLA, DGLA, ARA, ETA and EPA; and the composition of each is presented as a % of the total fatty acids.

TABLE 10

Lipid Content In *Yarrowia* Strain Y2067U Engineered To Overexpress *M. alpina* DGAT2

| Strain | Total Fatty Acids | | | | | | | |
| --- | --- | --- | --- | --- | --- | --- | --- | --- |
| | 18:0 | 18:1 | 18:2 | GLA | DGLA | ARA | ETA | EPA |
| Y2067U + pZUF-MOD-1 #1 | 1.31 | 6.92 | 12.03 | 23.11 | 5.72 | 1.05 | 3.80 | 13.20 |
| Y2067U + pZUF-MOD-1 #2 | 1.39 | 6.83 | 12.15 | 21.99 | 5.83 | 1.07 | 3.82 | 13.47 |
| Y2067U + pMDGAT2-17 #1 | 0.00 | 7.47 | 10.77 | 25.30 | 5.70 | 1.43 | 3.45 | 15.12 |
| Y2067U + pMDGAT2-17 #2 | 1.45 | 7.79 | 9.96 | 25.16 | 6.06 | 1.25 | 3.99 | 15.37 |

Expression of the *M. alpina* DGAT2 from plasmid pMDGAT2-17 increased the EPA concentration from ~13.3% in the "control" strains to ~15.25% ("Y2067U+pMDGAT2-17"). An additional increase in EPA would be expected, if the native *Yarrowia lipolytica* DAG ATs [i.e., DGAT2 (SEQ ID NOs:3–8), DGAT1 and/or PDAT] were knocked-out in strain Y2067U+pMDGAT2-17 using means well known to one of skill in the art.

What is claimed is:

1. An isolated nucleic acid molecule selected from the group consisting of:
   (a) an isolated nucleic acid molecule encoding a diacylglycerol acyltransferase 2 enzyme, having the amino acid sequence as set forth in SEQ ID NO:2;
   (b) an isolated nucleic acid molecule encoding an diacylglycerol acyltransferase 2 enzyme, that hybridizes with (a) under the following hybridization conditions: 0.1×SSC, 0.1% SDS, 65° C. and washed with 2×SSC, 0.1% SDS followed by 0.1×SSC, 0.1% SDS; or
   (c) an isolated nucleic acid molecule that is completely complementary to (a) or (b).

2. The isolated nucleic acid molecule of claim 1 as set forth in SEQ ID NO:1.

3. A chimeric gene comprising the isolated nucleic acid molecule of claim 1 operably linked to suitable regulatory sequences.

4. An isolated host cell comprising the chimeric gene of claim 3.

5. An isolated host cell of claim 4, selected from the group consisting of algae, bacteria, molds, fungi and yeast.

6. An isolated host cell of claim 5, wherein the yeast is an oleaginous yeast.

7. An isolated host cell of claim 6, wherein the oleaginous yeast cell is selected from the group consisting of *Yarrowia, Candida, Rhodotorula, Rhodosporidlum, Cryptococcus, Trichosporon* and *Lipomyces*.

8. An isolated host cell of claim 7, wherein the host cell is *Yarrowia lipolyzica*.

* * * * *

UNITED STATES PATENT AND TRADEMARK OFFICE
CERTIFICATE OF CORRECTION

PATENT NO. : 7,198,937 B2
APPLICATION NO. : 11/024545
DATED : April 3, 2007
INVENTOR(S) : Zhixiong Xue, Narendra S. Yadav and Daniel Joseph Macool It is certified that error appears in the above-identified patent and that said Letters Patent is hereby corrected as shown below:

Column 8, line 34: change "γ-Linoleic" to --γ-Linolenic--
Column 8, line 37: change "Dihomo-γ-Linoleic" to --Dihomo-γ-Linolenic--
Column 18, line 26; change "dihomo-γ-linoleic" to --dihomo-γ-linolenic--
Column 194, line 12: change "Rhodosporidlum" to --Rhodosporidium--
Column 194, line 15: change "lipolyzica" to --lipolytica--

Signed and Sealed this

Eleventh Day of December, 2007

JON W. DUDAS
*Director of the United States Patent and Trademark Office*